US011708614B2

(12) United States Patent
Torres-Gonzalez et al.

(10) Patent No.: US 11,708,614 B2
(45) Date of Patent: Jul. 25, 2023

(54) ASSAYS AND METHODS FOR DETERMINING MICROBIAL RESISTANCE

(71) Applicant: STRECK, LLC, La Vista, NE (US)

(72) Inventors: Maria Torres-Gonzalez, Omaha, NE (US); Nancy Hanson, Omaha, NE (US); Joel Lechner, Omaha, NE (US); Stephanie Cossette, Omaha, NE (US); Cathy Scheer, Omaha, NE (US); Matthew R. Kreifels, Elkhorn, NE (US); Stacey Morrow, Omaha, NE (US); Christopher Connelly, Gretna, NE (US); Laura R. Porter, Omaha, NE (US); Randy Fowler, Broomfield, CO (US)

(73) Assignees: STRECK LLC, La Vista, NE (US); CREIGHTON UNIVERSITY, Omaha, NE (US)

( * ) Notice: Subject to any disclaimer, the term of this patent is extended or adjusted under 35 U.S.C. 154(b) by 441 days.

(21) Appl. No.: 16/310,074

(22) PCT Filed: Jun. 15, 2017

(86) PCT No.: PCT/US2017/037700
§ 371 (c)(1),
(2) Date: Dec. 14, 2018

(87) PCT Pub. No.: WO2017/218789
PCT Pub. Date: Dec. 21, 2017

(65) Prior Publication Data
US 2019/0330685 A1 Oct. 31, 2019

Related U.S. Application Data

(60) Provisional application No. 62/350,457, filed on Jun. 15, 2016.

(51) Int. Cl.
C12Q 1/689 (2018.01)
C12Q 1/6809 (2018.01)
C12Q 1/6837 (2018.01)
C12Q 1/6851 (2018.01)
C12Q 1/686 (2018.01)

(52) U.S. Cl.
CPC ............ C12Q 1/689 (2013.01); C12Q 1/686 (2013.01); C12Q 1/6809 (2013.01); C12Q 1/6837 (2013.01); C12Q 1/6851 (2013.01); C12Q 2545/101 (2013.01); C12Q 2600/106 (2013.01); C12Q 2600/16 (2013.01); C12Q 2600/166 (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,845,205 A | 7/1989 | Huynh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,539,082 A | 7/1996 | Nielsen et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,242,223 B1 | 6/2001 | Hanson et al. |
| 6,893,846 B2 | 5/2005 | Hanson et al. |
| 6,905,848 B2 | 6/2005 | Hanson et al. |
| 7,045,291 B2 | 5/2006 | Hanson et al. |
| 7,476,520 B2 | 1/2009 | Hanson et al. |
| 7,521,547 B2 | 4/2009 | Hanson et al. |
| 9,120,840 B2 | 9/2015 | Janssen et al. |

(Continued)

FOREIGN PATENT DOCUMENTS

| | | |
|---|---|---|
| CN | 104946764 A | 9/2015 |
| EP | 1072679 A2 | 1/2001 |

(Continued)

OTHER PUBLICATIONS

Integrated DNA Technologies, Better PCR probes: A second quencher lowers backrgound, increasing signal detection, 2021. (Year: 2021).*

(Continued)

Primary Examiner — Samuel C Woolwine
Assistant Examiner — Carolyn L Greene
(74) Attorney, Agent, or Firm — Marshall, Gerstein & Borun LLP

(57) ABSTRACT

Assays and methods for detecting resistance to beta-lactam antibiotics including detection of multiple β-lactamase family specific gene targets by polymerase chain reaction or microarray. One or more kits including primers and/or probes for identification of β-lactamase genes selected from the group consisting of one or more of the following: MOX-like, FOX-like, ACC-like, ACT/MIR-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. A kit may also include one or more primers and/or probes for the identification a non-beta lactamase gene family which confers antibiotic resistance, such as the MCR-1 gene.

21 Claims, 9 Drawing Sheets
Specification includes a Sequence Listing.

(56) References Cited

U.S. PATENT DOCUMENTS

| | | | |
|---|---|---|---|
| 2003/0219749 | A1 | 11/2003 | Hanson et al. |
| 2007/0248954 | A1 | 10/2007 | Hanson |
| 2009/0197275 | A1 | 8/2009 | Boonyarantanakornkit et al. |
| 2016/0085912 | A1* | 3/2016 | Jones ..................... G16H 50/80 702/19 |
| 2019/0017774 | A1 | 1/2019 | Vanek et al. |

FOREIGN PATENT DOCUMENTS

| | | | |
|---|---|---|---|
| WO | 1997/12896 | A1 | 4/1997 |
| WO | 1998/39352 | A1 | 9/1998 |
| WO | 1999/06594 | A1 | 2/1999 |
| WO | 1999/14226 | A2 | 3/1999 |
| WO | 2010/130882 | A1 | 11/2010 |
| WO | WO-2012/027302 | A2 | 3/2012 |
| WO | WO-2015/138991 | A2 | 9/2015 |
| WO | 2016/067047 | A1 | 5/2016 |
| WO | 2017/218789 | A1 | 12/2017 |

OTHER PUBLICATIONS

"Streck ARM-D Kits," Jun. 22, 2017.
Anandan et al., Structure of a lipid A phosphoethanolamine transferase suggests how conformational changes govern substrate binding, Proc. Nat. Acad. Sci. USA, 114(9):2218-2223 (2017).
Antunes et al., Acquired Class D ß-Lactamases, Antibiotics, 3(3):398-434 (2014).
Beck et al., Digital Droplet PCR for Rapid Quantification of Donor DNA in the Circulation of Transplant Recipients as a Potential Universal Biomarker of Graft Injury, Clinical Chemistry, 59(12):1732-41 (2013).
Borowiak et al., Identification of a novel transposon-associated phosphoethanolamine transferase gene, mcr-5, conferring colistin resistance in d-tartrate fermenting *Salmonella enterica* subsp. *enterica serovar* Paratyphi B, J. Antimicrob Chemother, 72:3317-3324 (2017).
Carattoli et al., Novel plasmid-mediated colistin resistance mcr-4 gene in *Salmonella* and *Escherichia coli*, Italy 2013, Spain and Belgium 2015 to 2016, Euro Surveill, 22(31):30589 (2017).
Concise encyclopedia of polymer science and engineering, J. I. Kroschwitz Ed., John Wiley & Sons, 858-859 (1990).
Connelly et al., Antiobiotic Resistance Monitoring and Detection (ARM-D™) PCR Kits: ARM-D™ for b-Lactamase ID—Technical Note—Detection of ESBLs, MBLs, KPCs, and plasmid-mediated AmpCs, using the b-Lactamase ID kit to identify antiuobiotic resistance in Gram-negative pathogens, Biotechniques Rapid Dispatches, 57(6):317-318 (2014).
Cook, Medicinal chemistry of antisense oligonucleotides-future opportunities, Anti-Cancer Drug Design, 6(6):585-607 (1991).
Cussac et al., Reduction of the toxicity and mutagenicity of aziridine in mammalian cells harboring the *Escherichia coli* fpg gene, Nucleic Acids Research, 24(9):1742-1746 (1996).
Ebili et al., "Squirrel" Primer-Based PCR Assay for Direct and Targeted Sanger Sequencing of Short Genomic Segments, J. Biomol. Tech., 28(3):97-110 (2017).
Englisch et al., Chemically Modified Oligonucleotides as Probes and Inhibitors, Angew. Chem. Int. Ed., 30(6):613-629 (1991).
Evans et al., OXA ß-Lactamases, Clinical Microbiology Reviews, 27(2):241-263 (2014).
Extended European Search Report dated Oct. 21, 2016; Application No. 15196213.1 (1251.036EPD1).
Freier et al., The ups and downs of nucleic acid duplex stability: structure-stability studies on chemically-modified DNA:RNA duplexes, Nucl. Acid. Res., 25:4429-4443 (1997).
Hanson, One 20-minute multiplex assay for the detection of 10 targets including ampCs, ESBLs, MBLs, and KPCs using rapid PCR amplification, Center for Research in Anti-Infectives and Biotechnology Creighton University Omaha, NE, 19 (2014).
International Preliminary Report on Patentability for International Application No. PCT/US2014/047551 dated Dec. 10, 2015.
International Preliminary Report on Patentability from International Application No. PCT/US2012/036304 dated Aug. 16, 2013.
International Preliminary Report on Patentability from International Application No. PCT/US2017/37700, dated Dec. 27, 2018.
International Search Report and Written Opinion from International Application No. PCT/US20/35422 dated Nov. 13, 2020.
International Search Report and Written Opinion from International Application No. PCT/US2012/036304 dated Nov. 21, 2012.
International Search Report and Written Opinion from International Application No. PCT/US2017/046537 dated Oct. 23, 2017.
Nielsen et al., Sequence-selective recognition of DNA by strand displacement with a thymine-substituted polyamide, Science, 254(5037):1497-1500 (1991).
Poirel et al., Diversity, epidemiology, and genetics of class D beta-lactamases, Antimicrobial Agents and Chemotherapy, 54(1):24-38 (2010).
Sanghvi, Chapter 15, Antisense research and applications, Ed. S. T. Crooke and B. Lebleu, CRC Press, 289-302 (1993).
Silbert, Evaluation of different tests to screen and identify carbapenemase-production bacteria strains, Microbiology, 43 (2019).
Streck, Philisa ampC ID Kit Ad—CAP Today, Identify the threat of antibiotic resistant bacteria faster, 1 page (May 2014).
Streck, Philisa ampC ID Kit Ad—CLP, Identify the threat of antibiotic resistant bacteria faster, 1 page (Sep. 2014).
Streck, Philisa ampC ID Kit JMD, Identify the threat of antibiotic resistant bacteria faster with the philisa (Registered) ampC ID kit, 1 page (Nov. 2014).
Streck, Philisa ampC ID Kit Poster Ad—CAP Today, Identify the threat of antibiotic resistant bacteria faster with the philisa (Registered) ampC ID kit, 1 page (Oct. 2014).
The Streck ARM-D (Registered) kits are multiplex real-time PCR kits for the detection of clinically-relevant(Beta)-lactamase genes, Product Overview, 27 pages.
Vandenbussche et al., A Tale of Tails: Dissecting the Enhancing Effect of Tailed Primers in Real-Time PCR, PLoS One, 11(10):e0164463 (2016).
Vázquez-Ucha et al., Activity of the ß-Lactamase Inhibitor LN-1-255 against Carbapenem-Hydrolyzing Class D ß-Lactamases from Acinetobacter baumannii, Antimicrobial Agents and Chemotherapy, 61(11):e01172-17 (2017).
Yin et al., Novel Plasmid-Mediated Colistin Resistance Gene mcr-3 in *Escherichia coli*, mBIO, 8(3):e00543-17 (2017).
"Antibiotic resistance gene sequence, SEQ ID 227", Apr. 12, 2012, Accessin No. ART75073.
"Antibiptic resistance gene CFE-1 forward PCR primer, SEQ ID 120", Nov. 5, 2015, Accession No. BCE41068.
"Citrobacter freundii strain 90757 class C beta-lactamase CMY-39 gene, complete cds." Jul. 27, 2020, Accession No. HM565135.
"Citrobacter freundii strain W704 AmpR transcriptional regulator (ampR) and AmpC beta-lactamase CMY-80 (blaCMY-80) genes, complete cds; and outer membrane lipoprotein Blc (blc) gene, partial cds." Jun. 3, 2012, Accession No. JQ733577.
"Citrobacter freundii strain W811 transcriptional regulator AmpR (ampR) gene, partial cds; beta-lactamase AmpC (blaCMY-86) gene, complete cds; and outer membrane lipoprotein Blc (blc) gene, partial cds." Mar. 12, 2014, Accession No. KJ207204.
"*Escherichia coli* beta-lactamase gene fragment, SEQ ID 7.", Apr. 7, 2016, Accession No. BCM28931.
"*Escherichia coli* strain 2011/34/01 AmpC beta-lactamase (blaCMY-108) gene, complete cds." Jun. 4, 2014, Accession No. KF564648.
Geyer et al., "Development of a TaqMan Multiplex PCR Assay for Detection of Plasmid-Mediated AmpC ?-Lactamase Genes," Journal of Clinical Microbiology 50(11):3722-3725 (2012).
International Search Report and Written Opinion from International Application No. PCT/US2017/037700 dated Dec. 21, 2017.
Moland et al., "Occurrency of Newer β-Lactamases in Klebsiella pneumoniae Isolates from 24 U.S. Hospitals," Antimicrobial Agents and Chemotherapy, 46(12):3837-3842 (2002).
Perez-Perez et al., "Detection of Plasmid-Mediated AmpC β-Lactamase Genes in Clinical Isolates by Using Multiplex PCR," Journal of Clinical Microbiology 40(6):2153-2162 (2002).

(56) References Cited

OTHER PUBLICATIONS

Pitout et al., "Phenotypic and Molecular Detection of CTX-M-β-Lactamases Produced by *Escherichia coli* and *Klebsiella* spp.," Journal of Clinical Microbiology 42(12):5715-5721 (2004).

Alao et al., Detection of mobilized colistin resistance (mcr) genes by multiplex real-time PCR: improving surveillance of an emerging threat, APHL, 1 (2019).

Declaration of Nicole Quackenbush, dated Mar. 8, 2022, filed during the prosecution of U.S. Appl. No. 16/310,074.

Torres et al., Rapid detection of OXA (Beta)-lactamases by multiplex real-time PCR, Streck Research and Development—Molecular Technology Division, La Vista, NE, 1 (2011).

Torres et al., Rapid detection of plasmid-mediated ampC (Beta)-lactamase genes by multiplex real-time PCR, Streck, Research and Development, Molecular Technology Division, 1 (2015).

Alao et al., Detection of mobilized colistin resistance (mcr) genes by multiplex real-time PCR: improving surveillance of an emerging threat, Association of Public Health Laboratories (APHL) Conference, 6 pages (Jun. 4, 2019). Poster presentation.

Alao et al., Improved methodology for detection of antibiotic resistance in gram-negative bacteria, European Congress of Clinical Microbiology and Infectious Diseases (ECCMID) Conference, 14 pages. (Apr. 24, 2018). Poster presentation.

Hernandez et al., Stability study of (Beta)-lactamase detection from gram-negative bacilli directly from positive blood cultures using two commercially available PCR kits, American Society for Microbiology (ASM) Microbe 2018 Conference, 8 pages. (Jun. 8, 2018). Poster presentation.

Torres et al., Detection of ESBLs, MBLs, KPCs, and plasmid-mediated ampC (Beta)-lactamase genes by multiplex real-time PCR, American Society for Microbiology (ASM) Microbe 2016 Conference, 12 pages. (Jun. 18, 2016). Poster presentation.

Cossette et al., Rapid detection of OXA (Beta)-lactamases by multiplex real-time PCR, American Society for Microbiology (ASM) Microbe 2018 Conference, 8 pages (Jun. 8, 2018). Poster presentation.

Torres et al., Rapid detection of plasmid-mediated ampC (Beta)-lactamase genes by multiplex real-time PCR, American Society for Microbiology (ASM) Microbe 2015 Conference, 10 pages (May 31, 2015). Poster presentation.

* cited by examiner

SEQUENCE LISTING

```
<160> NUMBER OF SEQ ID NOS: 302

<210> SEQ ID NO 1
<211> LENGTH: 18
<212> TYPE: DNA
<213> ORGANISM: Artificial Sequence
<220> FEATURE:
<223> OTHER INFORMATION: MOX F'

<400> SEQUENCE: 1
agaccctgtt cgagatag                                                 18

<210> SEQ ID NO 2
<211> LENGTH: 18
<212> TYPE: DNA
<213> ORGANISM: Artificial Sequence
<220> FEATURE:
<223> OTHER INFORMATION: MOX R'

<400> SEQUENCE: 2
atggtgatgc tgtcaaag                                                 18

<210> SEQ ID NO 3
<211> LENGTH: 20
<212> TYPE: DNA
<213> ORGANISM: Artificial Sequence
<220> FEATURE:
<223> OTHER INFORMATION: MOX-FAM

<400> SEQUENCE: 3
cgtgagcaag accctgactg                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: FOX F'

<400> SEQUENCE: 4
actatttcaa ctatggggtt                                                    20

<210> SEQ ID NO 5
<211> LENGTH: 18
<212> TYPE: DNA
<213> ORGANISM: Artificial Sequence
<220> FEATURE:
<223> OTHER INFORMATION: TTG TCA TCC AGC TCA AAG

<400> SEQUENCE: 5
ttgtcatcca gctcaaag                                                      18

<210> SEQ ID NO 6
<211> LENGTH: 18
<212> TYPE: DNA
<213> ORGANISM: Artificial Sequence
<220> FEATURE:
<223> OTHER INFORMATION: FOX-TEX

<400> SEQUENCE: 6
tgaccgcagc ataggcac                                                      18

<210> SEQ ID NO 7
<211> LENGTH: 18
<212> TYPE: DNA
<213> ORGANISM: Artificial Sequence
<220> FEATURE:
<223> OTHER INFORMATION: EBC F'

<400> SEQUENCE: 7
gtggcggtga tttatgag                                                      18

<210> SEQ ID NO 8
<211> LENGTH: 23
<212> TYPE: DNA
<213> ORGANISM: Artificial Sequence
<220> FEATURE:
<223> OTHER INFORMATION: EBC R'

<400> SEQUENCE: 8
cggtgaaggt tttacttata gaa                                                23

<210> SEQ ID NO 9
<211> LENGTH: 19
<212> TYPE: DNA
<213> ORGANISM: Artificial Sequence
<220> FEATURE:
<223> OTHER INFORMATION: EBC-HEX

<400> SEQUENCE: 9
cagccgcact acttcacct                                                     19

<210> SEQ ID NO 10
<211> LENGTH: 21
<212> TYPE: DNA
<213> ORGANISM: Artificial Sequence
<220> FEATURE:
<223> OTHER INFORMATION: DHA F'

<400> SEQUENCE: 10
tgcgtacggt tatgagaaca a                                                  21
```

```
<210> SEQ ID NO 11
<211> LENGTH: 18
<212> TYPE: DNA
<213> ORGANISM: Artificial Sequence
<220> FEATURE:
<223> OTHER INFORMATION: DHA R'

<400> SEQUENCE: 11
cccagcgcag catatctt                                                 18

<210> SEQ ID NO 12
<211> LENGTH: 24
<212> TYPE: DNA
<213> ORGANISM: Artificial Sequence
<220> FEATURE:
<223> OTHER INFORMATION: DHA-FAM

<400> SEQUENCE: 12
atgcggaatc ttacggcgtg gaat                                          24

<210> SEQ ID NO 13
<211> LENGTH: 19
<212> TYPE: DNA
<213> ORGANISM: Artificial Sequence
<220> FEATURE:
<223> OTHER INFORMATION: CMY F'

<400> SEQUENCE: 13
tccagcgtta ttgatatgg                                                19

<210> SEQ ID NO 14
<211> LENGTH: 18
<212> TYPE: DNA
<213> ORGANISM: Artificial Sequence
<220> FEATURE:
<223> OTHER INFORMATION: CMY R'

<400> SEQUENCE: 14
catctcccag cctaatcc                                                 18

<210> SEQ ID NO 15
<211> LENGTH: 21
<212> TYPE: DNA
<213> ORGANISM: Artificial Sequence
<220> FEATURE:
<223> OTHER INFORMATION: CMY-TEX

<400> SEQUENCE: 15
acatatcgcc aatacgccag t                                             21

<210> SEQ ID NO 16
<211> LENGTH: 20
<212> TYPE: DNA
<213> ORGANISM: Artificial Sequence
<220> FEATURE:
<223> OTHER INFORMATION: ACC F'

<400> SEQUENCE: 16
gccgctgatg cagaagaata                                               20

<210> SEQ ID NO 17
<211> LENGTH: 20
<212> TYPE: DNA
<213> ORGANISM: Artificial Sequence
<220> FEATURE:
<223> OTHER INFORMATION: ACC R'
```

```
<400> SEQUENCE: 17
tttgccgcta acccatagtt                                              20

<210> SEQ ID NO 18
<211> LENGTH: 11
<212> TYPE: DNA
<213> ORGANISM: Artificial Sequence
<220> FEATURE:
<223> OTHER INFORMATION: ACC-HEX

<400> SEQUENCE: 18
ccgacatacc g                                                       11

<210> SEQ ID NO 19
<211> LENGTH: 20
<212> TYPE: DNA
<213> ORGANISM: Artificial Sequence
<220> FEATURE:
<223> OTHER INFORMATION: IC F'

<400> SEQUENCE: 19
gagaggatga ccagccacac                                              20

<210> SEQ ID NO 20
<211> LENGTH: 21
<212> TYPE: DNA
<213> ORGANISM: Artificial Sequence
<220> FEATURE:
<223> OTHER INFORMATION: IC R'

<400> SEQUENCE: 20
agtactttac aacccgaagg c                                            21

<210> SEQ ID NO 21
<211> LENGTH: 25
<212> TYPE: DNA
<213> ORGANISM: Artificial Sequence
<220> FEATURE:
<223> OTHER INFORMATION: IC-TYE

<400> SEQUENCE: 21
tgagacacgg tccagactcc tacgg                                        25

<210> SEQ ID NO 22
<211> LENGTH: 18
<212> TYPE: DNA
<213> ORGANISM: Artificial Sequence
<220> FEATURE:
<223> OTHER INFORMATION: CTX-M-14 F'

<400> SEQUENCE: 22
ttggtgacgt ggctcaaa                                                18

<210> SEQ ID NO 23
<211> LENGTH: 21
<212> TYPE: DNA
<213> ORGANISM: Artificial Sequence
<220> FEATURE:
<223> OTHER INFORMATION: CTX-M-14 R'

<400> SEQUENCE: 23
atatcattgg tggtgccgta g                                            21
```

```
<210> SEQ ID NO 24
<211> LENGTH: 24
<212> TYPE: DNA
<213> ORGANISM: Artificial Sequence
<220> FEATURE:
<223> OTHER INFORMATION: CTX-M-14-FAM

<400> SEQUENCE: 24
cgtggactgt gggtgataag accg                                              24

<210> SEQ ID NO 25
<211> LENGTH: 21
<212> TYPE: DNA
<213> ORGANISM: Artificial Sequence
<220> FEATURE:
<223> OTHER INFORMATION: CTX-M-15 F'

<400> SEQUENCE: 25
gtcacgctgt tgttaggaag t                                                 21

<210> SEQ ID NO 26
<211> LENGTH: 21
<212> TYPE: DNA
<213> ORGANISM: Artificial Sequence
<220> FEATURE:
<223> OTHER INFORMATION: CTX-M-15 R'

<400> SEQUENCE: 26
taatcaatgc cacacccagt c                                                 21

<210> SEQ ID NO 27
<211> LENGTH: 24
<212> TYPE: DNA
<213> ORGANISM: Artificial Sequence
<220> FEATURE:
<223> OTHER INFORMATION: CTX-M-15-TEX615

<400> SEQUENCE: 27
aacttgccga attagagcgg cagt                                              24

<210> SEQ ID NO 28
<211> LENGTH: 24
<212> TYPE: DNA
<213> ORGANISM: Artificial Sequence
<220> FEATURE:
<223> OTHER INFORMATION: OXA48-F'

<400> SEQUENCE: 28
agcagcaagg atttaccaat aatc                                              24

<210> SEQ ID NO 29
<211> LENGTH: 21
<212> TYPE: DNA
<213> ORGANISM: Artificial Sequence
<220> FEATURE:
<223> OTHER INFORMATION: OXA48-R'

<400> SEQUENCE: 29
cgtctgtcca tcccacttaa a                                                 21

<210> SEQ ID NO 30
<211> LENGTH: 24
<212> TYPE: DNA
<213> ORGANISM: Artificial Sequence
<220> FEATURE:
<223> OTHER INFORMATION: OXA48-HEX
```

```
<400> SEQUENCE: 30
tagcttgatc gccctcgatt tggg                                        24

<210> SEQ ID NO 31
<211> LENGTH: 19
<212> TYPE: DNA
<213> ORGANISM: Artificial Sequence
<220> FEATURE:
<223> OTHER INFORMATION: CMY F'

<400> SEQUENCE: 31
tccagcgtta ttgatatgg                                              19

<210> SEQ ID NO 32
<211> LENGTH: 18
<212> TYPE: DNA
<213> ORGANISM: Artificial Sequence
<220> FEATURE:
<223> OTHER INFORMATION: CMY R'

<400> SEQUENCE: 32
catctcccag cctaatcc                                               18

<210> SEQ ID NO 33
<211> LENGTH: 21
<212> TYPE: DNA
<213> ORGANISM: Artificial Sequence
<220> FEATURE:
<223> OTHER INFORMATION: CMY-TxR

<400> SEQUENCE: 33
acatatcgcc aatacgccag t                                           21

<210> SEQ ID NO 34
<211> LENGTH: 19
<212> TYPE: DNA
<213> ORGANISM: Artificial Sequence
<220> FEATURE:
<223> OTHER INFORMATION: NDM F'

<400> SEQUENCE: 34
tttgatcgtc agggatggc                                              19

<210> SEQ ID NO 35
<211> LENGTH: 21
<212> TYPE: DNA
<213> ORGANISM: Artificial Sequence
<220> FEATURE:
<223> OTHER INFORMATION: NDM R'

<400> SEQUENCE: 35
caggttgatc tcctgcttga t                                           21

<210> SEQ ID NO 36
<211> LENGTH: 22
<212> TYPE: DNA
<213> ORGANISM: Artificial Sequence
<220> FEATURE:
<223> OTHER INFORMATION: NDM-HEX

<400> SEQUENCE: 36
agaccgccca gatcctcaac tg                                          22
```

```
<210> SEQ ID NO 37
<211> LENGTH: 21
<212> TYPE: DNA
<213> ORGANISM: Artificial Sequence
<220> FEATURE:
<223> OTHER INFORMATION: KPC F'

<400> SEQUENCE: 37
cgctaaactc gaacaggact t                                              21

<210> SEQ ID NO 38
<211> LENGTH: 21
<212> TYPE: DNA
<213> ORGANISM: Artificial Sequence
<220> FEATURE:
<223> OTHER INFORMATION: KPC R'

<400> SEQUENCE: 38
taacttacag ttgcgcctga g                                              21

<210> SEQ ID NO 39
<211> LENGTH: 24
<212> TYPE: DNA
<213> ORGANISM: Artificial Sequence
<220> FEATURE:
<223> OTHER INFORMATION: KPC-FAM

<400> SEQUENCE: 39
atcggtgtgt acgcgatgga tacc                                           24

<210> SEQ ID NO 40
<211> LENGTH: 19
<212> TYPE: DNA
<213> ORGANISM: Artificial Sequence
<220> FEATURE:
<223> OTHER INFORMATION: VIM F'

<400> SEQUENCE: 40
cattcgaccg acaacttag                                                 19

<210> SEQ ID NO 41
<211> LENGTH: 17
<212> TYPE: DNA
<213> ORGANISM: Artificial Sequence
<220> FEATURE:
<223> OTHER INFORMATION: VIM R'

<400> SEQUENCE: 41
cgtgcgtgac aactcat                                                   17

<210> SEQ ID NO 42
<211> LENGTH: 24
<212> TYPE: DNA
<213> ORGANISM: Artificial Sequence
<220> FEATURE:
<223> OTHER INFORMATION: VIM-TEX

<400> SEQUENCE: 42
tgtgctctat ggtggttgtg cgat                                           24

<210> SEQ ID NO 43
<211> LENGTH: 21
<212> TYPE: DNA
<213> ORGANISM: Artificial Sequence
<220> FEATURE:
<223> OTHER INFORMATION: DHA F'
```

<400> SEQUENCE: 43
tgcgtacggt tatgagaaca a                                        21

<210> SEQ ID NO 44
<211> LENGTH: 18
<212> TYPE: DNA
<213> ORGANISM: Artificial Sequence
<220> FEATURE:
<223> OTHER INFORMATION: DHA R'

<400> SEQUENCE: 44
cccagcgcag catatctt                                            18

<210> SEQ ID NO 45
<211> LENGTH: 24
<212> TYPE: DNA
<213> ORGANISM: Artificial Sequence
<220> FEATURE:
<223> OTHER INFORMATION: DHA-FAM

<400> SEQUENCE: 45
atgcggaatc ttacggcgtg aaat                                     24

<210> SEQ ID NO 46
<211> LENGTH: 21
<212> TYPE: DNA
<213> ORGANISM: Artificial Sequence
<220> FEATURE:
<223> OTHER INFORMATION: IMP F'

<400> SEQUENCE: 46
acgtagtggt ttggttacct g                                        21

<210> SEQ ID NO 47
<211> LENGTH: 22
<212> TYPE: DNA
<213> ORGANISM: Artificial Sequence
<220> FEATURE:
<223> OTHER INFORMATION: IMP R'

<400> SEQUENCE: 47
aagcttctaa atttgcgtca cc                                       22

<210> SEQ ID NO 48
<211> LENGTH: 24
<212> TYPE: DNA
<213> ORGANISM: Artificial Sequence
<220> FEATURE:
<223> OTHER INFORMATION: IMP-TYE705

<400> SEQUENCE: 48
tttgttaaac cggacggtct tggt                                     24

<210> SEQ ID NO 49
<211> LENGTH: 201
<212> TYPE: DNA
<213> ORGANISM: Artificial Sequence
<220> FEATURE:
<223> OTHER INFORMATION: MOX

<400> SEQUENCE: 49
aaccgggaga gcggggccag cgtcagcgag cagaccctgt tcgagatagg atccgtgagc    60
aagaccctga ctgcgaccct gggggcctat gcggtggtca agggagcgat gcagctggat   120

```
gacaaggcga gccggcacgc gccctggctc aagggatccg tctttgacag catcaccatg    180
ggggagcttg ccacctacag c                                              201

<210> SEQ ID NO 50
<211> LENGTH: 240
<212> TYPE: DNA
<213> ORGANISM: Artificial Sequence
<220> FEATURE:
<223> OTHER INFORMATION: FOX

<400> SEQUENCE: 50
ggggatggcg gtcgccgtgc tgaaagatgg caaggcccac tatttcaact atggggttgc    60
caaccgcgag agtggtcagc gcgtcagcga gcagaccctg ttcgagattg gctcggtcag    120
caagaccctg accgcgaccc tcggtgccta tgctgcggtc aagggggggct ttgagctgga    180 tgacaaggtg agccagcacg ccccctggct caaaggttcc gcctttgatg gtgtgaccat    240

<210> SEQ ID NO 51
<211> LENGTH: 220
<212> TYPE: DNA
<213> ORGANISM: Artificial Sequence
<220> FEATURE:
<223> OTHER INFORMATION: EBC

<400> SEQUENCE: 51
ggaccgttac gccgctgatg aaagcgcagg ccattccggg tatggcggtg gcggtgattt    60
atgagggtca gccgcactac ttcaccttcg gtaaagccga tgttgcggcg aacaaacctg    120
tcactccaca aaccttgttc gaactgggtt ctataagtaa aaccttcacc ggcgtactcg    180
gtggcgatgc cattgctcgc ggtgaaatat cgctgggcga                          220

<210> SEQ ID NO 52
<211> LENGTH: 220
<212> TYPE: DNA
<213> ORGANISM: Artificial Sequence
<220> FEATURE:
<223> OTHER INFORMATION: DHA

<400> SEQUENCE: 52
gactgcacgg atcctggcac cgctggggtt atctcacacc tttattactg tgccggaaag    60
tgcgcaaagc cagtatgcgt acggttatga gaacaaaaaa ccggtccgcg tgtcgccggg    120
acagcttgat gcggaatctt acggcgtgga atccgcctca aaagatatgc tgcgctgggc    180
ggaaatgaat atggagccgt cacgggccgg taatgcggat                          220

<210> SEQ ID NO 53
<211> LENGTH: 260
<212> TYPE: DNA
<213> ORGANISM: Artificial Sequence
<220> FEATURE:
<223> OTHER INFORMATION: CMY

<400> SEQUENCE: 53
gcctgtacac gtttctccgg gacaacttga cgccgaagcc tatggcgtga atccagcgt     60 tattgatatg gcccgctggg ttcaggtcaa catggacgcc agccgcgttc aggagaaaac    120
gctccagcag ggcattgcgc ttgcgcagtc tcgctactgg cgtattggcg atatgtacca    180
gggattaggc tgggagatgc tgaactggcc gctgaaagct gattcgatca tcaacggtag    240
cgacagcaaa gtggcattgg                                                260
```

```
<210> SEQ ID NO 54
<211> LENGTH: 150
<212> TYPE: DNA
<213> ORGANISM: Artificial Sequence
<220> FEATURE:
<223> OTHER INFORMATION: ACC

<400> SEQUENCE: 54
gagagcaaaa ttaaagacac cgttgatgac ctgatccagc cgctgatgca gaagaataat      60
attcccggta tgtcggtcgc agtgaccgtc aacggtaaaa actacattta taactatggg     120
ttagcggcaa aacagcctca gcagccggtt                                      150

<210> SEQ ID NO 55
<211> LENGTH: 270
<212> TYPE: DNA
<213> ORGANISM: Artificial Sequence
<220> FEATURE:
<223> OTHER INFORMATION: IC

<400> SEQUENCE: 55
agcttgttgg tggggtaacg gctcaccaag gcgacgatcc ctagctggtc tgagaggatg      60
accagccaca ctggaactga gacacggtcc agactcctac gggaggcagc agtggggaat     120
attgcacaat gggcgcaagc ctgatgcagc catgccgcgt gtatgaagaa ggccttcggg     180
ttgtaaagta ctttcagcgg ggaggaaggg agtaaagtta ataccttgc tcattgacgt      240 tacccgcaga agaagcaccg gctaactccg                                      270

<210> SEQ ID NO 56
<211> LENGTH: 321
<212> TYPE: DNA
<213> ORGANISM: Artificial Sequence
<220> FEATURE:
<223> OTHER INFORMATION: CTX-M-14

<400> SEQUENCE: 56
cgtttcgtct ggatcgcact gaacctacgc tgaataccgc cattcccggc gacccgagag      60
acaccaccac gccgcgggcg atggcgcaga cgttgcgtca gcttacgctg ggtcatgcgc     120
tgggcgaaac ccagcggggcg cagttggtga cgtggctcaa aggcaatacg accggcgcag    180
ccagcattcg ggccggctta ccgacgtcgt ggactgtggg tgataagacc ggcagcggcg     240
actacggcac caccaatgat attgcggtga tctggccgca gggtcgtgcg ccgctggttc     300
tggtgaccta ttttacccag c                                               321

<210> SEQ ID NO 57
<211> LENGTH: 121
<212> TYPE: DNA
<213> ORGANISM: Artificial Sequence
<220> FEATURE:
<223> OTHER INFORMATION: CTX-M-15

<400> SEQUENCE: 57
ccgtcacgct gttgttagga agtgtgccgc tgtatgcgca acggcggac gtacagcaaa       60 aacttgccga attagagcgg cagtcgggag gcagactggg tgtggcattg attaacacag     120
c                                                                     121

<210> SEQ ID NO 58
<211> LENGTH: 553
<212> TYPE: DNA
<213> ORGANISM: Artificial Sequence
```

<220> FEATURE:
<223> OTHER INFORMATION: OXA

<400> SEQUENCE: 58

```
aatcacaggg cgtagttgtg ctctggaatg agaataagca gcaaggattt accaataatc    60
ttaaacgggc gaaccaagca tttttacccg catctacctt taaaattccc aatagcttga   120
tcgccctcga tttgggcgtg gttaaggatg aacaccaagt ctttaagtgg gatggacaga   180
cgcgcgatat cgccacttgg aatcgcgatc ataatctaat caccgcgatg aaatattcag   240
ttgtgcctgt ttatcaagaa tttgcccgcc aaattggcga ggcacgtatg agcaagatgc   300
tacatgcttt cgattatggt aatgaggaca tttcgggcaa tgtagacagt ttctggctcg   360
acggtggtat tcgaatttcg gccacggagc aaatcagctt tttaagaaag ctgtatcaca   420
ataagttaca cgtatcggag cgcagccagc gtattgtcaa acaagccatg ctgaccgaag   480
ccaatggtga ctaattattc gggctaaaac tggatactcg actagaatcg aacctaagat   540
tggctggctg ggt                                                      553
```

<210> SEQ ID NO 59
<211> LENGTH: 270
<212> TYPE: DNA
<213> ORGANISM: Artificial Sequence
<220> FEATURE:
<223> OTHER INFORMATION: IC

<400> SEQUENCE: 59

```
cggagttagc cggtgcttct tctgcgggta acgtcaatga gcaaaggtat taactttact    60
cccttcctcc ccgctgaaag tactttacaa cccgaaggcc ttcttcatac acgcggcatg   120
gctgcatcag gcttgcgccc attgtgcaat attccccact gctgcctccc gtaggagtct   180
ggaccgtgtc tcagttccag tgtggctggt catcctctca gaccagctag ggatcgtcgc   240
cttggtgagc cgttaccccca ccaacaagct                                   270
```

<210> SEQ ID NO 60
<211> LENGTH: 260
<212> TYPE: DNA
<213> ORGANISM: Artificial Sequence
<220> FEATURE:
<223> OTHER INFORMATION: CMY

<400> SEQUENCE: 60

```
gcctgtacac gtttctccgg gacaacttga cgccgaagcc tatggcgtga atccagcgt     60
tattgatatg gcccgctggg ttcaggtcaa catggacgcc agccgcgttc aggagaaaac   120
gctccagcag ggcattgcgc ttgcgcagtc tcgctactgg cgtattggcg atatgtacca   180
gggattaggc tgggagatgc tgaactggcc gctgaaagct gattcgatca tcaacggtag   240
cgacagcaaa gtggcattgg                                               260
```

<210> SEQ ID NO 61
<211> LENGTH: 263
<212> TYPE: DNA
<213> ORGANISM: Artificial Sequence
<220> FEATURE:
<223> OTHER INFORMATION: NDM

<400> SEQUENCE: 61

```
ggcgaaagtc aggctgtgtt gcgccgcaac catcccctct tgcggggcaa gctggttcga    60
caacgcattg gcataagtcg caatccccgc cgcatgcagc gcgtccatac cgcccatctt   120
```

| | |
|---|---|
| gtcctgatgc gcgtgagtca ccaccgccag cgcgaccggc aggttgatct cctgcttgat | 180 |
| ccagttgagg atctgggcgg tctggtcatc ggtccaggcg gtatcgacca ccagcacgcg | 240 |
| gccgccatcc ctgacgatca aac | 263 |

<210> SEQ ID NO 62
<211> LENGTH: 209
<212> TYPE: DNA
<213> ORGANISM: Artificial Sequence
<220> FEATURE:
<223> OTHER INFORMATION: KPC

<400> SEQUENCE: 62

| | |
|---|---|
| gtatcgccgt ctagttctgc tgtcttgtct ctcatggccg ctggctggct tttctgccac | 60 |
| cgcgctgacc aacctcgtcg cggaaccatt cgctaaactc gaacaggact ttggcggctc | 120 |
| catcggtgtg tacgcgatgg ataccggctc aggcgcaact gtaagttacc gcgctgagga | 180 |
| gcgcttccca ctgtgcagct cattcaagg | 209 |

<210> SEQ ID NO 63
<211> LENGTH: 292
<212> TYPE: DNA
<213> ORGANISM: Artificial Sequence
<220> FEATURE:
<223> OTHER INFORMATION: VIM

<400> SEQUENCE: 63

| | |
|---|---|
| ccattcagcc agatcggcat cggccacgtt ccccgcagac gtgcgtgaca actcatgaat | 60 |
| cgcacaacca ccatagagca cactcgcaga cgggacgtac acaactaagt tgtcggtcga | 120 |
| atgcgcagca ccaggataga agagttctac tggaccgaag cgcactgcgt ccccgctcga | 180 |
| gtccttctag agagtgcgtg ggaatctcgt tcccctctac ctcggctagc cggcgtgtcg | 240 |
| acggtgatgc gtacgttgcc accccagccg cccgaaggac atcaacgccg cc | 292 |

<210> SEQ ID NO 64
<211> LENGTH: 220
<212> TYPE: DNA
<213> ORGANISM: Artificial Sequence
<220> FEATURE:
<223> OTHER INFORMATION: DHA

<400> SEQUENCE: 64

| | |
|---|---|
| gactgcacgg atcctggcac cgctggggtt atctcacacc tttattactg tgccggaaag | 60 |
| tgcgcaaagc cagtatgcgt acggttatga gaacaaaaaa ccggtccgcg tgtcgccggg | 120 |
| acagcttgat gcggaatctt acggcgtgaa atccgcctca aaagatatgc tgcgctgggc | 180 |
| ggaaatgaat atggagccgt cacgggccgg taatgcggat | 220 |

<210> SEQ ID NO 65
<211> LENGTH: 270
<212> TYPE: DNA
<213> ORGANISM: Artificial Sequence
<220> FEATURE:
<223> OTHER INFORMATION: IC

<400> SEQUENCE: 65

| | |
|---|---|
| cggagttagc cggtgcttct tctgcgggta acgtcaatga gcaaaggtat taactttact | 60 |
| cccttcctcc ccgctgaaag tactttacaa cccgaaggcc ttcttcatac acgcggcatg | 120 |
| gctgcatcag gcttgcgccc attgtgcaat attccccact gctgcctccc gtaggagtct | 180 |

```
ggaccgtgtc tcagttccag tgtggctggt catcctctca gaccagctag ggatcgtcgc    240
cttggtgagc cgttacccca ccaacaagct                                     270
```

<210> SEQ ID NO 66
<211> LENGTH: 177
<212> TYPE: DNA
<213> ORGANISM: Artificial Sequence
<220> FEATURE:
<223> OTHER INFORMATION: IMP

<400> SEQUENCE: 66

```
gcggagttag ttattggcta gttaaaaata aaattgaagt tttttatccc ggcccggggc     60
acactcaaga taacgtagtg gtttggttac ctgaaaagaa aattttattc ggtggttgtt    120
ttgttaaacc ggacggtctt grvgtaattt gggtgacgca aatttagaag cttggcc       177
```

<210> SEQ ID NO 67
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 67

```
tggccagaac tgacaggcaa a                                               21
```

<210> SEQ ID NO 68
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 68

```
tttctcctga acgtggctgg c                                               21
```

<210> SEQ ID NO 69
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 69

```
acgctaactc cagcattggt ctgt                                            24
```

<210> SEQ ID NO 70
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 70

```
ccgtcacgct gttgttagg                                                  19
```

<210> SEQ ID NO 71
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 71

```
gctgtgttaa tcaatgccac ac                                              22
```

<210> SEQ ID NO 72
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 72
aacttgccga attagagcrg cagt                                          24

<210> SEQ ID NO 73
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 73
cgtttcgtct ggatcgcac                                                19

<210> SEQ ID NO 74
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 74
gctgggtaaa ataggtcacc                                               20

<210> SEQ ID NO 75
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 75
tatcattggt ggtgccgtag tcgc                                          24

<210> SEQ ID NO 76
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 76
gagaggatga ycagccacac                                               20

<210> SEQ ID NO 77
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 77
cgcccattgt scaatattcc                                               20

<210> SEQ ID NO 78
<211> LENGTH: 24
<212> TYPE: DNA
<213> ORGANISM: Artificial Sequence
<220> FEATURE:
<223> OTHER INFORMATION: PRIMER/PROBE

```
<400> SEQUENCE: 78
tgagacacgg tccagactcc tacg                                       24

<210> SEQ ID NO 79
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 79
aatcacaggg cgtagttgtg                                            20

<210> SEQ ID NO 80
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 80
acccaccagc caatcttagg                                            20

<210> SEQ ID NO 81
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 81
tagcttgatc gccctcgatt tggg                                       24

<210> SEQ ID NO 82
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 82
gcggagttaa ctattggcta g                                          21

<210> SEQ ID NO 83
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 83
ggccaagctt ctatatttgc g                                          21

<210> SEQ ID NO 84
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 84
ttrttyggtg gttgytttrt taa                                        23
```

```
<210> SEQ ID NO 85
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 85
gcggagttar ytattggcta g                                              21

<210> SEQ ID NO 86
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 86
ggccaagcyt ctawatttgc g                                              21

<210> SEQ ID NO 87
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 87
ccggacggtc ttggtaattt gggt                                           24

<210> SEQ ID NO 88
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 88
ccgtacggtt taggcaattt gggt                                           24

<210> SEQ ID NO 89
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 89
ggcggcgttg atgtccttcg                                                20

<210> SEQ ID NO 90
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 90
ccattcagcc agatcggcat c                                              21

<210> SEQ ID NO 91
<211> LENGTH: 23
<212> TYPE: DNA
<213> ORGANISM: Artificial Sequence
<220> FEATURE:
<223> OTHER INFORMATION: PRIMER/PROBE
```

<400> SEQUENCE: 91
agctcttcta tcctggtgct gcg                                              23

<210> SEQ ID NO 92
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 92
aactttcaca ggtgtgctgg gt                                               22

<210> SEQ ID NO 93
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 93
ccgtacgcat actggctttg c                                                21

<210> SEQ ID NO 94
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 94
aaaccgggcg atatgcgtct gtat                                             24

<210> SEQ ID NO 95
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 95
gtatcgccgt ctagttctgc                                                  20

<210> SEQ ID NO 96
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 96
ccttgaatga gctgcacagt gg                                               22

<210> SEQ ID NO 97
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 97
tcgtcgcgga accattcgct aaa                                              23

```
<210> SEQ ID NO 98
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 98
gtttgatcgt cagggatggc                                               20

<210> SEQ ID NO 99
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 99
ggcgaaagtc aggctgtg                                                 18

<210> SEQ ID NO 100
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 100
catcaggaca agatgggcgg tatg                                          24

<210> SEQ ID NO 101
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 101
gctgctcaag gagcacagga t                                             21

<210> SEQ ID NO 102
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 102
cacattgaca taggtgtggt gc                                            22

<210> SEQ ID NO 103
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 103
aggatggcaa ggcccactat ttca                                          24

<210> SEQ ID NO 104
<211> LENGTH: 21
<212> TYPE: DNA
<213> ORGANISM: Artificial Sequence
<220> FEATURE:
<223> OTHER INFORMATION: PRIMER/PROBES
```

<400> SEQUENCE: 104
aacagcctca gcagccggtt a                                              21

<210> SEQ ID NO 105
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 105
ttcgccgcaa tcatccctag c                                              21

<210> SEQ ID NO 106
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 106
agccattacg ttccagagtt gcgt                                           24

<210> SEQ ID NO 107
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 107
gccgaggctt acgggatcaa g                                              21

<210> SEQ ID NO 108
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 108
caaagcgcgt aaccggattg g                                              21

<210> SEQ ID NO 109
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 109
tctgctgaag tttrycgagg cmaa                                           24

<210> SEQ ID NO 110
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 110
aactttcaca ggtgtgctgg gt                                             22

```
<210> SEQ ID NO 111
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 111
ccgtacgcat actggctttg c                                              21

<210> SEQ ID NO 112
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 112
aaaccgggcg atatgcgtct gtat                                           24

<210> SEQ ID NO 113
<211> LENGTH: 29
<212> TYPE: DNA
<213> ORGANISM: Artificial Sequence
<220> FEATURE:
<223> OTHER INFORMATION: PRIMER/PROBE

<400> SEQUENCE: 113
ctgggttcta taagtaaaac cttcaccgg                                      29

<210> SEQ ID NO 114
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 114
cttccactgc ggctgccagt t                                              21

<210> SEQ ID NO 115
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 115
gatgccattg cycgsggtga aat                                            23

<210> SEQ ID NO 116
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 116
ccgaagccta tggcgtgaaa tcc                                            23

<210> SEQ ID NO 117
<211> LENGTH: 19
<212> TYPE: DNA
<213> ORGANISM: Artificial Sequence
<220> FEATURE:
<223> OTHER INFORMATION: PRIMER/PROBE
```

-continued

```
<400> SEQUENCE: 117
gcaatgccct gctggagcg                                                    19

<210> SEQ ID NO 118
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 118
atgttggcct gaacccagcg                                                   20

<210> SEQ ID NO 119
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 119
agcacataca gaatatgtcc ctgc                                              24

<210> SEQ ID NO 120
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 120
acctgttaac caacctactt gaggg                                             25

<210> SEQ ID NO 121
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 121
ttgcaagacg gactggctta gacc                                              24

<210> SEQ ID NO 122
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 122
cctgatcgga ttggagaacc                                                   20

<210> SEQ ID NO 123
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 123
ctacctcttg aataggcgta acc                                               23
```

```
<210> SEQ ID NO 124
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 124
acgtcgcgca agttcctgat agac                                          24

<210> SEQ ID NO 125
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 125
tagtgactgc taatccaaat cacag                                         25

<210> SEQ ID NO 126
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 126
gcacgagcaa gatcattacc atagc                                         25

<210> SEQ ID NO 127
<211> LENGTH: 27
<212> TYPE: DNA
<213> ORGANISM: Artificial Sequence
<220> FEATURE:
<223> OTHER INFORMATION: PRIMER/PROBE

<400> SEQUENCE: 127
agttatccaa caaggccaaa ctcaaca                                       27

<210> SEQ ID NO 128
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 128
aatcacaggg cgtagttgtg                                               20

<210> SEQ ID NO 129
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 129
acccaccagc caatcttagg                                               20

<210> SEQ ID NO 130
<211> LENGTH: 24
<212> TYPE: DNA
<213> ORGANISM: Artificial Sequence
<220> FEATURE:
<223> OTHER INFORMATION: PRIMER/PROBE
```

```
<400> SEQUENCE: 130
tagcttgatc gccctcgatt tggg                                          24

<210> SEQ ID NO 131
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 131
gtgggatgga agccacg                                                  18

<210> SEQ ID NO 132
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 132
cacttgcggg tctacagc                                                 18

<210> SEQ ID NO 133
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 133
ttactttggg cgaagccatg caag                                          24

<210> SEQ ID NO 134
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 134
cacctatggt aatgctcttg c                                             21

<210> SEQ ID NO 135
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 135
ctggaactgc tgacaatgcc                                               20

<210> SEQ ID NO 136
<211> LENGTH: 30
<212> TYPE: DNA
<213> ORGANISM: Artificial Sequence
<220> FEATURE:
<223> OTHER INFORMATION: PRIMER/PROBE

<400> SEQUENCE: 136
tgggagaaag atatgacttt aggtgaggca                                    30
```

```
<210> SEQ ID NO 137
<211> LENGTH: 18
<212> TYPE: DNA
<213> ORGANISM: Artificial Sequence
<220> FEATURE:
<223> OTHER INFORMATION: PRIMER/PROBES

<400> SEQUENCE: 137
ccgtgtatgt tcagctat                                              18

<210> SEQ ID NO 138
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 138
cttatccatc acgccttt                                              18

<210> SEQ ID NO 139
<211> LENGTH: 26
<212> TYPE: DNA
<213> ORGANISM: Artificial Sequence
<220> FEATURE:
<223> OTHER INFORMATION: PRIMER/PROBES

<400> SEQUENCE: 139
tatgatgtcg ataccgccaa atacca                                     26

<210> SEQ ID NO 140
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 140
ctgtatgtca gcgatcat                                              18

<210> SEQ ID NO 141
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 141
gatgccagtt tgcttatcc                                             19

<210> SEQ ID NO 142
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 142
aagtctgggt gagaacggtg tctat                                      25

<210> SEQ ID NO 143
<211> LENGTH: 19
<212> TYPE: DNA
<213> ORGANISM: Artificial Sequence
<220> FEATURE:
<223> OTHER INFORMATION: PRIMER/PROBE
```

<400> SEQUENCE: 143
cagtcagtat gcgagtttc                                            19

<210> SEQ ID NO 144
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 144
aaaattcgcc aagccatc                                             18

<210> SEQ ID NO 145
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 145
tgcataagcc agtgcgtttt tatat                                     25

<210> SEQ ID NO 146
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 146
agatcagttg ggtgcacg                                             18

<210> SEQ ID NO 147
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 147
tgcttaatca gtgaggcacc                                           20

<210> SEQ ID NO 148
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 148
atgaagccat accaaacgac gagc                                      24

<210> SEQ ID NO 149
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 149
ctggagcgaa agatccacta                                           20

```
<210> SEQ ID NO 150
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 150
atcgtccacc atccactg                                                 18

<210> SEQ ID NO 151
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 151
ccagatcggc gacaacgtca cc                                            22

<210> SEQ ID NO 152
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 152
tggccagaac tgacaggcaa a                                             21

<210> SEQ ID NO 153
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 153
tttctcctga acgtggctgg c                                             21

<210> SEQ ID NO 154
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 154
acgctaactc cagcattggt ctgt                                          24

<210> SEQ ID NO 155
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 155
ccgtcacgct gttgttagg                                                19

<210> SEQ ID NO 156
<211> LENGTH: 22
<212> TYPE: DNA
<213> ORGANISM: Artificial Sequence
<220> FEATURE:
<223> OTHER INFORMATION: PRIMER/PROBE
```

```
<400> SEQUENCE: 156
gctgtgttaa tcaatgccac ac                                          22

<210> SEQ ID NO 157
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 157
aacttgccga attagagcrg cagt                                        24

<210> SEQ ID NO 158
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 158
cgtttcgtct ggatcgcac                                              19

<210> SEQ ID NO 159
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 159
gctgggtaaa ataggtcacc                                             20

<210> SEQ ID NO 160
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 160
tatcattggt ggtgccgtag tcgc                                        24

<210> SEQ ID NO 161
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 161
gagaggatga ycagccacac                                             20

<210> SEQ ID NO 162
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 162
cgcccattgt scaatattcc                                             20
```

```
<210> SEQ ID NO 163
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 163
tgagacacgg tccagactcc tacg                                            24

<210> SEQ ID NO 164
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 164
aatcacaggg cgtagttgtg                                                 20

<210> SEQ ID NO 165
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 165
acccaccagc caatcttagg                                                 20

<210> SEQ ID NO 166
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 166
tagcttgatc gccctcgatt tggg                                            24

<210> SEQ ID NO 167
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 167
gcggagttaa ctattggcta g                                               21

<210> SEQ ID NO 168
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 168
ggccaagctt ctatatttgc g                                               21

<210> SEQ ID NO 169
<211> LENGTH: 23
<212> TYPE: DNA
<213> ORGANISM: Artificial Sequence
<220> FEATURE:
<223> OTHER INFORMATION: PRIMER/PROBE
```

<400> SEQUENCE: 169
ttrttyggtg gttgytttrt taa                                            23

<210> SEQ ID NO 170
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 170
gcggagttar ytattggcta g                                              21

<210> SEQ ID NO 171
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 171
ggccaagcyt ctawatttgc g                                              21

<210> SEQ ID NO 172
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 172
ccggacggtc ttggtaattt gggt                                           24

<210> SEQ ID NO 173
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 173
ccgtacggtt taggcaattt gggt                                           24

<210> SEQ ID NO 174
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 174
ggcggcgttg atgtccttcg                                                20

<210> SEQ ID NO 175
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 175
ccattcagcc agatcggcat c                                              21

```
<210> SEQ ID NO 176
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 176
agctcttcta tcctggtgct gcg                                            23

<210> SEQ ID NO 177
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 177
gagaggatga ycagccacac                                                20

<210> SEQ ID NO 178
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 178
cgcccattgt scaatattcc                                                20

<210> SEQ ID NO 179
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 179
tgagacacgg tccagactcc tacg                                           24

<210> SEQ ID NO 180
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 180
aactttcaca ggtgtgctgg gt                                             22

<210> SEQ ID NO 181
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 181
ccgtacgcat actggctttg c                                              21

<210> SEQ ID NO 182
<211> LENGTH: 24
<212> TYPE: DNA
<213> ORGANISM: Artificial Sequence
<220> FEATURE:
<223> OTHER INFORMATION: PRIMER/PROBE
```

-continued

```
<400> SEQUENCE: 182
aaaccgggcg atatgcgtct gtat                                          24

<210> SEQ ID NO 183
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 183
gtatcgccgt ctagttctgc                                               20

<210> SEQ ID NO 184
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 184
ccttgaatga gctgcacagt gg                                            22

<210> SEQ ID NO 185
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 185
tcgtcgcgga accattcgct aaa                                           23

<210> SEQ ID NO 186
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 186
gtttgatcgt cagggatggc                                               20

<210> SEQ ID NO 187
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 187
ggcgaaagtc aggctgtg                                                 18

<210> SEQ ID NO 188
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 188
catcaggaca agatgggcgg tatg                                          24
```

```
<210> SEQ ID NO 189
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 189
gagaggatga ycagccacac                                              20

<210> SEQ ID NO 190
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 190
cgcccattgt scaatattcc                                              20

<210> SEQ ID NO 191
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 191
tgagacacgg tccagactcc tacg                                         24

<210> SEQ ID NO 192
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 192
gctgctcaag gagcacagga t                                            21

<210> SEQ ID NO 193
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 193
cacattgaca taggtgtggt gc                                           22

<210> SEQ ID NO 194
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 194
aggatggcaa ggcccactat ttca                                         24

<210> SEQ ID NO 195
<211> LENGTH: 21
<212> TYPE: DNA
<213> ORGANISM: Artificial Sequence
<220> FEATURE:
<223> OTHER INFORMATION: PRIMER/PROBE
```

<400> SEQUENCE: 195
aacagcctca gcagccggtt a                                        21

<210> SEQ ID NO 196
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 196
ttcgccgcaa tcatccctag c                                        21

<210> SEQ ID NO 197
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 197
agccattacg ttccagagtt gcgt                                     24

<210> SEQ ID NO 198
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 198
gccgaggctt acgggatcaa g                                        21

<210> SEQ ID NO 199
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 199
caaagcgcgt aaccggattg g                                        21

<210> SEQ ID NO 200
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 200
tctgctgaag tttrycgagg cmaa                                     24

<210> SEQ ID NO 201
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 201
gagaggatga ycagccacac                                          20

<210> SEQ ID NO 202
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 202
cgcccattgt scaatattcc                                                    20

<210> SEQ ID NO 203
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 203
tgagacacgg tccagactcc tacg                                               24

<210> SEQ ID NO 204
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 204
aactttcaca ggtgtgctgg gt                                                 22

<210> SEQ ID NO 205
<211> LENGTH: 21
<212> TYPE: DNA
<213> ORGANISM: Artificial Sequence
<220> FEATURE:
<223> OTHER INFORMATION: PRIMER/PROBE

<400> SEQUENCE: 205
ccgtacgcat actggctttg c                                                  21

<210> SEQ ID NO 206
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 206
aaaccgggcg atatgcgtct gtat                                               24

<210> SEQ ID NO 207
<211> LENGTH: 29
<212> TYPE: DNA
<213> ORGANISM: Artificial Sequence
<220> FEATURE:
<223> OTHER INFORMATION: PRIMER/PROBE

<400> SEQUENCE: 207
ctgggttcta taagtaaaac cttcaccgg                                          29

<210> SEQ ID NO 208
<211> LENGTH: 21
<212> TYPE: DNA
<213> ORGANISM: Artificial Sequence
<220> FEATURE:
<223> OTHER INFORMATION: PRIMER/PROBE

```
<400> SEQUENCE: 208
cttccactgc ggctgccagt t                                               21

<210> SEQ ID NO 209
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 209
gatgccattg cycgsggtga aat                                             23

<210> SEQ ID NO 210
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 210
ccgaagccta tggcgtgaaa tcc                                             23

<210> SEQ ID NO 211
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 211
gcaatgccct gctggagcg                                                  19

<210> SEQ ID NO 212
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 212
atgttggcct gaacccagcg                                                 20

<210> SEQ ID NO 213
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 213
gagaggatga ycagccacac                                                 20

<210> SEQ ID NO 214
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 214
cgcccattgt scaatattcc                                                 20
```

```
<210> SEQ ID NO 215
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 215
tgagacacgg tccagactcc tacg                                              24

<210> SEQ ID NO 216
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 216
agcacataca gaatatgtcc ctgc                                              24

<210> SEQ ID NO 217
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 217
acctgttaac caacctactt gaggg                                             25

<210> SEQ ID NO 218
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 218
ttgcaagacg gactggctta gacc                                              24

<210> SEQ ID NO 219
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 219
cctgatcgga ttggagaacc                                                   20

<210> SEQ ID NO 220
<211> LENGTH: 23
<212> TYPE: DNA
<213> ORGANISM: Artificial Sequence
<220> FEATURE:
<223> OTHER INFORMATION: PRIMER/PROBE

<400> SEQUENCE: 220
ctacctcttg aataggcgta acc                                               23

<210> SEQ ID NO 221
<211> LENGTH: 24
<212> TYPE: DNA
<213> ORGANISM: Artificial Sequence
<220> FEATURE:
<223> OTHER INFORMATION: PRIMER/PROBE
```

<400> SEQUENCE: 221
acgtcgcgca agttcctgat agac                                              24

<210> SEQ ID NO 222
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 222
tagtgactgc taatccaaat cacag                                             25

<210> SEQ ID NO 223
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 223
gcacgagcaa gatcattacc atagc                                             25

<210> SEQ ID NO 224
<211> LENGTH: 27
<212> TYPE: DNA
<213> ORGANISM: Artificial Sequence
<220> FEATURE:
<223> OTHER INFORMATION: PRIMER/PROBE

<400> SEQUENCE: 224
agttatccaa caaggccaaa ctcaaca                                           27

<210> SEQ ID NO 225
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 225
gagaggatga ycagccacac                                                   20

<210> SEQ ID NO 226
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 226
cgcccattgt scaatattcc                                                   20

<210> SEQ ID NO 227
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 227
tgagacacgg tccagactcc tacg                                              24

```
<210> SEQ ID NO 228
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 228
aatcacaggg cgtagttgtg                                                      20

<210> SEQ ID NO 229
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 229
acccaccagc caatcttagg                                                      20

<210> SEQ ID NO 230
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 230
tagcttgatc gccctcgatt tggg                                                 24

<210> SEQ ID NO 231
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 231
gtgggatgga aagccacg                                                        18

<210> SEQ ID NO 232
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 232
cacttgcggg tctacagc                                                        18

<210> SEQ ID NO 233
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 233
ttactttggg cgaagccatg caag                                                 24

<210> SEQ ID NO 234
<211> LENGTH: 21
<212> TYPE: DNA
<213> ORGANISM: Artificial Sequence
<220> FEATURE:
<223> OTHER INFORMATION: PRIMER/PROBE
```

```
<400> SEQUENCE: 234
cacctatggt aatgctcttg c                                          21

<210> SEQ ID NO 235
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 235
ctggaactgc tgacaatgcc                                            20

<210> SEQ ID NO 236
<211> LENGTH: 30
<212> TYPE: DNA
<213> ORGANISM: Artificial Sequence
<220> FEATURE:
<223> OTHER INFORMATION: PRIMER/PROBE

<400> SEQUENCE: 236
tgggagaaag atatgacttt aggtgaggca                                 30

<210> SEQ ID NO 237
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 237
gagaggatga ycagccacac                                            20

<210> SEQ ID NO 238
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 238
cgcccattgt scaatattcc                                            20

<210> SEQ ID NO 239
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 239
tgagacacgg tccagactcc tacg                                       24

<210> SEQ ID NO 240
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 240
agatcagttg ggtgcacg                                              18
```

```
<210> SEQ ID NO 241
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 241
tgcttaatca gtgaggcacc                                               20

<210> SEQ ID NO 242
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 242
atgaagccat accaaacgac gagc                                          24

<210> SEQ ID NO 243
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 243
ctggagcgaa agatccacta                                               20

<210> SEQ ID NO 244
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 244
atcgtccacc atccactg                                                 18

<210> SEQ ID NO 245
<211> LENGTH: 22
<212> TYPE: DNA
<213> ORGANISM: Artificial Sequence
<220> FEATURE:
<223> OTHER INFORMATION: PRIMER/PROBE

<400> SEQUENCE: 245
ccagatcggc gacaacgtca cc                                            22

<210> SEQ ID NO 246
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 246
gagaggatga ycagccacac                                               20

<210> SEQ ID NO 247
<211> LENGTH: 20
<212> TYPE: DNA
<213> ORGANISM: Artificial Sequence
<220> FEATURE:
<223> OTHER INFORMATION: PRIMER/PROBE
```

<400> SEQUENCE: 247
cgcccattgt scaatattcc 20

<210> SEQ ID NO 248
<211> LENGTH: 24
<212> TYPE: DNA
<213> ORGANISM: Artificial Sequence
<220> FEATURE:
<223> OTHER INFORMATION: PRIMER/PROBE

<400> SEQUENCE: 248
tgagacacgg tccagactcc tacg 24

<210> SEQ ID NO 249
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 249
ccgtgtatgt tcagctat 18

<210> SEQ ID NO 250
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 250
cttatccatc acgccttt 18

<210> SEQ ID NO 251
<211> LENGTH: 26
<212> TYPE: DNA
<213> ORGANISM: Artificial Sequence
<220> FEATURE:
<223> OTHER INFORMATION: PRIMER/PROBE

<400> SEQUENCE: 251
tatgatgtcg ataccgccaa atacca 26

<210> SEQ ID NO 252
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 252
ctgtatgtca gcgatcat 18

<210> SEQ ID NO 253
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 253
gatgccagtt tgcttatcc 19

```
<210> SEQ ID NO 254
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 254
aagtctgggt gagaacggtg tctat                                          25

<210> SEQ ID NO 255
<211> LENGTH: 19
<212> TYPE: DNA
<213> ORGANISM: Artificial Sequence
<220> FEATURE:
<223> OTHER INFORMATION: PRIMER/PROBE

<400> SEQUENCE: 255
cagtcagtat gcgagtttc                                                 19

<210> SEQ ID NO 256
<211> LENGTH: 18
<212> TYPE: DNA
<213> ORGANISM: Artificial Sequence
<220> FEATURE:
<223> OTHER INFORMATION: PRIMER/PROBE

<400> SEQUENCE: 256
aaaattcgcc aagccatc                                                  18

<210> SEQ ID NO 257
<211> LENGTH: 25
<212> TYPE: DNA
<213> ORGANISM: Artificial Sequence
<220> FEATURE:
<223> OTHER INFORMATION: PRIMER/PROBE

<400> SEQUENCE: 257
tgcataagcc agtgcgtttt tatat                                          25

<210> SEQ ID NO 258
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 258
gagaggatga ycagccacac                                                20

<210> SEQ ID NO 259
<211> LENGTH: 20
<212> TYPE: DNA
<213> ORGANISM: Artificial Sequence
<220> FEATURE:
<223> OTHER INFORMATION: PRIMER/PROBE

<400> SEQUENCE: 259
cgcccattgt scaatattcc                                                20

<210> SEQ ID NO 260
<211> LENGTH: 24
<212> TYPE: DNA
<213> ORGANISM: Artificial Sequence
<220> FEATURE:
<223> OTHER INFORMATION: PRIMER/PROBE
```

<400> SEQUENCE: 260
tgagacacgg tccagactcc tacg    24

<210> SEQ ID NO 261
<211> LENGTH: 462
<212> TYPE: DNA
<213> ORGANISM: Artificial Sequence
<220> FEATURE:
<223> OTHER INFORMATION: CONTROL MIX

<400> SEQUENCE: 261
tggccagaac tgacaggcaa acagtggcag ggtatccgcc tgctgcactt agccacctat    60
acggcaggcg gcctaccgct gcagatcccc gatgacgtta gggataaagc cgcattactg    120 cattttatc aaaactggca gccgcaatgg actccgggcg ctaagcgact ttacgctaac    180
tccagcattg gtctgtttgg cgcgctggcg gtgaaaccct caggaatgag ttacgaagag    240
gcaatgacca gacgcgtcct gcaaccatta aaactggcgc atacctggat tacggttccg    300
cagaacgaac aaaaagatta tgcctggggc tatcgcgaag ggaagcccgt acacgtttct    360
ccgggacaac ttgacgccga agcctatggc gtgaaatcca gcgttattga tatggcccgc    420
tgggttcagg ccaacatgga tgccagccac gttcaggaga aa    462

<210> SEQ ID NO 262
<211> LENGTH: 121
<212> TYPE: DNA
<213> ORGANISM: Artificial Sequence
<220> FEATURE:
<223> OTHER INFORMATION: CONTROL MIX

<400> SEQUENCE: 262
ccgtcacgct gttgttagga agtgtgccgc tgtatgcgca acggcggac gtacagcaaa    60 aacttgccga attagagcgg cagtcgggag gcagactggg tgtggcattg attaacacag    120
c    121

<210> SEQ ID NO 263
<211> LENGTH: 321
<212> TYPE: DNA
<213> ORGANISM: Artificial Sequence
<220> FEATURE:
<223> OTHER INFORMATION: CONTROL MIX

<400> SEQUENCE: 263
cgtttcgtct ggatcgcact gaacctacgc tgaataccgc cattcccggc gacccgagag    60
acaccaccac gccgcgggcg atggcgcaga cgttgcgtca gcttacgctg ggtcatgcgc    120
tgggcgaaac ccagcgggcg cagttggtga cgtggctcaa aggcaatacg accgcgcag    180 ccagcattcg ggccggctta ccgacgtcgt ggactgtggg tgataagacc ggcagcggcg    240
actacggcac caccaatgat attgcggtga tctggccgca gggtcgtgcg ccgctggttc    300
tggtgaccta ttttacccag c    321

<210> SEQ ID NO 264
<211> LENGTH: 84
<212> TYPE: DNA
<213> ORGANISM: Artificial Sequence
<220> FEATURE:
<223> OTHER INFORMATION: CONTROL MIX

<400> SEQUENCE: 264
gagaggatga ccagccacac tggaactgag acacggtcca gactcctacg ggaggcagca    60
gtggggaata ttgcacaatg ggcg    84

<210> SEQ ID NO 265
<211> LENGTH: 553
<212> TYPE: DNA
<213> ORGANISM: Artificial Sequence
<220> FEATURE:
<223> OTHER INFORMATION: CONTROL MIX

<400> SEQUENCE: 265
aatcacaggg cgtagttgtg ctctggaatg agaataagca gcaaggattt accaataatc    60
ttaaacgggc gaaccaagca tttttacccg catctacctt taaaattccc aatagcttga   120
tcgccctcga tttgggcgtg gttaaggatg aacaccaagt ctttaagtgg gatggacaga   180
cgcgcgatat cgccacttgg aatcgcgatc ataatctaat caccgcgatg aaatattcag   240
ttgtgcctgt ttatcaagaa tttgcccgcc aaattggcga ggcacgtatg agcaagatgc   300
tacatgcttt cgattatggt aatgaggaca tttcgggcaa tgtagacagt ttctggctcg   360
acggtggtat tcgaatttcg gccacggagc aaatcagctt tttaagaaag ctgtatcaca   420
ataagttaca cgtatcggag cgcagccagc gtattgtcaa acaagccatg ctgaccgaag   480
ccaatggtga ctatattatt cgggctaaaa ctggatactc gactagaatc gaacctaaga   540
ttggctggtg ggt    553

<210> SEQ ID NO 266
<211> LENGTH: 175
<212> TYPE: DNA
<213> ORGANISM: Artificial Sequence
<220> FEATURE:
<223> OTHER INFORMATION: CONTROL MIX

<400> SEQUENCE: 266
gcggagttag ttattggcta gttaaaaata aaattgaagt ttttttatccc ggcccggggc    60 acactcaaga taacgtagtg gtttggttac ctgaaaagaa aatttttattc ggtggttgtt   120 ttgttaaacc ggacggtctt ggtaatttgg gtgacgcaaa tttagaagct tggcc        175

<210> SEQ ID NO 267
<211> LENGTH: 297
<212> TYPE: DNA
<213> ORGANISM: Artificial Sequence
<220> FEATURE:
<223> OTHER INFORMATION: CONTROL MIX

<400> SEQUENCE: 267
ggcggcgttg atgtccttcg ggcggctggg gtggcaacgt acgcatcacc gtcgacacgc    60
cggctagccg aggtagaggg gaacgagatt cccacgcact ctctagaagg actctcatcg   120
agcggggacg cagtgcgctt cggtccagta gaactcttct atcctggtgc tgcgcattcg   180
accgacaact tagttgtgta cgtcccgtct gcgagtgtgc tctatggtgg ttgtgcgatt   240
catgagttgt cacgcacgtc tgcggggaac gtggccgatg ccgatctggc tgaatgg     297

<210> SEQ ID NO 268
<211> LENGTH: 84
<212> TYPE: DNA
<213> ORGANISM: Artificial Sequence
<220> FEATURE:
<223> OTHER INFORMATION: CONTROL MIX

<400> SEQUENCE: 268
gagaggatga ccagccacac tggaactgag acacggtcca gactcctacg ggaggcagca    60
gtggggaata ttgcacaatg ggcg    84

<210> SEQ ID NO 269
<211> LENGTH: 405
<212> TYPE: DNA
<213> ORGANISM: Artificial Sequence
<220> FEATURE:
<223> OTHER INFORMATION: CONTROL MIX

<400> SEQUENCE: 269
aactttcaca ggtgtgctgg gtgcggtttc tgtggcgaaa aaagagatgg cgctgaatga    60
tccggcggca aaataccagc cggagctggc tctgccgcag tggaagggga tcacattgct   120
ggatctggct acctataccg caggcggact gccgttacag gtgccggatg cggtaaaaag   180
ccgtgcggat ctgctgaatt tctatcagca gtggcagccg tcccggaaac cgggcgatat   240
gcgtctgtat gcaaacagca gtatcggcct gtttggtgct ctgaccgcaa acgcggcggg   300
gatgccgtat gagcagttgc tgactgcacg gatcctggca ccgctggggt tatctcacac   360
ctttattact gtgccggaaa gtgcgcaaag ccagtatgcg tacgg    405

<210> SEQ ID NO 270
<211> LENGTH: 209
<212> TYPE: DNA
<213> ORGANISM: Artificial Sequence
<220> FEATURE:
<223> OTHER INFORMATION: CONTROL MIX

<400> SEQUENCE: 270
gtatcgccgt ctagttctgc tgtcttgtct ctcatggccg ctggctggct tttctgccac    60
cgcgctgacc aacctcgtcg cggaaccatt cgctaaactc gaacaggact ttggcggctc   120
catcggtgtg tacgcgatgg ataccggctc aggcgcaact gtaagttacc gcgctgagga   180
gcgcttccca ctgtgcagct cattcaagg    209

<210> SEQ ID NO 271
<211> LENGTH: 263
<212> TYPE: DNA
<213> ORGANISM: Artificial Sequence
<220> FEATURE:
<223> OTHER INFORMATION: CONTROL MIX

<400> SEQUENCE: 271
gtttgatcgt cagggatggc ggccgcgtgc tggtggtcga taccgcctgg accgatgacc    60
agaccgccca gatcctcaac tggatcaagc aggagatcaa cctgccggtc gcgctggcgg   120
tggtgactca cgcgcatcag gacaagatgg gcggtatgga cgcgctgcat gcggcgggga   180
ttgcgactta tgccaatgcg ttgtcgaacc agcttgcccc gcaagagggg atggttgcgg   240
cgcaacacag cctgactttc gcc    263

<210> SEQ ID NO 272
<211> LENGTH: 84
<212> TYPE: DNA
<213> ORGANISM: Artificial Sequence
<220> FEATURE:
<223> OTHER INFORMATION: CONTROL MIX

<400> SEQUENCE: 272

```
gagaggatga ccagccacac tggaactgag acacggtcca gactcctacg ggaggcagca      60
gtggggaata ttgcacaatg ggcg                                              84
```

<210> SEQ ID NO 273
<211> LENGTH: 520
<212> TYPE: DNA
<213> ORGANISM: Artificial Sequence
<220> FEATURE:
<223> OTHER INFORMATION: CONTROL MIX

<400> SEQUENCE: 273

```
gctgctcaag gagcacagga tcccgggcat ggcggtggcc gtgctcaagg atggcaaggc      60
ccactatttc aattacgggg tggccaaccg ggagagcggg gccagcgtca gcagcagac     120 cctgttcgag ataggatccg tgagcaagac cctgactgcg accctggggg cctatgcggt     180
ggtcaaggga gcgatgcagc tggatgacaa ggcgagccgg cacgcgccct ggctcaaggg     240
atccgtcttt gacagcatca ccatggggga gcttgccacc tacagcgccg gaggcctgcc     300
actgcaattc cccgaggagg tggattcatc cgagaagatg cgcgcctact accgccagtg     360
ggcccctgtc tattcgccgg gctcccatcg ccagtactcc aaccccagca tagggctgtt     420
cggccacctg gcgcgagca gcctgaagca gccatttgcc cagttgatgg agcagaccct     480
gctgcccggg ctcggcatgc accacaccta tgtcaatgtg                            520
```

<210> SEQ ID NO 274
<211> LENGTH: 346
<212> TYPE: DNA
<213> ORGANISM: Artificial Sequence
<220> FEATURE:
<223> OTHER INFORMATION: CONTROL MIX

<400> SEQUENCE: 274

```
aacagcctca gcagccggtt acggaaaata cgttatttga agtgggttcg ctgagtaaaa      60
cgtttgctgc caccttggcg tcctatgcgc aggtgagcgg taagctgtct ttggatcaaa     120
gcgttagcca ttacgttcca gagttgcgtg gcagcagctt tgaccacgtt agcgtactca     180
atgtgggcac gcatacctca ggcctacagc tatttatgcc ggaagatatt aaaaatacca     240
cacagctgat ggcttatcta aaagcatgga aacctgccga tgcggctgga acccatcgcg     300
tttattccaa tatcggtact ggtttgctag ggatgattgc ggcgaa                    346
```

<210> SEQ ID NO 275
<211> LENGTH: 247
<212> TYPE: DNA
<213> ORGANISM: Artificial Sequence
<220> FEATURE:
<223> OTHER INFORMATION: CONTROL MIX

<400> SEQUENCE: 275

```
gccgaggctt acgggatcaa gaccggctcg gcggatctgc tgaagtttac cgaggccaac      60
atggggtatc agggagatgc cgcgctaaaa acgcggatcg cgctgaccca taccggtttc     120
tactcggtgg gagacatgac tcaggggctg ggttgggaga gctacgccta tccgttgacc     180
gagcaggcgc tgctggcggg caactccccg gcggtgagct tccaggccaa tccggttacg     240
cgctttg                                                               247
```

```
<210> SEQ ID NO 276
<211> LENGTH: 84
<212> TYPE: DNA
<213> ORGANISM: Artificial Sequence
<220> FEATURE:
<223> OTHER INFORMATION: CONTROL MIX

<400> SEQUENCE: 276
gagaggatga ccagccacac tggaactgag acacggtcca gactcctacg ggaggcagca    60
gtggggaata ttgcacaatg ggcg                                           84

<210> SEQ ID NO 277
<211> LENGTH: 405
<212> TYPE: DNA
<213> ORGANISM: Artificial Sequence
<220> FEATURE:
<223> OTHER INFORMATION: CONTROL MIX

<400> SEQUENCE: 277
aactttcaca ggtgtgctgg gtgcggtttc tgtggcgaaa aaagagatgg cgctgaatga    60
tccggcggca aaataccagc cggagctggc tctgccgcag tggaagggga tcacattgct   120
ggatctggct acctataccg caggcggact gccgttacag gtgccggatg cggtaaaaag   180
ccgtgcggat ctgctgaatt tctatcagca gtggcagccg tcccggaaac cgggcgatat   240
gcgtctgtat gcaaacagca gtatcggcct gtttggtgct ctgaccgcaa acgcggcggg   300
gatgccgtat gagcagttgc tgactgcacg gatcctggca ccgctggggt tatctcacac   360
ctttattact gtgccggaaa gtgcgcaaag ccagtatgcg tacgg                   405

<210> SEQ ID NO 278
<211> LENGTH: 302
<212> TYPE: DNA
<213> ORGANISM: Artificial Sequence
<220> FEATURE:
<223> OTHER INFORMATION: CONTROL MIX

<400> SEQUENCE: 278
tcggtaaagc cgatgttgcg gcgaacaaac ccgtcacccc gcaaaccctg tttgagctgg    60
gctctataag taaaaccttc accggcgtac tgggcggcga tgccattgcc cggggtgaaa   120
tagcgctggg cgatccggta gcaaaatact ggcctgagct cacgggcaag cagtggcagg   180
gcattcgcat gctggatctg caacctata ccgcaggcgg tctgccgtta caggtgccgg    240
atgaggtcac ggataccgcc tctctgctgc gcttttatca aaactggcag ccgcagtgga   300
ag                                                                  302

<210> SEQ ID NO 279
<211> LENGTH: 106
<212> TYPE: DNA
<213> ORGANISM: Artificial Sequence
<220> FEATURE:
<223> OTHER INFORMATION: CONTROL MIX

<400> SEQUENCE: 279
ccgaagccta tggcgtgaaa tccagcgtta ttgatatggc ccgctgggtt caggccaaca    60
tggatgccag ccacgttcag gagaaaacgc tccagcaggg cattgc                  106

<210> SEQ ID NO 280
<211> LENGTH: 84
<212> TYPE: DNA
<213> ORGANISM: Artificial Sequence
```

```
<220> FEATURE:
<223> OTHER INFORMATION: CONTROL MIX

<400> SEQUENCE: 280
gagaggatga ccagccacac tggaactgag acacggtcca gactcctacg ggaggcagca      60
gtggggaata ttgcacaatg ggcg                                            84

<210> SEQ ID NO 281
<211> LENGTH: 487
<212> TYPE: DNA
<213> ORGANISM: Artificial Sequence
<220> FEATURE:
<223> OTHER INFORMATION: CONTROL MIX

<400> SEQUENCE: 281
agcacataca gaatatgtcc ctgcatcaac atttaagatg ctaaatgcct taattggact      60
agaaaatcat aaagctacaa caactgagat tttcaaatgg gacggtaaaa agagatctta    120
tcccatgtgg gaaaagata tgactttagg tgatgccatg gcactttcag cagttcctgt    180
atatcaagaa cttgcaagac ggactggctt agacctaatg caaaagaag ttaaacgggt    240 tggttttggt aatatgaaca ttggaacaca agttgataac ttctggttgg ttggccccct    300
caagattaca ccaatacaag aggttaattt tgccgatgat tttgcaaata atcgattacc    360
ctttaaatta gagactcaag aagaagttaa aaaaatgctt ctgattaaag aattcaatgg    420
tagtaaaatt tatgcaaaaa gcggctgggg aatggatgta acccctcaag taggttggtt    480
aacaggt                                                             487

<210> SEQ ID NO 282
<211> LENGTH: 278
<212> TYPE: DNA
<213> ORGANISM: Artificial Sequence
<220> FEATURE:
<223> OTHER INFORMATION: CONTROL MIX

<400> SEQUENCE: 282
cctgatcgga ttggagaacc agaaaacgga tattaatgaa atatttaaat ggaagggcga     60
gaaaaggtca tttaccgctt gggaaaaaga catgacacta ggagaagcca tgaagctttc   120
tgcagtccca gtctatcagg aacttgcgcg acgtatcggt cttgatctca tgcaaaaaga   180
agtaaaacgt attggtttcg gtaatgctga aattggacag caggttgata atttctggtt   240
ggtaggacca ttaaaggtta cgcctattca agaggtag                           278

<210> SEQ ID NO 283
<211> LENGTH: 151
<212> TYPE: DNA
<213> ORGANISM: Artificial Sequence
<220> FEATURE:
<223> OTHER INFORMATION: CONTROL MIX

<400> SEQUENCE: 283
tagtgactgc taatccaaat cacagcgctt caaaatctga tgaaaagca gagaaaatta      60 aaaatttatt taacgaagta cactactacgg gtgttttagt tatccaacaa ggccaaactc    120
aacaaagcta tggtaatgat cttgctcgtg c                                  151

<210> SEQ ID NO 284
<211> LENGTH: 84
<212> TYPE: DNA
<213> ORGANISM: Artificial Sequence
```

<220> FEATURE:
<223> OTHER INFORMATION: CONTROL MIX

<400> SEQUENCE: 284
gagaggatga ccagccacac tggaactgag acacggtcca gactcctacg ggaggcagca    60
gtggggaata ttgcacaatg ggcg    84

<210> SEQ ID NO 285
<211> LENGTH: 553
<212> TYPE: DNA
<213> ORGANISM: Artificial Sequence
<220> FEATURE:
<223> OTHER INFORMATION: CONTROL MIX

<400> SEQUENCE: 285
aatcacaggg cgtagttgtg ctctggaatg agaataagca gcaaggattt accaataatc    60
ttaaacgggc gaaccaagca ttttacccg catctacctt aaaattccc aatagcttga    120 tcgccctcga tttgggcgtg gttaaggatg aacaccaagt ctttaagtgg atggacaga    180 cgcgcgatat cgccacttgg aatcgcgatc ataatctaat caccgcgatg aaatattcag    240
ttgtgcctgt ttatcaagaa tttgcccgcc aaattggcga ggcacgtatg agcaagatgc    300
tacatgcttt cgattatggt aatgaggaca tttcgggcaa tgtagacagt ttctggctcg    360
acggtggtat tcgaatttcg gccacggagc aaatcagctt tttaagaaag ctgtatcaca    420
ataagttaca cgtatcggag cgcagccagc gtattgtcaa acaagccatg ctgaccgaag    480
ccaatggtga ctatattatt cgggctaaaa ctggatactc gactagaatc gaacctaaga    540
ttggctggtg ggt    553

<210> SEQ ID NO 286
<211> LENGTH: 376
<212> TYPE: DNA
<213> ORGANISM: Artificial Sequence
<220> FEATURE:
<223> OTHER INFORMATION: CONTROL MIX

<400> SEQUENCE: 286
gtgggatgga aagccacgtt tttttaaagc atgggacaaa gattttactt tgggcgaagc    60
catgcaagca tctacagtgc ctgtatatca agaattggca cgtcgtattg gtccaagctt    120
aatgcaaagt gaattgcaac gtattggtta tggcaatatg caaataggca cggaagttga    180 tcaatttttgg ttgaaagggc ctttgacaat tacacctata caagaagtaa agtttgtgta    240
tgatttagcc caagggcaat tgccttttaa acctgaagtt cagcaacaag tgaaagagat    300
gttgtatgta gagcgcagag gggagaatcg tctatatgct aaaagtggct ggggaatggc    360
tgtagacccg caagtg    376

<210> SEQ ID NO 287
<211> LENGTH: 376
<212> TYPE: DNA
<213> ORGANISM: Artificial Sequence
<220> FEATURE:
<223> OTHER INFORMATION: CONTROL MIX

<400> SEQUENCE: 287
cacttgcggg tctacagcca ttccccagcc acttttagca tatagacgat tctccctct    60 gcgctctaca tacaacatct cttctcacttg ttgctgaact tcaggtttaa aaggcaattg    120
cccttgggct aaatcataca caaactttac ttcttgtata ggtgtaattg tcaaaggccc    180

```
tttcaaccaa aattgatcaa cttccgtgcc tatttgcata ttgccataac caatacgttg    240
caattcactt tgcattaagc ttggaccaat acgacgtgcc aattcttgat atacaggcac    300
tgtagatgct tgcatggctt cgcccaaagt aaaatctttg tcccatgctt taaaaaaacg    360
tggctttcca tcccac                                                   376
```

```
<210> SEQ ID NO 288
<211> LENGTH: 203
<212> TYPE: DNA
<213> ORGANISM: Artificial Sequence
<220> FEATURE:
<223> OTHER INFORMATION: CONTROL MIX

<400> SEQUENCE: 288
cacctatggt aatgctcttg cacgagcaaa taagaatat gtccctgcat caacatttaa    60
gatgctaaat gctttaatcg ggctagaaaa tcataaagca acaacaaatg agattttcaa    120
atgggatggt aaaaaaagaa cttatcctat gtgggagaaa gatatgactt taggtgaggc    180
aatggcattg tcagcagttc cag                                           203
```

```
<210> SEQ ID NO 289
<211> LENGTH: 84
<212> TYPE: DNA
<213> ORGANISM: Artificial Sequence
<220> FEATURE:
<223> OTHER INFORMATION: CONTROL MIX

<400> SEQUENCE: 289
gagaggatga ccagccacac tggaactgag acacggtcca gactcctacg ggaggcagca    60
gtggggaata ttgcacaatg ggcg                                          84
```

```
<210> SEQ ID NO 290
<211> LENGTH: 1625
<212> TYPE: DNA
<213> ORGANISM: Artificial Sequence
<220> FEATURE:
<223> OTHER INFORMATION: CONTROL MIX

<400> SEQUENCE: 290
atgatgcagc atacttctgt gtggtaccga cgctcggtca gtccgtttgt tcttgtggga    60
gtgttgccgt tttcttgacc gcgaccgcca atcttaccct ttttgataaa atcagccaaa    120
cctatcccat cgcggacaat ctcggctttg tgctgacgat cgctgtcgtg ctctttggcg    180
cgatgctact gatcaccacg ctgttatcat cgtatcgcta tgtgctaaag cctgtgttga    240
ttttgctatt aatcatgggc gcggtgacca gttatttac tgacacttat ggcacggtct    300
atgatacgac catgctccaa aatgccctac agaccgacca agccgagacc aaggatctat    360
taaacgcagc gtttatcatg cgtatcattg gtttgggtgt gctaccaagt ttgcttgtgg    420
cttttgttaa ggtggattat ccgacttggg caagggtttt gatgcgccga ttgggcttga    480
tcgtggcaag tcttgcgctg attttactgc ctgtggtggc gttcagcagt cattatgcca    540
gtttctttcg cgtgcataag ccgctgcgta gctatgtcaa tccgatcatg ccaatctact    600
cggtgggtaa gcttgccagt attgagtata aaaaagccag tgcgccaaaa gataccattt    660
atcacgccaa agacgcggta caagcaacca agcctgatat gcgtaagcca cgcctagtgg    720
tgttcgtcgt cggtgagacg gcacgcgccg atcatgtcag cttcaatggc tatgagcgcg    780
atactttccc acagcttgcc aagatcgatg gcgtgaccaa ttttagcaat gtcacatcgt    840
gcggcacatc gacggcgtat tctgtgccgt gtatgttcag ctatctgggc gcggatgagt    900
```

```
atgatgtcga taccgccaaa taccaagaaa atgtgctgga tacgctggat cgcttgggcg    960
taagtatctt gtggcgtgat aataattcgg actcaaaagg cgtgatggat aagctgccaa   1020
aagcgcaatt tgccgattat aaatccgcga ccaacaacgc catctgcaac accaatcctt   1080
ataacgaatg ccgcgatgtc ggtatgctcg ttggcttaga tgactttgtc gctgccaata   1140
acggcaaaga tatgctgatc atgctgcacc aaatgggcaa tcacgggcct gcgtatttta   1200
agcgatatga tgaaaagttt gccaaattca cgccagtgtg tgaaggtaat gagcttgcca   1260
agtgcgaaca tcagtccttg atcaatgctt atgacaatgc cttgcttgcc accgatgatt   1320
tcatcgctca agtatccag tggctgcaga cgcacagcaa tgcctatgat gtctcaatgc    1380
tgtatgtcag cgatcatggc gaaagtctgg gtgagaacgg tgtctatcta catggtatgc   1440
caaatgcctt gcaccaaaa gaacagcgca gtgtgcctgc attttctgg acggataagc     1500
aaactggcat cacgccaatg caaccgata ccgtcctgac ccatgacgcg atcacgccga    1560
cattattaaa gctgtttgat gtcaccgcgg acaaagtcaa agaccgcacc gcattcatcc   1620
gctga                                                              1625
```

<210> SEQ ID NO 291
<211> LENGTH: 1617
<212> TYPE: DNA
<213> ORGANISM: Artificial Sequence
<220> FEATURE:
<223> OTHER INFORMATION: CONTROL MIX

<400> SEQUENCE: 291

```
atgacatcac atcactcttg gtatcgctat tctatcaatc cttttgtgct gatgggtttg     60
gtggcgttat ttttggcagc gacagcgaac ctgacatttt ttgaaaaagc gatggcggtc    120
tatcctgtat cggataactt aggctttatc atctcaatgg cggtggcggt gatgggtgct    180
atgctactga ttgtcgtgct gttatcctat cgctatgtgc taaagcctgt cctgattttg    240
ctactgatta tgggtgcggt gacgagctat tttaccgata cttatggcac ggtctatgac    300
accaccatgc tccaaaatgc catgcaaacc gaccaagccg agtctaagga cttgatgaat    360
ttggcgtttt ttgtgcgaat tatcgggctt ggcgtgttgc caagtgtgtt ggtcgcagtt    420
gccaaagtca attatccaac atggggcaaa ggtctgattc agcgtgcgat gacatggggt    480
gtcagccttg tgctgttgct tgtgccgatt ggactattta gcagtcagta tgcgagtttc    540
tttcgggtgc ataagccagt gcgtttttat atcaacccga ttacgccgat ttattcggtg    600
ggtaagcttg ccagtatcga gtacaaaaaa gccactgcgc aacagacac catctatcat     660
gccaaagacg ccgtgcagac caccaagccg agcgagcgta agccacgcct agtggtgttc    720
gtcgtcggtg agacggcgcg tgctgaccat gtgcagttca atggctatgg ccgtgagact    780
ttcccgcagc ttgccaaagt tgatggcttg gcgaatttta gccaagtgac atcgtgtggc    840
acatcgacgg cgtattctgt gccgtgtatg ttcagctatt tgggtcaaga tgactatgat    900
gtcgataccg ccaaatacca agaaaatgtg ctagatacgc ttgaccgctt gggtgtgggt    960
atcttgtggc gtgataataa ttcagactca aaaggcgtga tggataagct acctgccacg   1020
cagtattttg attataaatc agcaaccaac aataccatct gtaacaccaa tccctataac   1080
gaatgccgtg atgtcggtat gcttgtcggg ctagatgact atgtcagcgc caataatggc   1140
aaagatatgc tcatcatgct acaccaaatg ggcaatcatg ggccggcgta ctttaagcgt   1200
tatgatgagc aatttgccaa attcacccc gtgtgcgaag caacgagct tgccaaatgc     1260
gaacaccaat cactcatcaa tgcctatgac aatgcgctac ttgcgactga tgattttatc   1320
```

| | |
|---|---|
| gccaaaagca tcgattggct aaaaacgcat gaagcgaact acgatgtcgc catgctctat | 1380 |
| gtcagtgacc acggcgagag cttgggcgaa aatggtgtct atctgcatgg tatgccaaat | 1440 |
| gcctttgcac caaaagaaca gcgagctgtg cctgcgtttt tttggtcaaa taatacgaca | 1500 |
| ttcaagccaa ctgccagcga tactgtgctg acgcatgatg cgattacgcc aacactgctt | 1560 |
| aagctgtttg atgtcacagc gggcaaggtc aaagaccgcg cggcatttat ccagtaa | 1617 |

<210> SEQ ID NO 292
<211> LENGTH: 84
<212> TYPE: DNA
<213> ORGANISM: Artificial Sequence
<220> FEATURE:
<223> OTHER INFORMATION: CONTROL MIX

<400> SEQUENCE: 292

| | |
|---|---|
| gagaggatga ccagccacac tggaactgag acacggtcca gactcctacg ggaggcagca | 60 |
| gtggggaata ttgcacaatg ggcg | 84 |

<210> SEQ ID NO 293
<211> LENGTH: 750
<212> TYPE: DNA
<213> ORGANISM: Artificial Sequence
<220> FEATURE:
<223> OTHER INFORMATION: CONTROL MIX

<400> SEQUENCE: 293

| | |
|---|---|
| agatcagttg ggtgcacgag tgggttacat cgaactggat ctcaacagcg gtaagatcct | 60 |
| tgagagtttt cgccccgaag aacgttttcc aatgatgagc acttttaaag ttctgctatg | 120 |
| tggtgcggta ttatcccgtg ttgacgccgg gcaagagcaa ctcggtcgcc gcatacacta | 180 |
| ttctcagaat gacttggttg agtactcacc agtcacagaa aagcatctta cggatggcat | 240 |
| gacagtaaga gaattatgca gtgctgccat aaccatgagt gataacactg cggccaactt | 300 |
| acttctgaca acgatcggag gaccgaagga gctaaccgct tttttgcaca acatggggga | 360 |
| tcatgtaact cgccttgatc gttgggaacc ggagctgaat gaagccatac caaacgacga | 420 |
| gcgtgacacc acgacgcctg cagcaatggc aacaacgttg cgcaaactat taactggcga | 480 |
| actacttact ctagcttccc ggcaacaatt aatagactgg atggaggcgg ataaagttgc | 540 |
| aggaccactt ctgcgctcgg cccttccggc tggctggttt attgctgata atctggagc | 600 |
| cagtgagcgt gggtctcgcg gtatcattgc agcactgggg ccagatggta agccctcccg | 660 |
| tatcgtagtt atctacacga cggggagtca ggcaactatg gatgaacgaa atagacagat | 720 |
| cgctgagata ggtgcctcac tgattaagca | 750 |

<210> SEQ ID NO 294
<211> LENGTH: 372
<212> TYPE: DNA
<213> ORGANISM: Artificial Sequence
<220> FEATURE:
<223> OTHER INFORMATION: CONTROL MIX

<400> SEQUENCE: 294

| | |
|---|---|
| ctggagcgaa agatccacta tcgccagcag gatctggtgg actactcgcc ggtcagcgaa | 60 |
| aaacaccttg ccgacggcat gacggtcggc gaactctgcg ccgccgccat taccatgagc | 120 |
| gataacagcg ccgccaatct gctgctggcc accgtcggcg gccccgcagg attgactgcc | 180 |
| tttttgcgcc agatcggcga caacgtcacc cgccttgacc gctgggaaac ggaactgaat | 240 |
| gaggcgcttc ccgcgacgc ccgcgacacc actaccccgg ccagcatggc cgcgaccctg | 300 |

```
cgcaagctgc tgaccagcca gcgtctgagc gcccgttcgc aacggcagct gctgcagtgg    360
atggtggacg at                                                        372

<210> SEQ ID NO 295
<211> LENGTH: 84
<212> TYPE: DNA
<213> ORGANISM: Artificial Sequence
<220> FEATURE:
<223> OTHER INFORMATION: CONTROL MIX

<400> SEQUENCE: 295
gagaggatga ccagccacac tggaactgag acacggtcca gactcctacg ggaggcagca    60
gtggggaata ttgcacaatg ggcg                                           84

<210> SEQ ID NO 296
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 6-FAM
<220> FEATURE:
<221> NAME/KEY: misc_feature
<222> LOCATION: (9)..(9)
<223> OTHER INFORMATION: ZEN
<220> FEATURE:
<221> NAME/KEY: misc_feature
<222> LOCATION: (27)..(27)
<223> OTHER INFORMATION: IABkFQ

<400> SEQUENCE: 296
aggatggcaa ggcccactat ttca                                           24

<210> SEQ ID NO 297
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: HEX
<220> FEATURE:
<221> NAME/KEY: misc_feature
<222> LOCATION: (9)..(9)
<223> OTHER INFORMATION: ZEN
<220> FEATURE:
<221> NAME/KEY: misc_feature
<222> LOCATION: (27)..(27)
<223> OTHER INFORMATION: IABkFQ

<400> SEQUENCE: 297
agccattacg ttccagagtt gcgt                                           24

<210> SEQ ID NO 298
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: TEX615
```

```
<220> FEATURE:
<221> NAME/KEY: misc_feature
<222> LOCATION: (24)..(24)
<223> OTHER INFORMATION: 3IAbRQSp

<400> SEQUENCE: 298
tctgctgaag tttrycgagg cmaa                                              24

<210> SEQ ID NO 299
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: TYE665
<220> FEATURE:
<221> NAME/KEY: misc_feature
<222> LOCATION: (24)..(24)
<223> OTHER INFORMATION: IAbRQSp

<400> SEQUENCE: 299
tgagacacgg tccagactcc tacg                                              24

<210> SEQ ID NO 300
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 6-FAM
<220> FEATURE:
<221> NAME/KEY: misc_feature
<222> LOCATION: (9)..(9)
<223> OTHER INFORMATION: ZEN
<220> FEATURE:
<221> NAME/KEY: misc_feature
<222> LOCATION: (24)..(24)
<223> OTHER INFORMATION: IABkFQ

<400> SEQUENCE: 300
aaaccgggcg atatgcgtct gtat                                              24

<210> SEQ ID NO 301
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: HEX
<220> FEATURE:
<221> NAME/KEY: misc_feature
<222> LOCATION: (9)..(9)
<223> OTHER INFORMATION: ZEN
<220> FEATURE:
<221> NAME/KEY: misc_feature
<222> LOCATION: (23)..(23)
<223> OTHER INFORMATION: IABkFQ

<400> SEQUENCE: 301
gatgccattg cycgsggtga aat                                               23
```

```
<210> SEQ ID NO 302
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: TEX615
<220> FEATURE:
<221> NAME/KEY: misc_feature
<222> LOCATION: (20)..(20)
<223> OTHER INFORMATION: IAbRQSp

<400> SEQUENCE: 302
atgttggcct gaacccagcg                                              20
```

ASSAYS AND METHODS FOR DETERMINING MICROBIAL RESISTANCE

CROSS-REFERENCE TO RELATED APPLICATIONS

This application is a U.S. National Phase of PCT/US17/37700, filed Jun. 15, 2017, which claims the priority benefit under 35 U.S.C. § 119(e) of U.S. Provisional Patent Application No. 62/350,457, filed Jun. 15, 2016, which are incorporated herein by reference in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "50035_SubSeqListing.txt", which was created on Mar. 14, 2022 and is 77,233 bytes in size. The subject matter of the Sequence Listing is incorporated herein in its entirety by reference.

FIELD

The present teachings relate to assays and methods for detecting resistance to antibiotics. The present teachings provide for the detection of family specific gene targets including AmpC β-lactamases, metallo-β-lactamases, carbapenemases, and extended-spectrum β-Lactamases by multiplex real-time polymerase chain reaction.

BACKGROUND

Bacterial resistance to antibiotics is a major public health issue. This resistance not only presents severe limitations to the ability to control and treat infection, but it also is difficult to identify and characterize in the laboratory. The significant increase in the resistance of pathogenic bacteria over the last 20 years, leads to extended periods of hospitalization, high morbidity and high mortality rates.

Enzymatic inactivation is the most common cause of resistance in terms of number of species and of antibiotics involved. As an example, β-lactamases are enzymes expressed by some bacteria. Such enzymes are capable of hydrolyzing the C—N bond of the β-lactam ring structure of a β-lactam antibiotic, effectively inactivating the antibiotic. Despite the existence of several β-lactamase inhibitors, the constant exposure of strains to antibiotics results in constant evolution of β-lactamases.

As a result, it becomes essential to be able to identify such resistant microorganisms and their resistance mechanisms as quickly as possible. Typically, biological samples can be tested for antibiotic resistance, but many test protocols are time consuming and/or limited in the types of resistance they are able to identify. It would therefore be beneficial to provide a test protocol for the simplified identification of resistance for all major β-lactamases.

One approach to the identification of β-lactamases has been to employ oligonucleotide primers specific for nucleic acid characteristic of certain β-lactamases with polymerase chain reaction to identify nucleic acid characteristics of family specific β-lactamase enzymes in samples. See for example, U.S. Pat. Nos. 6,893,846 and 7,476,520, incorporated by reference herein. Another approach has been to employ oligonucleotide primers specific for nucleic acid characteristic of certain AmpC β-lactamases with multiplex polymerase chain reaction to detect the presence or absence of an AmpC β-lactamase gene and to identify nucleic acid characteristic of AmpC β-lactamase genes in samples. Multiplex polymerase chain reaction refers to the use of polymerase chain reaction to amplify several different DNA sequences simultaneously in single or multiple reactions. See for example, U.S. Pat. Nos. 7,045,291 and 7,521,547 incorporated by reference herein.

However, such primers have been limited with regards to the number of β-lactamase gene families or the number of gene targets that may be identified. Furthermore, such primers have been employed mainly with conventional polymerase chain reaction, which typically requires agarose gels to detect and analyze the PCR product(s). The use of agarose gel detection methods based on size discrimination may lead to poor resolution and difficulty in interpreting the data. Conventional polymerase chain reaction also lacks the sensitivity to detect endpoint variability from sample to sample and may not be automated. Real-time polymerase chain reaction allows for monitoring of reaction products as they are formed.

Detection of β-lactamases using real-time polymerase chain reaction and a single primer set may be limited to detection of a single β-lactamase gene family. See for example, United States Patent Application 2007/0248954 incorporated by reference herein. Multiplex real-time polymerase chain reaction has been designed for the identification of many AmpC β-lactamases simultaneously. See Geyer C N, Reisbig M D, Hanson N D. Development of a TaqMan® Multiplex PCR Assay for Detection of Plasmid-Mediated AmpC β-lactamase Genes. *Journal of clinical microbiology*. 2012 Aug. 15:JCM-02038. The primer/probe combinations in this study, however, have been directed only to AmpC β-lactamases and are limited in the number of gene targets that may be identified.

Multiple factors such as primer and probe design, reaction conditions, and enzyme selection must all be considered when designing a working polymerase chain reaction. This complexity is compounded in multiplex PCR, in which multiple targets are detected simultaneously in the same tube. Balancing the concentrations of primers, probes, and control vectors provided as composite "multiplex PCR" mixes for an assay is a challenging aspect. It is extremely difficult to balance these ratios, as a change of concentration for any of these reagents, corresponding to just one of the genetic targets, may adversely affect detection of any other multiplex target in the reaction mix. If these concentrations are not balanced, one could expect a reduction in efficiency, sensitivity, and specificity. This would reduce confidence in the effectiveness of the assay to correctly identify the gene families identified with the described kits.

Therefore, there is a significant amount of time and technical know-how required to develop these assays into a reliable method. For example, the PCR master mixture, with DNA polymerase, is a customized formulation that permits the final assay to work. Concentrations of DNA polymerase and magnesium may have to be adjusted. The specific concentrations and ranges surrounding DNA polymerase and magnesium are required for the assay to work successfully. In addition to determining concentrations for all reagents, a PCR cycling protocol must be identified that is compatible with all reaction conditions and facilitates real-time multiplex polymerase chain reaction.

Accurate and rapid detection of antibiotic resistance is essential for surveillance, epidemiologic tracking, patient therapy, and infection control. Thus, a multiplex PCR based diagnostic assay should provide comprehensive genotypic characterization of β-lactamases and be versatile as well as providing rapid results. The present teachings make it possible to test a sample for the presence of antibiotic resistant microorganisms by identifying any of the major β-lactamases in one test. The present teachings provide for the detection of multiple family-specific β-lactamase gene targets, including but not limited to metallo-β-lactamases, carbapenemases, extended-spectrum β-Lactamases, ampC chromosomal and/or plasmid-mediated AmpC β-lactamases, by multiplex real-time polymerase chain reaction.

The present teachings provide for a kit or kits including one or more primers and/or probes for identification of β-lactamase genes selected from the group consisting of one or more of the following: MOX-like, FOX-like, ACC-like, ACT/MIR-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. The kits or kits of the present teachings may provide control material for the aforementioned β-lactamase genes. The present teachings provide one or more of the following: primers, probes, controls, assay process and detection strategy for one or more of the following β-lactamases: extended-spectrum β-lactamases (ESBLs), metallo-β-lactamases (MBLs), carbapenem-resistant enterobacteriaceaes (CREs), and serine-dependent carbapenemases and plasmid-mediated ampC β-lactamases. A kit may also include one or more primers and/or probes for the identification of mobilized colistin-resistant (MCR) genes, a non-beta lactamase gene family that confers antibiotic resistance. The present teachings provide multiplex PCR assays which may test for any combination of these or are directed towards identification of a specific group. The present teachings provide assays with improved clinical sensitivity and analytical specificity of detection. The primer, probes, and control DNA sequences of the present teachings provide both an analytical and commercial advantage as they permit enhanced screening capabilities for detection of a larger number of genetic variants associated with genes conferring resistance to antibiotics in Gram-negative bacteria.

SUMMARY

The present teachings provide a kit including one or more primers and/or probes for the identification by polymerase chain reaction, microarray, NGS-based target enrichment, and/or mass spectrometric characterization of one or more β-lactamase genes selected from the group consisting of: CMY, CTX-M, OXA, IMP, VIM, DHA, KPC, MOX, ACC, FOX, EBC, NDM, TEM, and SHV. The present teachings provide for one or more kits including primers and/or probes for identification of β-lactamase genes selected from the group consisting of one or more of the following: MOX-like, FOX-like, ACC-like, EBC-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. A kit may also include one or more primers and/or probes for the identification of a non-beta lactamase gene family which confers antibiotic resistance. A kit may include one or more primers and/or probes for the identification by polymerase chain reaction or microarray of MCR gene variants. Primers and probes may also be made compatible with next-generation sequencing and mass spectrometry.

DETAILED DESCRIPTION

Figure 1:
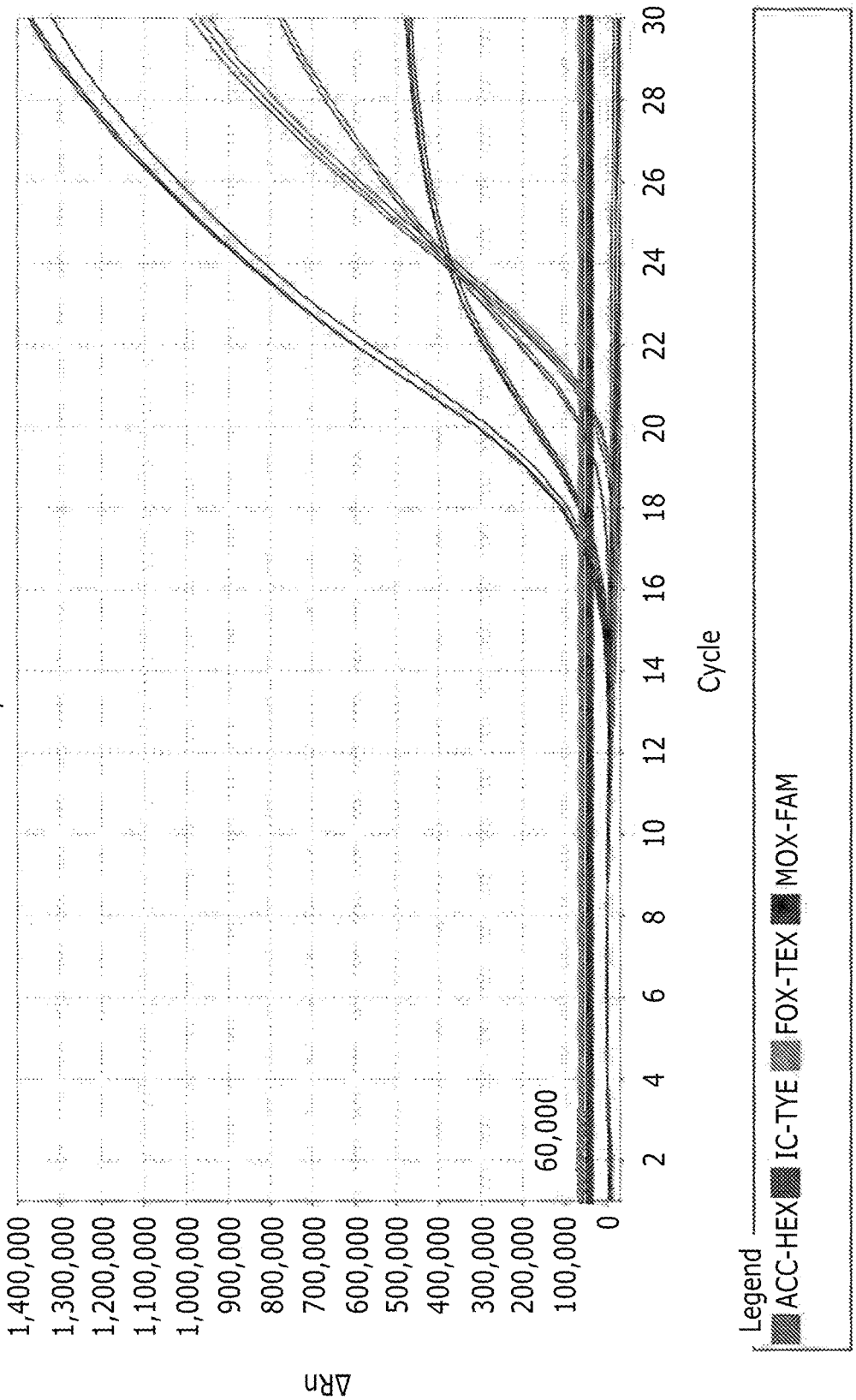
FIG. 1 depicts an amplification plot of an exemplary mix 1 of a kit including ampC gene targets.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Bacterial resistance to antibiotics poses a global threat to public health and in recent years has shown an increase in mortality rates and the potential to spread through the population. Of these resistance mechanisms, β-Lactamases are enzymes that cleave β-Lactam rings rendering the β-Lactam family of antibiotics ineffective for treatment of clinically-important Gram-negative bacterial infections. Specifically, β-Lactamases confer resistance to penicillins, cephamycins, and, in some cases, carbapenems. β-Lactam-resistant Gram-negative organisms, producing multiple or plasmid-mediated β-lactamases, are difficult to identify phenotypically and necessitate more specific detection methods to identify clinically important β-lactamases. Genetic identification of these resistance mechanisms is critical for active surveillance and infection control. Because these antibiotics are often selected for the management and prevention of infectious disease, the presence and characteristics of specific β-Lactamases play a critical role in selecting the appropriate antibiotic therapy.

AmpC β-lactamases are clinically important cephalosporinases that are resistant to most β-lactam antibiotics. AmpC enzymes are chromosomally encoded in many bacterial species and can be inducible and overexpressed as a consequence of mutation. Overexpression can lead to resistance to most β-lactam antibiotics. The occurrence of transmissible plasmids with acquired genes for AmpC β-lactamases often result in increased β-lactamase production, compared to chromosomally-expressed ampC genes. Additionally, plasmid-mediated AmpC β-lactamases can appear in organisms lacking or having low-level expression of a chromosomal ampC gene. Resistance due to plasmid-mediated AmpC enzymes can be broad in spectrum and often hard to detect. As such, it is clinically useful to detect and discriminate between plasmid-mediated and chromosomally expressed AmpC β-lactamases.

The present teachings relate to assays and methods for detecting Gram-negative bacteria resistant to beta-lactam antibiotics from a biological sample. β-lactam antiobiotics are all antiobiotic agents that contain a β-lactam ring in their molecular structures. β-lactam antiobiotics include penicillins, cephalsoprins, carbapenems and monobactams. Antibiotic resistant organisms may produce one or more enzymes known as β-lactamases that provide resistance to β-lactam antibiotics. β-lactamases may confer resistance by the bacteria to antibiotics, which is plasmid-mediated and/or chromosomally expressed making detection difficult.

β-lactamases may be classified based on molecular structure. The four major classes include A to D. Class A, C and D β-lactamases are serine based. Class B β-lactamases, also known as metallo-beta-lactamases, are zinc based.

Extended spectrum β-lactamases (ESBLs) are enzymes that confer bacterial resistance to certain categories of antibiotics, such as third-generation cephalsoprins and monobactams. The presence of an ESBL-producing organism in a clinical infection can cause treatment failure if one of the above classes of drugs is used. Detection of ESBLs can be difficult because they have different levels of activity against various cephalosporins. Thus genetic identification of the exact enzyme can facilitate selection of the optimal antimicrobial agent, which is critical to determine the most effective treatment response.

First-generation cephalosporins include cefalexin, cefaloridine, cefalotin, cefazolin, cefadroxil, cefazedone, cefatrizine, cefapirin, cefradine, cefacetrile, cefrodaxine, ceftezole. Second-generation cephalosporins include cefoxitin, cefuroxime, cefamandole, cefaclor, cefotetan, cefonicide, cefotiam, loracarbef, cefmetazole, cefprozil, ceforanide. Third-generation cephalosporins include cefotaxime, ceftazidime, cefsulodine, ceftriaxone, cefmenoxime, latamoxef, ceftizoxime, cefixime, cefodizime, cefetamet, cefpiramide, cefoperazone, cefpodoxime, ceftibuten, cefdinir, cefditoren, ceftriaxone, cefoperazone, cefbuperazone. Fourth-generation cephalosporins include cefepime and cefpirome.

β-lactamase producing bacteria may include Gram-negative bacteria such as those found in the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia* and *Legionella*.

Antibiotic resistance is intended to mean any type of mechanism which allows a microorganism to render a treatment partially or completely ineffective on the microorganism, guaranteeing its survival. β-lactam antibiotic resistance is intended to mean any type of β-lactamase-based mechanism which allows a microorganism to render a treatment partially or completely ineffective on the microorganism, guaranteeing its survival. For example, wherein the mechanism is related to the expression of an enzyme belonging to the β-lactamase group including extended-spectrum β-lactamase or of an enzyme belonging to the group of class C cephalosporinases.

Biological sample is intended to mean a clinical sample, derived from a specimen of biological fluid, or a food sample, derived from any type of food or drink, or from an agricultural source, such as animals, soil, water, or air, or from a surface such as with a biofilm. This sample may thus be liquid or solid. For example the biological sample may be a clinical sample of blood, plasma, urine or feces, or of rectal, nose, throat, skin, wound or cerebrospinal fluid specimens.

The present teachings relate to assays and methods for detecting resistance to beta-lactam antibiotics. The present teachings may detect β-lactamase gene targets which are chromosomally encoded and/or plasmid mediated. The present teachings provide for the detection of family specific gene targets relating to β-lactamase genes including AmpC β-lactamases. The β-lactamase genes detected with the present teachings may include those classified into molecular groups A through D. The β-lactamase genes detected with the present teachings may include those classified into functional groups 1 through 3.

The present teachings relate to assays and methods for detecting resistance of one or more gene beta lactamase gene families including like genes. A like gene may be a beta-lactamase that has one or more of the following: similar amino acid sequence, similar function and similar antibiotic susceptibility profiles. A like gene may be considered as like the target gene detected with the present teachings. For example, OXA-48-like enzymes may include: OXA-48, OXA-48b, OXA-162, OXA-163, OXA-181, OXA-199, OXA-204, OXA-232, OXA-244, OXA-245 and OXA-24.

The present teachings provide one or more primers and/or probes for the identification of one or more β-lactamase genes selected from the group consisting of: CMY, CTX-M, OXA, IMP, VIM, DHA, KPC, MOX, ACC, FOX, EBC, NDM, TEM, and SHV. The present teachings provide one or more primers and/or probes for the identification of β-lactamase genes selected from the group consisting of one or more of the following: MOX-like, FOX-like, ACC-like, EBC-like, CMY-2-like, DHA-like, CTX-M-14-like, CTX-M-15-like, VIM-like, NDM-like, IMP-like, KPC-like, and OXA-48-like, OXA-51-like, OXA-143-like, OXA-58-like, OXA-23-like, OXA-24/40-like, TEM-like, and SHV-like. The present teachings provide one or more primers and/or probes for the identification of a non-beta lactamase gene family which confers antibiotic resistance. For example, one or more primers and/or probes for the identification of MCR gene variants. The primers and/or probes of the present teachings may be included in one or more kits. The one or more kits may be used for identification with any of the following: polymerase chain reaction, microarray, NGS-based target enrichment, and/or mass spectrometric characterization.

Exemplary sequences for primers and probes for of the present teachings are depicted in Table 1. [SEQ. ID NOS 67-260] Primers and/or probes may be degenerate at any nucleotide position. Primers and/or probes may not be degenerate at any nucleotide position. Any suitable fluorophore and/or quencher and nucleic acid sequence combination may be used. For example, a probe may be labeled with a fluorescent tag at one end and a fluorescent quencher at the other end. For example, a probe may be labeled with a fluorescent tag at one end and a fluorescent quencher at the other end. For example, two fluorescent quenchers may be included at one end or within the probe sequence. It is contemplated that the probe sequences of the present teachings may be labeled with any suitable fluorophore and quencher combinations. For example, any fluorophore of the present teachings may be attached to any probe DNA sequence of the present teachings.

TABLE 1

| | Primer/Probe Sequence |
|---|---|
| SEQ ID NO. 67 | TGGCCAGAACTGACAGGCAAA |
| SEQ ID NO. 68 | TTTCTCCTGAACGTGGCTGGC |
| SEQ ID NO. 69 | 56-FAM/ACGCTAACT/ZEN/CCAGCATTGGTCTGT/3IABkFQ/ |
| SEQ ID NO. 70 | CCGTCACGCTGTTGTTAGG |
| SEQ ID NO. 71 | GCTGTGTTAATCAATGCCACAC |
| SEQ ID NO. 72 | 5HEX/AACTTGCCG/ZEN/AATTAGAGCRGCAGT/3IABkFQ |
| SEQ ID NO. 73 | CGTTTCGTCTGGATCGCAC |
| SEQ ID NO. 74 | GCTGGGTAAAATAGGTCACC |
| SEQ ID NO. 75 | 5TEX615/TATCATTGGTGGTGCCGTAGTCGC/3IAbRQSp |
| SEQ ID NO. 76 | GAGAGGATGAYCAGCCACAC |
| SEQ ID NO. 77 | CGCCCATTGTSCAATATTCC |
| SEQ ID NO. 78 | 5TYE665/TGAGACACGGTCCAGACTCCTACG/3IAbRQSp |
| SEQ ID NO. 79 | AATCACAGGGCGTAGTTGTG |
| SEQ ID NO. 80 | ACCCACCAGCCAATCTTAGG |
| SEQ ID NO. 81 | 56-FAM/TAGCTTGAT/ZEN/CGCCCTCGATTTGGG/3IABkFQ/ |
| SEQ ID NO. 82 | GCGGAGTTAACTATTGGCTAG |
| SEQ ID NO. 83 | GGCCAAGCTTCTATATTTGCG |
| SEQ ID NO. 84 | 5HEX/TTRTTYGGT/ZEN/GGTTGYTTTRTTAA/3IABkFQ |
| SEQ ID NO. 85 | GCGGAGTTARYTATTGGCTAG |
| SEQ ID NO. 86 | GGCCAAGCYTCTAWATTTGCG |
| SEQ ID NO. 87 | /5HEX/CCGGACGGT/ZEN/CTTGGTAATTTGGGT/3IABkFQ/ |
| SEQ ID NO. 88 | /5HEX/CCGTACGGT/ZEN/TTAGGCAATTTGGGT/3IABkFQ/ |
| SEQ ID NO. 89 | GGCGGCGTTGATGTCCTTCG |
| SEQ ID NO. 90 | CCATTCAGCCAGATCGGCATC |
| SEQ ID NO. 91 | 5TEX615/AGCTCTTCTATCCTGGTGCTGCG/3IAbRQSp |
| SEQ ID NO. 92 | AACTTTCACAGGTGTGCTGGGT |
| SEQ ID NO. 93 | CCGTACGCATACTGGCTTTGC |
| SEQ ID NO. 94 | 56-FAM/AAACCGGGC/ZEN/GATATGCGTCTGTAT/3IABkFQ/ |
| SEQ ID NO. 95 | GTATCGCCGTCTAGTTCTGC |
| SEQ ID NO. 96 | CCTTGAATGAGCTGCACAGTGG |
| SEQ ID NO. 97 | 5HEX/TCGTCGCGG/ZEN/AACCATTCGCTAAA/3IABkFQ/ |
| SEQ ID NO. 98 | GTTTGATCGTCAGGGATGGC |
| SEQ ID NO. 99 | GGCGAAAGTCAGGCTGTG |
| SEQ ID NO. 100 | 5TEX615/CATCAGGACAAGATGGGCGGTATG/3IAbRQSp |
| SEQ ID NO. 101 | GCTGCTCAAGGAGCACAGGAT |
| SEQ ID NO. 102 | CACATTGACATAGGTGTGGTGC |
| SEQ ID NO. 103 | 56-FAM/AGGATGGCA/ZEN/AGGCCCACTATTTCA/3IABkFQ/ |
| SEQ ID NO. 104 | AACAGCCTCAGCAGCCGGTTA |
| SEQ ID NO. 105 | TTCGCCGCAATCATCCCTAGC |

TABLE 1-continued

| | Primer/Probe Sequence |
|---|---|
| SEQ ID NO. 106 | 5HEX/AGCCATTAC/ZEN/GTTCCAGAGTTGCGT/3IABkFQ |
| SEQ ID NO. 107 | GCCGAGGCTTACGGGATCAAG |
| SEQ ID NO. 108 | CAAAGCGCGTAACCGGATTGG |
| SEQ ID NO. 109 | 5TEX615/TCTGCTGAAGTTTRYCGAGGCMAA/3IAbRQSp |
| SEQ ID NO. 110 | AACTTTCACAGGTGTGCTGGGT |
| SEQ ID NO. 111 | CCGTACGCATACTGGCTTTGC |
| SEQ ID NO. 112 | 56-FAM/AAACCGGGC/ZEN/GATATGCGTCTGTAT/3IABkFQ/ |
| SEQ ID NO. 113 | CTGGGTTCTATAAGTAAAACCTTCACCGG |
| SEQ ID NO. 114 | CTTCCACTGCGGCTGCCAGTT |
| SEQ ID NO. 115 | 5HEX/GATGCCATT/ZEN/GCYCGSGGTGAAAT/3IABkFQ |
| SEQ ID NO. 116 | CCGAAGCCTATGGCGTGAAATCC |
| SEQ ID NO. 117 | GCAATGCCCTGCTGGAGCG |
| SEQ ID NO. 118 | 5TEX615/ATGTTGGCCTGAACCCAGCG/3IAbRQSp |
| SEQ ID NO. 119 | AGCACATACAGAATATGTCCCTGC |
| SEQ ID NO. 120 | ACCTGTTAACCAACCTACTTGAGGG |
| SEQ ID NO. 121 | /56-FAM/TTGCAAGACGGACTGGCTTAGACC/3BHQ_1/ |
| SEQ ID NO. 122 | CCTGATCGGATTGGAGAACC |
| SEQ ID NO. 123 | CTACCTCTTGAATAGGCGTAACC |
| SEQ ID NO. 124 | /5TEX615/ACGTCGCGCAAGTTCCTGATAGAC/3IAbRQSp/ |
| SEQ ID NO. 125 | TAGTGACTGCTAATCCAAATCACAG |
| SEQ ID NO. 126 | GCACGAGCAAGATCATTACCATAGC |
| SEQ ID NO. 127 | /5HEX/AGTTATCCAACAAGGCCAAACTCAACA/3BHQ_1/ |
| SEQ ID NO. 128 | AATCACAGGGCGTAGTTGTG |
| SEQ ID NO. 129 | ACCCACCAGCCAATCTTAGG |
| SEQ ID NO. 130 | /5HEX/TAGCTTGATCGCCCTCGATTTGGG/3BHQ_1/ |
| SEQ ID NO. 131 | GTGGGATGGAAAGCCACG |
| SEQ ID NO. 132 | CACTTGCGGGTCTACAGC |
| SEQ ID NO. 133 | /56-FAM/TTACTTTGGGCGAAGCCATGCAAG/3BHQ_1/ |
| SEQ ID NO. 134 | CACCTATGGTAATGCTCTTGC |
| SEQ ID NO. 135 | CTGGAACTGCTGACAATGCC |
| SEQ ID NO. 136 | /5TEX615/TGGGAGAAAGATATGACTTTAGGTGAGGCA/3IAbRQSp/ |
| SEQ ID NO. 137 | CCGTGTATGTTCAGCTAT |
| SEQ ID NO. 138 | CTTATCCATCACGCCTTT |
| SEQ ID NO. 139 | /5TEX615/TATGATGTCGATACCGCCAAATACCA/3IAbRQSp/ |
| SEQ ID NO. 140 | CTGTATGTCAGCGATCAT |
| SEQ ID NO. 141 | GATGCCAGTTTGCTTATCC |
| SEQ ID NO. 142 | /56FAM/AAGTCTGGG/ZEN/TGAGAACGGTGTCTAT/3IABkFQ |
| SEQ ID NO. 143 | CAGTCAGTATGCGAGTTTC |
| SEQ ID NO. 144 | AAAATTCGCCAAGCCATC, |

TABLE 1-continued

| | Primer/Probe Sequence |
|---|---|
| SEQ ID NO. 145 | /5HEX/TGCATAAGC/ZEN/CAGTGCGTTTTTATAT/3IABkFQ |
| SEQ ID NO. 146 | AGATCAGTTGGGTGCACG |
| SEQ ID NO. 147 | TGCTTAATCAGTGAGGCACC |
| SEQ ID NO. 148 | /56-FAM/ATGAAGCCA/ZEN/TACCAAACGACGAGC/3IABkFQ/ |
| SEQ ID NO. 149 | CTGGAGCGAAAGATCCACTA |
| SEQ ID NO. 150 | ATCGTCCACCATCCACTG |
| SEQ ID NO. 151 | /5HEX/CCAGATCGG/ZEN/CGACAACGTCACC/3IABkFQ/ |
| SEQ ID NO. 152 | TGGCCAGAACTGACAGGCAAA |
| SEQ ID NO. 153 | TTTCTCCTGAACGTGGCTGGC |
| SEQ ID NO. 154 | 56-FAM/ACGCTAACT/ZEN/CCAGCATTGGTCTGT/3IABkFQ/ |
| SEQ ID NO. 155 | CCGTCACGCTGTTGTTAGG |
| SEQ ID NO. 156 | GCTGTGTTAATCAATGCCACAC |
| SEQ ID NO. 157 | 5HEX/AACTTGCCG/ZEN/AATTAGAGCRGCAGT/3IABkFQ |
| SEQ ID NO. 158 | CGTTTCGTCTGGATCGCAC |
| SEQ ID NO. 159 | GCTGGGTAAAATAGGTCACC |
| SEQ ID NO. 160 | 5TEX615/TATCATTGGTGGTGCCGTAGTCGC/3IAbRQSp |
| SEQ ID NO. 161 | GAGAGGATGAYCAGCCACAC |
| SEQ ID NO. 162 | CGCCCATTGTSCAATATTCC |
| SEQ ID NO. 163 | 5TYE665/TGAGACACGGTCCAGACTCCTACG/3IAbRQSp |
| SEQ ID NO. 164 | AATCACAGGGCGTAGTTGTG |
| SEQ ID NO. 165 | ACCCACCAGCCAATCTTAGG |
| SEQ ID NO. 166 | 56-FAM/TAGCTTGAT/ZEN/CGCCCTCGATTTGGG/13IABkFQ/ |
| SEQ ID NO. 167 | GCGGAGTTAACTATTGGCTAG |
| SEQ ID NO. 168 | GGCCAAGCTTCTATATTTGCG |
| SEQ ID NO. 169 | 5HEX/TTRTTYGGT/ZEN/GGTTGYTTTRTTAA/3IABkFQ |
| SEQ ID NO. 170 | GCGGAGTTARYTATTGGCTAG |
| SEQ ID NO. 171 | GGCCAAGCYTCTAWATTTGCG |
| SEQ ID NO. 172 | /5HEX/CCGGACGGT/ZEN/CTTGGTAATTTGGGT/3IABkFQ/ |
| SEQ ID NO. 173 | /5HEX/CCGTACGGT/ZEN/TTAGGCAATTTGGGT/3IABkFQ |
| SEQ ID NO. 174 | GGCGGCGTTGATGTCCTTCG |
| SEQ ID NO. 175 | CCATTCAGCCAGATCGGCATC |
| SEQ ID NO. 176 | 5TEX615/AGCTCTTCTATCCTGGTGCTGCG/3IAbRQSp |
| SEQ ID NO. 177 | GAGAGGATGAYCAGCCACAC |
| SEQ ID NO. 178 | CGCCCATTGTSCAATATTCC |
| SEQ ID NO. 179 | 5TYE665/TGAGACACGGTCCAGACTCCTACG/3IAbRQSp |
| SEQ ID NO. 180 | AACTTTCACAGGTGTGCTGGGT |
| SEQ ID NO. 181 | CCGTACGCATACTGGCTTTGC |
| SEQ ID NO. 182 | 56-FAM/AAACCGGGC/ZEN/GATATGCGTCTGTAT/3IABkFQ/ |
| SEQ ID NO. 183 | GTATCGCCGTCTAGTTCTGC |

TABLE 1-continued

| | Primer/Probe Sequence |
|---|---|
| SEQ ID NO. 184 | CCTTGAATGAGCTGCACAGTGG |
| SEQ ID NO. 185 | 5HEX/TCGTCGCGG/ZEN/AACCATTCGCTAAA/3IABkFQ/ |
| SEQ ID NO. 186 | GTTTGATCGTCAGGGATGGC |
| SEQ ID NO. 187 | GGCGAAAGTCAGGCTGTG |
| SEQ ID NO. 188 | 5TEX615/CATCAGGACAAGATGGGCGGTATG/3IAbRQSp |
| SEQ ID NO. 189 | GAGAGGATGAYCAGCCACAC |
| SEQ ID NO. 190 | CGCCCATTGTSCAATATTCC |
| SEQ ID NO. 191 | 5TYE665/TGAGACACGGTCCAGACTCCTACG/3IAbRQSp |
| SEQ ID NO. 192 | GCTGCTCAAGGAGCACAGGAT |
| SEQ ID NO. 193 | CACATTGACATAGGTGTGGTGC |
| SEQ ID NO. 194 | 56-FAM/AGGATGGCA/ZEN/AGGCCCACTATTTCA/3IABkFQ |
| SEQ ID NO. 195 | AACAGCCTCAGCAGCCGGTTA |
| SEQ ID NO. 196 | TTCGCCGCAATCATCCCTAGC |
| SEQ ID NO. 197 | 5H EX/AGCCATTAC/ZEN/GTTCCAGAGTTGCGT/3IABkFQ |
| SEQ ID NO. 198 | GCCGAGGCTTACGGGATCAAG |
| SEQ ID NO. 199 | CAAAGCGCGTAACCGGATTGG |
| SEQ ID NO. 200 | 5TEX615/TCTGCTGAAGTTTRYCGAGGCMAA/3IAbRQSp |
| SEQ ID NO. 201 | GAGAGGATGAYCAGCCACAC |
| SEQ ID NO. 202 | CGCCCATTGTSCAATATTCC |
| SEQ ID NO. 203 | 5TYE665/TGAGACACGGTCCAGACTCCTACG/3IAbRQSp |
| SEQ ID NO. 204 | AACTTTCACAGGTGTGCTGGGT |
| SEQ ID NO. 205 | CCGTACGCATACTGGCTTTGC |
| SEQ ID NO. 206 | 56-FAM/AAACCGGGC/ZEN/GATATGCGTCTGTAT/3IABkFQ |
| SEQ ID NO. 207 | CTGGGTTCTATAAGTAAAACCTTCACCGG |
| SEQ ID NO. 208 | CTTCCACTGCGGCTGCCAGTT |
| SEQ ID NO. 209 | 5HEX/GATGCCATT/ZEN/GCYCGSGGTGAAAT/3IABkFQ |
| SEQ ID NO. 210 | CCGAAGCCTATGGCGTGAAATCC |
| SEQ ID NO. 211 | GCAATGCCCTGCTGGAGCG |
| SEQ ID NO. 212 | 5TEX615/ATGTTGGCCTGAACCCAGCG/3IAbRQSp |
| SEQ ID NO. 213 | GAGAGGATGAYCAGCCACAC |
| SEQ ID NO. 214 | CGCCCATTGTSCAATATTCC |
| SEQ ID NO. 215 | 5TYE665/TGAGACACGGTCCAGACTCCTACG/3IAbRQSp |
| SEQ ID NO. 216 | AGCACATACAGAATATGTCCCTGC |
| SEQ ID NO. 217 | ACCTGTTAACCAACCTACTTGAGGG |
| SEQ ID NO. 218 | /56-FAM/TTGCAAGACGGACTGGCTTAGACC/3BHQ_1/ |
| SEQ ID NO. 219 | CCTGATCGGATTGGAGAACC |
| SEQ ID NO. 220 | CTACCTCTTGAATAGGCGTAACC |
| SEQ ID NO. 221 | /5TEX615/ACGTCGCGCAAGTTCCTGATAGAC/3IAbRQSp/ |
| SEQ ID NO. 222 | TAGTGACTGCTAATCCAAATCACAG |

TABLE 1-continued

| | Primer/Probe Sequence |
|---|---|
| SEQ ID NO. 223 | GCACGAGCAAGATCATTACCATAGC |
| SEQ ID NO. 224 | /5HEX/AGTTATCCAACAAGGCCAAACTCAACA/3BHQ_1/ |
| SEQ ID NO. 225 | GAGAGGATGAYCAGCCACAC |
| SEQ ID NO. 226 | CGCCCATTGTSCAATATTCC |
| SEQ ID NO. 227 | 5TYE665/TGAGACACGGTCCAGACTCCTACG/3IAbRQSp |
| SEQ ID NO. 228 | AATCACAGGGCGTAGTTGTG |
| SEQ ID NO. 229 | ACCCACCAGCCAATCTTAGG |
| SEQ ID NO. 230 | /5HEX/TAGCTTGATCGCCCTCGATTTGGG/3BHQ_1/ |
| SEQ ID NO. 231 | GTGGGATGGAAAGCCACG |
| SEQ ID NO. 232 | CACTTGCGGGTCTACAGC |
| SEQ ID NO. 233 | /56-FAM/TTACTTTGGGCGAAGCCATGCAAG/3BHQ_1/ |
| SEQ ID NO. 234 | CACCTATGGTAATGCTCTTGC, |
| SEQ ID NO. 235 | CTGGAACTGCTGACAATGCC |
| SEQ ID NO. 236 | /5TEX615/TGGGAGAAAGATATGACTTTAGGTGAGGCA/3IAbRQSp/ |
| SEQ ID NO. 237 | GAGAGGATGAYCAGCCACAC |
| SEQ ID NO. 238 | CGCCCATTGTSCAATATTCC |
| SEQ ID NO. 239 | 5TYE665/TGAGACACGGTCCAGACTCCTACG/3IAbRQSp |
| SEQ ID NO. 240 | AGATCAGTTGGGTGCACG |
| SEQ ID NO. 241 | TGCTTAATCAGTGAGGCACC |
| SEQ ID NO. 242 | /56-FAM/ATGAAGCCA/ZEN/TACCAAACGACGAGC/3IABkFQ/ |
| SEQ ID NO. 243 | CTGGAGCGAAAGATCCACTA |
| SEQ ID NO. 244 | ATCGTCCACCATCCACTG |
| SEQ ID NO. 245 | /5HEX/CCAGATCGG/ZEN/CGACAACGTCACC/3IABkFQ/ |
| SEQ ID NO. 246 | GAGAGGATGAYCAGCCACAC |
| SEQ ID NO. 247 | CGCCCATTGTSCAATATTCC |
| SEQ ID NO. 248 | 5TYE665/TGAGACACGGTCCAGACTCCTACG/3IAbRQSp |
| SEQ ID NO. 249 | CCGTGTATGTTCAGCTAT |
| SEQ ID NO. 250 | CTTATCCATCACGCCTTT |
| SEQ ID NO. 251 | /5TEX615/TATGATGTCGATACCGCCAAATACCA/3IAbRQSp/ |
| SEQ ID NO. 252 | CTGTATGTCAGCGATCAT |
| SEQ ID NO. 253 | GATGCCAGTTTGCTTATCC |
| SEQ ID NO. 254 | /56FAM/AAGTCTGGG/ZEN/TGAGAACGGTGTCTAT/3IABkFQ/ |
| SEQ ID NO. 255 | CAGTCAGTATGCGAGTTTC |
| SEQ ID NO. 256 | AAAATTCGCCAAGCCATC |
| SEQ ID NO. 257 | /5HEX/TGCATAAGC/ZEN/CAGTGCGTTTTTATAT/3IABkFQ/ |
| SEQ ID NO. 258 | GAGAGGATGAYCAGCCACAC |
| SEQ ID NO. 259 | CGCCCATTGTSCAATATTCC |
| SEQ ID NO. 260 | 5TYE665/TGAGACACGGTCCAGACTCCTACG/3IAbRQSp |

The present teachings provide a molecular assay. The present teachings may provide a qualitative (i.e. end point) molecular assay for the detection of family-specific KPC, ESBL, MBL, and ampC gene targets. The present teachings may provide a qualitative (i.e. end point) molecular assay for the detection of family-specific plasmid-mediated ampC β-lactamase genes. The present teachings may provide a qualitative (i.e. end point) molecular assay for the detection of OXA gene targets. Fluorescently-labeled DNA probes may be used for detection. The assay of the present teachings may provide for differentiation between a plasmid-mediated ampC β-lactamase gene from a chromosomal ampC β-lactamase gene; provided the two genes are not from the same chromosomal origin. The assay may involve extraction of DNA from bacterial cells. The assay may include subsequent PCR amplification. The assay may include gel-based detection.

In contrast, to traditional phenotypic methods which require 24-48 hours for data, the present teachings may provide for data generation in just hours or one hour. The total time required for DNA extraction, PCR set-up, amplification, and analysis may be around about 2 hours to about 3 hours. The sensitivity of the assay may be about 100%. The specificity of the assay may be about 100%. Therefore, the present teachings provide for fast and reliable detection. Implementation of such rapid assays have a positive impact for infection control and patient care.

The present teachings allow for the detection of multiple β-lactamase gene families. The β-lactamases may include all major β-lactamases including ampC types. For example, the present teachings may allow for identification of up to six to nine β-lactamase gene families. The β-lactamase gene families may include CMY, CTX-Ms, DHA, IMP, KPC, NDM, OXA and VIM. The AmpC β-lactamases gene families may include MOX, ACC, FOX, DHA, CMY and EBC.

The present teachings provide for a kit which allows for identification of at least nine β-lactamase gene families. The gene families may include: IMP-1-like, NDM-like, OXA-48-like, CTX-M-14-like, CTX-M-15-like, CMY-2-like, DHA-like, VIM-like, and KPC-like. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each target group. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes three multiplex primers-probes mix vials. The mix vials may provide for simultaneous real-time PCR amplification of all targets between three reaction tubes. PCR Mix 1 may amplify a first set of three gene families. For example, CMY-2, CTX-M-14, and CTX-M-15. PCR Mix 2 may amplify a second set of three gene families. For example, OXA-48, IMP, and VIM. PCR mix 3 may amplify a third set of gene families. For example, DHA, KPC, and NDM. The multiplex mix may also include an internal control (IC) in each mix. The kit may include three external DNA control vials or first control mix vial, a second control mix vial and a third control mix vial. The DNA control mix vial may contain synthetic DNA templates of the corresponding multiplex targets. The DNA control mixes may serve as a positive control for each multiplex reaction. The DNA control mix may contain stabilized bacteria with chromosomal or transmissible genetic elements in a sample matrix similar to a patient sample.

The present teachings provide for a kit which allows for identification of at least six plasmid-mediated ampC gene families. The gene families may include: MOX-like, DHA-like, ACC-like, EBC-like, FOX-like, and CMY-2-like. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes two multiplex primers-probes mix vials. The mix vials may provide for simultaneous real-time PCR amplification of all targets between two reaction tubes. PCR Mix 1 may amplify a first set of three gene families. For example, MOX, ACC and FOX. PCR Mix 2 may amplify a second set of three gene families. For example, DHA, EBC and CMY-2. The multiplex mix may also include an internal control (IC) in each mix. The kit may include two external DNA control vials or first control mix vial and a second control mix vial. The DNA control mix vial may contain synthetic DNA templates of the corresponding multiplex targets. The DNA control mixes may serve as a positive control for each multiplex reaction.

The present teachings provide for a kit which allows for identification of at least six OXA carbapenemase gene families. The gene families may include: OXA-23, OXA-24/40, OXA-48, OXA-51, OXA-58, and OXA-143. The gene families may include like gene families. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit may include one or more multiplex primer-probe mixes containing one or more primers and one or more probes. The multiplex primer-probe mix may be a 10×PCR mix. In one example, the kit includes two multiplex primers-probes mix vials. The mix vials may provide for simultaneous real-time PCR amplification of all targets between two reaction tubes. PCR Mix 1 may amplify a first set of three gene families. For example, OXA 143, OXA 23 and OXA 51. PCR Mix 2 may amplify a second set of three gene families. For example, OXA 24/40, OXA-48 and OXA-58. The multiplex mix may also include an internal control (IC) in each mix. The kit may include two external DNA control vials or first control mix vial and a second control mix vial. The DNA control mix vial may contain synthetic DNA templates of the corresponding multiplex targets. The DNA control mixes may serve as a positive control for each multiplex reaction.

In addition, the present teachings contemplate that the kit or kits of the present teachings may provide for the detection of a non-beta lactamase gene family. The kit or kits may provide for detection of plasmid-mediated mechanisms of antibiotic resistance for one more types/categories of antibiotics. For example, the kit may also provide for the detection of the MCR-1 gene which confers polymixin resistance. The kit or kits may include primer sequences, probe sequences, and a control sequence for detection of one or more non-beta lactamase gene family in addition to beta-lactamase genes. For example, a kit may provide for the detection of ampC genes families and a MCR-1 gene family.

Furthermore, the present teachings allow for the expansion of the detection of other β-lactamase gene families including TEM and SHV. The gene families may include like gene families. The kit may also include an endogenous internal control (IC) that targets a conserved region common in gram-negative bacteria to reduce false negatives due to PCR inhibition, DNA degradation, or poor extraction. It is contemplated that the endogenous internal control discriminates false negative samples from true negative samples due to but not limited to one or more of PCR inhibition, DNA degradation, and/or poor extraction. The kit may utilize sequence-specific primer pairs for the PCR amplification of each family. The kit may utilize fluorescently-labeled, target-specific DNA probes for detection by real-time PCR.

The kit or kits of the present teachings may include synthetic DNA oligonucleotide primers, target-specific DNA probes and DNA controls for the specified gene targets suspended in TE buffer, pH 8.0. The contents of the kit may be enclosed in vials. For example, the one or more 10×PCR mixes may be comprised of 275 μL. For example, the one or more control mixes may be comprised of 14 μL. For example, the contents of the kit may be sufficient for about 100 reactions total and about 12 reactions of the control DNA mix.

Detection of each target is based on the optical fluorescence of the fluorophore conjugated to each target-specific DNA probe. Any suitable fluorophore and nucleic acid sequence combination may be used. For example, the fluorophores may be selected from the group consisting of: FAM, HEX, TEX615 and TYE665.

The present teachings provide assays for the detection of β-lactamase gene families from a biological sample. The assays may be included in a kit or kits. The kit may provide for the detection of β-lactamase by various molecular biology technologies and platforms. The kit may include one or more primers and/or probes for the identification by polymerase chain reaction or microarray of one or more β-lactamase genes selected from the group consisting of: CMY, CTX-M, OXA, IMP, VIM, DHA, KPC, MOX, ACC, FOX, EBC, NDM, TEM, and SHV.

The kit may include one or more primers and/or probes for the identification by polymerase chain reaction or microarray of a non-beta lactamase gene family which confers antibiotic resistance. The kit may include one or more primers and/or probes for the identification by polymerase chain reaction or microarray of one or more MCR genes. The kit may include one or more primers and/or probes for the identification by polymerase chain reaction or microarray of a MCR-1 gene.

The kit may provide for detection of specified targets from crude biological samples such as blood, urine, plasma, feces, sputum, etc. The kit may provide for detection of specified targets directly from or extracted directly from crude biological samples including but not limited to blood, blood cultures, urine, plasma, feces, fecal swabs, peri-rectal/peri-anal swabs, sputum, and bacterial cultures.

The kit may be used for detection of specified targets from purified nucleic acid samples. The kit may be used for any nucleic acid amplification methodology. The kit may be used with conventional polymerase chain reaction. The kit may be used with real-time polymerase chain reaction. The kit may be used with digital droplet polymerase chain reaction. The kit may be used with detection by microarray technology. The kit may be used with fluorescence and/or infra-red probe-based detection chemistries. The kit may be used with intercalating dye-based detection chemistries. The kit may be used for detection of nucleic acid polymerase chain reaction amplicons ranging from 25 base pairs to 2000 base pairs.

The kit may include various reagents. The various reagents may be contained in various vials. The kit may include a primer set or primer sets. The primer set or primer sets may be labeled or unlabeled with a tracking dye or fluorophore. The kit may include probes. The kit may include a primer-probe mix. The kit may include controls. The kit may include magnesium chloride. The kit may include dNTPs. The kit may include DNA polymerase. The kit may include a tracking dye. The kit may include a composition containing a tracking dye. The kit may include a written protocol. The kit may include a customized master mix in a single tube, two tubes, three tubes, or four tubes containing all chemicals and enzymes necessary to run the PCR assay described herein. The kit may include freeze-dried or lyophilized reagents in a single assay tube or multiple assay tubes. The kit may provide for detection of nucleic acid and the kit reagents may be provided in any liquid form, pooled reaction mix, or lyophilized, freeze dried, or cryo-preserved format.

The kit may include a primer set. The primer set may include at least one primer pair. A primer pair may include a forward primer and a reverse primer. The primer set may include one pair of primers. The primer set may include more than one pair of primers. The primer set may include two pairs of primers. The primer set may include three pairs of primers. The primer set may include one to six pairs of primers. The primer set may include one to ten pairs of primers. The primer set may include up to 30 pairs of primers. The primer set may include up to 50 pairs of primers. The primer set may include up to 100 pairs of primers.

The kit may include a primer-probe mix. The primer-probe mix may include a primer set. The primer-probe mix may include one or more probes. Each pair of primers of the primer set may include a probe or set of probes. The primer-probe mix may include a pair of internal control primers. The pair of internal control primers may include a forward primer and a reverse primer. The primer-probe mix may include an internal control probe.

For example, a primer-probe mix may include one or more pairs of primers, one associated probe per primer pair and internal controls including a pair of primers and a probe. Preferably, the primer-probe mix is a multiplex mix including more than one pair of primers, a probe for each primer pair and internal controls. The multiplex mix may be used for the identification of more than one β-lactamase gene family. Each primer pair and probe may detect a different β-lactamase gene family. For example, three primer pairs and their associated three probes may be used for detection of three different β-lactamase gene families.

The DNA concentration range of each primer set in a PCR may be about 1 nM to about 10 μM (10,000 nM). One or more primers may be labeled with a florescent marker as a probe. The DNA concentration of each probe in a PCR may be about 1 nM to about 10,000 nM. The DNA concentration of each probe in a PCR may be about 10 to about 500 nM.

The kit may include at least one control. The kit may include one, two, three or four controls. The kit may include one or more negative controls. The negative control may include nucleic acid known to express a resistance gene other than the target gene of interest. The kit may include one or more positive controls. The one or more positive controls may be internal controls. The positive control may include nucleic acid known to express or contain the resistance gene. The kit may include an endogenous internal control to reduce false negatives due to PCR inhibition, DNA degradation, and/or poor extraction. It is contemplated that the endogenous internal control discriminates false negative samples from true negative samples due to but not limited to one or more of PCR inhibition, DNA degradation, and/or poor extraction. The endogenous internal control may target a conserved nucleotide sequence or sequences common to the Gram-negative bacteria genome. For example, the internal control may detect the 16S rRNA and/or 23S rRNA gene(s). The internal control may detect the 16S and/or 23S rRNA gene for *E. Coli, Pseudomonas, Acinetobacter, Klebsiella* and *Salmonella*.

The kit may include control vector in the control vial. One or more μls of the vector control may be added to a 25 μl reaction to get the working concentration. The DNA concentrations for each control vector may be equivalent to 0.1 copy to 2000 copies or 0.0000243 pg/uL to 0.0455 pg/uL. The DNA concentrations for each control vector may be equivalent to 10 copies to 5000 copies or 0.001 pg/uL to 0.5 pg/uL. Control vector concentrations may be as high as $1\times10(9)$ copies and any dilution thereof.

The assays of the present teachings may include the use of magnesium chloride. The kit may include magnesium chloride. The assay may be utilized with a concentration of about 2 mM to about 7 mM $MgCl_2$. Preferably, the concentration is about 3.0 mM to about 5.5 mM $MgCl_2$. More preferably, the concentration is 5.0 mM $MgCl_2$ for an assay for the detection of β-lactamase genes. More preferably the concentration is 5.0 mM $MgCl_2$ for an assay for the detection of ampC β-lactamase genes. More, preferably, the concentration is 5 mM $MgCl_2$ for an assay for the detection of OXA genes.

The assays of the present teachings may include the use of DNA polymerase. The kit may include DNA polymerase. The assay may be utilized with a concentration of about 0.25 U/25 ul reaction to about 3 U/25 ul reaction of DNA polymerase. Preferably, the concentration is 1.25 U/25 μl reaction DNA polymerase for an assay for the detection of β-lactamase genes. Preferably the concentration is 1.25 U/25 μl DNA polymerase for an assay for the detection of β-lactamase ampC genes. For example, the present teachings may utilize the PhilisaFAST® DNA polymerase.

The assays and methods of the present teachings may include a PCR cycling protocol. In one example, the cycling protocol comprises (1) 95° C. for 30 s; (2) 95° C. for 1 s; (3) 55° C. for 10 s; (4) 68° C. for 20 s; and repeating steps (2) to (4) for 40 cycles. In one example, the cycling protocol comprises (1) 95° C. for 30 s; (2) 95° C. for 6 s; (3) 66° C. for 10 s; and repeating steps (2) to (3) for 40 cycles. In one example, the cycling protocol includes a hot start of 98° C. for 30 s and 30 cycles of: 98° C. for 5 s, 60° C. for 10 s and 72° C. for 20 s. In one example, the cycling protocol includes using 98° C. for 30 s, followed by 30 cycles of 98° C. for 5 s, 60° C. for 10 s., and 72° C. for 25 s. In one example, the PCR protocols include a detection step where fluorescent signal is measured.

The kit may include one or more of the following: primer, probe and control. A mix of one or more of the following: primer, probe and internal control, may be enclosed in one container. A mix of one or more of the following: primer, probe and internal control, may be enclosed in more than one container. The container may be a vial. In one example, the kit includes 3 DNA control vials and 3 10× primer/probe mix vials. Nine antibiotic resistance gene families and one internal control may be identified with the vials. In one example, the kit includes 2 DNA control vials and 2 10× primer/probe mix vials. Six antibiotic resistance gene families and one internal control may be identified with the vials.

The present teachings allow for detection of the β-lactamase CMY-2 gene family from a biological sample. The present teachings provide for a kit including one or more primers and/or probes for the identification by multiplex real-time polymerase chain reaction of β-lactamase genes including the CMY-2-like gene family. The biological sample may include Gram-negative bacteria such as *Escherichia coli, Proteus mirabilis, Klebsiella pneumoniae, Klebsiella oxytoca, Serratia marcescens, Citrobacter freundii* and other *Citrobacter* species. The CMY-2-like genes detected may include CMY-2, CMY-4, CMY-6, CMY-7, CMY-12, CMY-14, CMY-15, CMY-16, CMY-18, CMY-21, CMY-22, CMY-23, CMY-24, CMY-25, CMY-26, CMY-27, CMY-28, CMY-29, CMY-30, CMY-31, CMY-32, CMY-33, CMY-34, CMY-35, CMY-37, CMY-38, CMY-39, CMY-40, CMY-41, CMY-42, CMY-43, CMY-44, CMY-45, CMY-46, CMY-47, CMY-48, CMY-49, CMY-50, CMY-51, CMY-53, CMY-54, CMY-55, CMY-56, CMY-57, CMY-58, CMY-59, CMY-60, CMY-61, CMY-62, CMY-63, CMY-64, CMY-65, CMY-66, CMY-67, CMY-68, CMY-69, CMY-71, CMY-72, CMY-73, CMY-75, CMY-76, CMY-77, CMY-78, CMY-79, CMY-80, CMY-81, CMY-84, CMY-85, CMY-86, CMY-87, CMY-89, CMY-90, CMY-96, CMY-97, CMY-99, CMY-102, CMY-103, CMY-104, CMY-105, CMY-107, CMY-108, CMY-110, CMY-111, CMY-112, CMY-113, CMY-114, CMY-115, CMY-116, CMY-117, CMY-118, CMY-119, CMY-121, CMY-122, CMY-124, CMY-125, CMY-126, CMY-127, CMY-128, CMY-129, CMY-130, CMY-131, CMY-132, CMY-133 and CMY-135.

The present teachings allow for the detection of the β-lactamase CTX-M gene family from a biological sample. The present teachings provide for a kit including one or more primers and/or probes for the identification by multiplex real-time polymerase chain reaction of β-lactamase genes including the CTX-M-14-like gene family. The biological sample may include Gram-negative bacteria such as *Klebsiella pneumoniae, Enterobacter cloacae, Escherichia coli, Salmonella enterica, Proteus mirabilis* and *Shigella* species. The CTX-M-14-like genes detected may include CTX-M-9, CTX-M-13, CTX-M-14, CTX-M-16, CTX-M-17, CTX-M-19, CTX-M-21, CTX-M-24, CTX-M-27, CTX-M-38, CTX-M-51, CTX-M-64, CTX-M-65, CTX-M-67, CTX-M-82, CTX-M-83, CTX-M-84, CTX-M-85, CTX-M-86, CTX-M-90, CTX-M-93, CTX-M-98, CTX-M-99, CTX-M-102, CTX-M-104, CTX-M-105, CTX-M-110, CTX-M-111, CTX-M-112, CTX-M-113, CTX-M-121, CTX-M-122, CTX-M-123, CTX-M-125, CTX-M-129, CTX-M-130, CTX-M-132, CTX-M-134, CTX-M-147, CTX-M-148 and CTX-M-159.

The present teachings allow for the detection of the β-lactamase CTX-M gene family from a biological sample.

The present teachings provide for a kit including one or more primers and/or probes for the identification by multiplex real-time polymerase chain reaction of β-lactamase genes including the CTX-M-15-like gene family. The biological sample may include Gram-negative bacteria such as *Escherichia coli, Klebsiella pneumoniae, Citrobacter freundii, Shigella* species and *Proteus mirabilis*. The CTX-M-15-like genes detected may include CTX-M-1, CTX-M-3, CTX-M-10, CTX-M-15, CTX-M-22, CTX-M-28, CTX-M-29, CTX-M-30, CTX-M-32, CTX-M-37, CTX-M-55, CTX-M-64, CTX-M-71, CTX-M-103, CTX-M-117, CTX-M-123, CTX-M-132, CTX-M-136, CTX-M-138, CTX-M-142, CTX-M-144, CTX-M-155, CTX-M-156, CTX-M-157, CTX-M-158, CTX-M-163, CTX-M-164, CTX-M-166 and CTX-M-172.

The present teachings allow for the detection of the β-lactamase DHA gene family from a biological sample. The present teachings provide for a kit including one or more primers and/or probes for the identification by multiplex real-time polymerase chain reaction of β-lactamase genes including the DHA-like family. The biological sample may include Gram-negative bacteria such as *Klebsiella pneumoniae, Morganella morganii, Escherichia coli, Enterobacter cloacae, Proteus mirabilis* and *Citrobacter koseri*. The DHA-like genes detected may include DHA-1, DHA-2, DHA-5, DHA-6, DHA-7, DHA-9, DHA-10, DHA-12, DHA-13, DHA-14, DHA-15, DHA-16, DHA-17, DHA-18, DHA-19, DHA-20, DHA-21 and DHA-22.

The present teachings allow for the detection of the β-lactamase IMP gene family from a biological sample. The present teachings provide for a kit including one or more primers and/or probes for the identification by multiplex real-time polymerase chain reaction of β-lactamase genes including the IMP-like family. The biological sample may include Gram-negative bacteria such as *Serratia marcescens, Escherichia coli* and *Pseudomonas aeruginosa*. The IMP-like genes detected may include IMP-1, IMP-2, IMP-3, IMP-4, IMP-5, IMP-6, IMP-7, IMP-8, IMP-9, IMP-10, IMP-13, IMP-14, IMP-15, IMP-16, IMP-18, IMP-19, IMP-20, IMP-22, IMP-24, IMP-25, IMP-26, IMP-27, IMP-28, IMP-30, IMP-32, IMP-33, IMP-34, IMP-37, IMP-38, IMP-40, IMP-42, IMP-45, IMP-48, IMP-49, IMP-51 and IMP-52.

The present teachings allow for the detection of the β-lactamase KPC gene family from a biological sample. The present teachings provide for a kit including one or more primers and/or probes for the identification by multiplex real-time polymerase chain reaction of β-lactamase genes including the KPC-like family. The biological sample may include Gram-negative bacteria such as *Klebsiella pneumoniae, Escherichia coli, Enterobacter cloacae* and other *Enterobacter* species, *Pseudomonas aeruginosa* and *Acinetobacter baumannii*. The KPC-like genes detected may include KPC-1, KPC-2, KPC-3, KPC-4, KPC-5, KPC-6 KPC-7, KPC-8, KPC-9, KPC-10, KPC-11, KPC-13, KPC-14, KPC-15, KPC-16, KPC-17 KPC-18, KPC-19, KPC-21, KPC-22, KPC-47, KPC-56, KPC-63, KPC-272, KPC-484, KPC-629, KPC-727, and KPC-860.

The present teachings allow for the detection of the β-lactamase NDM gene family from a biological sample. The present teachings provide for a kit including one or more primers and/or probes for the identification by multiplex real-time polymerase chain reaction of β-lactamase genes including the NDM-like family. The biological sample may include Gram-negative bacteria such as *Escherichia coli, Acinetobacter baumannii, Enterobacter cloacae* and *Klebsiella pneumoniae*. The NDM-like genes detected may include NDM-1, NDM-2, NDM-3, NDM-4, NDM-5, NDM-6, NDM-7, NDM-8, NDM-9, NDM-10, NDM-11, NDM-12, NDM-13, NDM-15, NDM-16 and NDM-32.

The present teachings allow for the detection of the β-lactamase OXA gene family from a biological sample. The present teachings provide for a kit including one or more primers and/or probes for the identification by multiplex real-time polymerase chain reaction of β-lactamase genes including the OXA-48-like family. The biological sample may include Gram-negative bacteria such as *Klebsiella pneumoniae, Enterobacter cloacae, Shewanella xiamenensis, Escherichia coli* and *Serratia marcescens*. The OXA-48-like genes detected may include OXA-48, OXA-162, OXA-163, OXA-181, OXA-199, OXA-204, OXA-232, OXA-244, OXA-245, OXA-247, OXA-370, OXA-405, OXA-416, OXA-438 and OXA-439.

The present teachings provide for a kit including one or more primers and/or probes for the identification by multiplex real-time polymerase chain reaction of β-lactamase genes including one or more of the following: OXA-143-like, OXA-23-like, OXA-51-like, OXA-48-like, OXA-58-like and OXA24/40-like. The OXA-143-like genes detected may include the following: OXA-143, OXA-182, OXA-231, OXA-253, and OXA-255. The OXA-23-like genes detected may include the following: OXA-23, OXA-27, OXA-49, OXA-73, OXA-102, OXA-103, OXA-105, OXA-133, OXA-134, OXA-146, OXA-165, OXA-166, OXA-167, OXA-168, OXA-169, OXA-170, OXA-171, OXA-225 and OXA-239. The OXA-51-like genes detected may include the following: OXA-51, OXA-64, OXA-65, OXA-66, OXA-67, OXA-68, OXA-69, OXA-70, OXA-71, OXA-75, OXA-76, OXA-77, OXA-78, OXA-79, OXA-80, OXA-82, OXA-83, OXA-84, OXA-86, OXA-87, OXA-88, OXA-89, OXA-90, OXA-91, OXA-92, OXA-93, OXA-94 OXA-95, OXA-98, OXA-99, OXA-100, OXA-104, OXA-106, OXA-107, OXA-108, OXA-109, OXA-110, OXA-111, OXA-112, OXA-113, OXA-115, OXA-116, OXA-117, OXA-120, OXA-121, OXA-122, OXA-123, OXA-124, OXA-125, OXA-126, OXA-127, OXA-128, OXA-130, OXA-131, OXA-132, OXA-138, OXA-144, OXA-148, OXA-149, OXA-150, OXA-172, OXA-173, OXA-174, OXA-175, OXA-176, OXA-177, OXA-178, OXA-179, OXA-180, OXA-194, OXA-195, OXA-196, OXA-197, OXA-200, OXA-201, OXA-202, OXA-203, OXA-206, OXA-208, OXA-216, OXA-217, OXA-219, OXA-223, OXA-241, OXA-242, OXA-248, OXA-249, OXA-250 and OXA-254. The OXA-48-like genes detected may include the following: OXA-48, OXA-48b, OXA-162, OXA-163, OXA-181, OXA-199, OXA-204, OXA-232, OXA-244, OXA-245 and OXA-247. The OXA-58-like genes may include the following: OXA-58, OXA-96, OXA-97 and OXA-164. The OXA-40-like genes may include the following: OXA-40, OXA-25, OXA-26, OXA-72, OXA-139, OXA-160 and OXA-207.

The present teachings allow for the detection of the β-lactamase VIM gene family from a biological sample. The present teachings provide for a kit including one or more primers and/or probes for the identification by multiplex real-time polymerase chain reaction of β-lactamase genes including the VIM-like family. The biological sample may include Gram-negative bacteria such as *Klebsiella oxytoca, Citrobacter freundii, Klebsiella pneumoniae, Pseudomonas aeruginosa, Escherichia coli* and *Enterobacter cloacae*. The VIM-like genes detected may include VIM-1, VIM-2, VIM-3, VIM-4, VIM-5, VIM-6, VIM-8, VIM-9, VIM-10, VIM-11, VIM-12, VIM-13, VIM-14, VIM-15, VIM-16, VIM-17, VIM-18, VIM-19, VIM-20, VIM-23, VIM-24, VIM-25, VIM-26, VIM-27, VIM-28, VIM-31, VIM-33, VIM-34, VIM-35, VIM-36, VIM-37, VIM-38, VIM-39, VIM-40, VIM-41, VIM-42, VIM-43, VIM-44, VIM-45 and VIM-46.

The present teachings allow for the detection of the AmpC β-lactamase MOX gene family from a biological sample. The present teachings provide for a kit including one or more primers and/or probes for the identification by multiplex real-time polymerase chain reaction of β-lactamase genes including the MOX-like family. The biological sample may include Gram-negative bacteria such as *Klebsiella pneumoniae, Aeromonas punctata/Aeromonas caviae* and other *Aeromonas* species and *Escherichia coli*. The MOX-like genes detected may include MOX-1, MOX-2, MOX-3, MOX-4, MOX-5, MOX-6, MOX-7, MOX-8, MOX-10, CMY-1, CMY-8, CMY-9, CMY-10, CMY-11 and CMY-19.

The present teachings allow for the detection of the AmpC β-lactamase ACC gene family from a biological sample. The present teachings provide for a kit including one or more primers and/or probes for the identification by multiplex real-time polymerase chain reaction of β-lactamase genes including the ACC-like family. The biological sample may include Gram-negative bacteria such as *Salmonella enterica, Escherichia coli, Hafnia alvei* and *Proteus mirabilis*. The ACC-like genes detected may include ACC-1, ACC-2, ACC-4, ACC-5 and ACC-6.

The present teachings allow for the detection of the AmpC β-lactamase FOX gene family from a biological sample. The present teachings provide for a kit including one or more primers and/or probes for the identification by multiplex real-time polymerase chain reaction of β-lactamase genes including the FOX-like family. The biological sample may include Gram-negative bacteria such as *Klebsiella pneumoniae* and *Aeromonas punctata*. The FOX-like genes detected may include FOX-1, FOX-2, FOX-3, FOX-4, FOX-5, FOX-6, FOX-7, FOX-8, FOX-9, FOX-10 and FOX-12.

The present teachings allow for the detection of the AmpC β-lactamase DHA gene family from a biological sample. The present teachings provide for a kit including one or more primers and/or probes for the identification by multiplex real-time polymerase chain reaction of β-lactamase genes including the DHA-like family. The biological sample may include Gram-negative bacteria such as *Klebsiella pneumoniae, Morganella morganii, Escherichia coli* and *Enterobacter cloacae*. The DHA-like genes detected may include DHA-1, DHA-2, DHA-5, DHA-6, DHA-7, DHA-9, DHA-10, DHA-12, DHA-13, DHA-14, DHA-15, DHA-16, DHA-17, DHA-18, DHA-19, DHA-20, DHA-21 and DHA-22.

The present teachings allow for the detection of the AmpC β-lactamase CMY-2 gene family from a biological sample. The present teachings provide for a kit including one or more primers and/or probes for the identification by multiplex real-time polymerase chain reaction of β-lactamase genes including the CMY-2-like family. The biological sample may include Gram-negative bacteria such as *Klebsiella pneumoniae, Morganella morganii, Escherichia coli* and *Enterobacter cloacae*. The CMY-2-like genes detected include CMY-2, CMY-4, CMY-6, CMY-7, CMY-12, CMY-14, CMY-15, CMY-16, CMY-18, CMY-21, CMY-22, CMY-23, CMY-24, CMY-25, CMY-26, CMY-27, CMY-28, CMY-29, CMY-30, CMY-31, CMY-32, CMY-33, CMY-34, CMY-35, CMY-37, CMY-38, CMY-39, CMY-40, CMY-41, CMY-42, CMY-43, CMY-44, CMY-45, CMY-46 CMY-47, CMY-48, CMY-49, CMY-50, CMY-51, CMY-53, CMY-54, CMY-55, CMY-56, CMY-57, CMY-58, CMY-59, CMY-60, CMY-61, CMY-62, CMY-63, CMY-64, CMY-65, CMY-66, CMY-67, CMY-68, CMY-69, CMY-71, CMY-72, CMY-73, CMY-75, CMY-76, CMY-77, CMY-78, CMY-79, CMY-80, CMY-81, CMY-84, CMY-85 CMY-86, CMY-87, CMY-89, CMY-90, CMY-96, CMY-97, CMY-99, CMY-102, CMY-103, CMY-104 CMY-105, CMY-107, CMY-108, CMY-110, CMY-111, CMY-112, CMY-113, CMY-114, CMY-115 CMY-116, CMY-117, CMY-118, CMY-119, CMY-121, CMY-122, CMY-124, CMY-125, CMY-126, CMY-127, CMY-128, CMY-129, CMY-130, CMY-131 CMY-132, CMY-133 and CMY-135.

The present teachings allow for the detection of the AmpC β-lactamase EBC gene family from a biological sample. The present teachings provide for a kit including one or more primers and/or probes for the identification by multiplex real-time polymerase chain reaction of β-lactamase genes including the EBC-like family such as ACT and MIR. The biological sample may include Gram-negative bacteria such as *Enterobacter cloacae, Klebsiella pneumoniae, Enterobacter asburiae, Enterobacter kobei*, and other *Enterobacter* species. The EBC-like genes detected may include ACT-1, ACT-2, ACT-5, ACT-8, ACT-13, ACT-14, ACT-15, ACT-16, ACT-17, ACT-18, ACT-20, ACT-21, ACT-23, ACT-24, ACT-25, ACT-27, ACT-29, ACT-30, ACT-31, ACT-32, ACT-33, ACT-34, ACT-35, ACT-36, ACT-37, ACT-38, MIR-1, MIR-2, MIR-3, MIR-4, MIR-6, MIR-7, MIR-8, MIR-9, MIR-10, MIR-11, MIR-12, MIR-13, MIR-14, MIR-15, MIR-16, MIR-17 and MIR-18.

The present teachings may allow for the detection of the β-lactamase TEM gene family from a biological sample. The present teachings provide for a kit including one or more primers and/or probes for the identification by multiplex real-time polymerase chain reaction of β-lactamase genes including the TEM-like family. The biological sample may include Gram-negative bacteria such as *Klebsiella pneumoniae, Enterobacter cloacae, Shewanella xiamenensis, Escherichia coli* and *Serratia marcescens*. The TEM-like genes detected may include TEM-1, TEM-2, TEM-3, TEM-15, TEM-20, TEM-32, TEM-40, TEM-52, TEM-88, TEM-91, TEM-97, TEM-98, TEM-106, TEM-107, TEM-112, TEM-120, TEM-126, TEM-135, TEM-141, TEM-150, TEM-153, TEM-163, TEM-168, TEM-170, TEM-171, TEM-206, TEM-214, and TEM-220.

The present teachings may allow for the detection of the β-lactamase SHV gene family from a biological sample. The present teachings provide for a kit including one or more primers and/or probes for the identification by multiplex real-time polymerase chain reaction of β-lactamase genes including the SHV-like family. The biological sample may include Gram-negative bacteria such as *Klebsiella pneumoniae, Enterobacter cloacae, Shewanella xiamenensis, Escherichia coli* and *Serratia marcescens*. The SHV-like genes detected may include SVH-1, SHV-2, SHV-3, SHV-5, SHV-7, SHV-8, SHV-9, SHV-11, SHV-12, SHV-13, SHV-14, SHV-15, SHV-16, SHV-18, SHV-24, SHV-25, SHV-26, SHV-27, SHV-28, SHV-29, SHV-30, SHV-31, SHV-32, SHV-33, SHV-34, SHV-35, SHV-36, SHV-37, SHV-38, SHV-40, SHV-41, SHV-42, SHV-43, SHV-44, SHV-45, SHV-46, SHV-48, SHV-49, SHV-50, SHV-51, SHV-52, SHV-53, SHV-55, SHV-56, SHV-57, SHV-59, SHV-60, SHV-61, SHV-62, SHV-63, SHV-64, SHV-65, SHV-66, SHV-67, SHV-69, SHV-70, SHV-71, SHV-72, SHV-73, SHV-74, SHV-75, SHV-76, SHV-77, SHV-78, SHV-79, SHV-80, SHV-81, SHV-82, SHV-85, SHV-86, SHV-89, SHV-92, SHV-93, SHV-94, SHV-95, SHV-96, SHV-97, SHV-98, SHV-99, SHV-100, SHV-101, SHV-102, SHV-103, SHV-104, SHV-105, SHV-106, SHV-107, SHV-109, SHV-110, SHV-111, SHV-119, SHV-120, SHV-121, SHV-122, SHV-123, SHV-124, SHV-125, SHV-126, SHV-127, SHV-128, SHV-129, SHV-132, SHV-133, SHV-134, SHV-135, SHV-136, SHV-137, SHV-140, SHV-141, SHV-142, SHV-143, SHV-144, SHV-145, SHV-146, SHV-147, SHV-148, SHV-149, SHV-150, SHV-151, SHV-152, SHV-153, SHV-154, SHV-155, SHV-156, SHV-157, SHV-158, SHV-159, SHV-160, SHV-161, SHV-162, SHV-163, SHV-164, SHV-165, SHV-168, SHV-172, SHV-173, SHV-178, SHV-179, SHV-180, SHV-182, SHV-183, SHV-185, SHV-186, SHV-187, SHV-188, SHV-189, SHV-190, SHV-191, SHV-193, SHV-194, SHV-195, SHV-196, and SHV-197.

The present teachings may allow for the detection of the MCR gene family from a biological sample. The present teachings provide for a kit including one or more primers and/or probes for the identification by multiplex real-time polymerase chain reaction of MCR genes including the MCR-like family. The MCR-like genes detected may include MCR-1, MCR-1.2, MCR-1.3, MCR-1.4, MCR-1.5, MCR-1.6, MCR-1.7, MCR-1.8, MCR-1.9 and MCR-2.

The kit of the present teachings may include a mix of at least one primer and/or at least one probe. Primers and/or probes may be degenerate at any nucleotide position. Primers and/or probes may not be degenerate at any nucleotide position. A hydrolysis and/or hybridization probe may be designed for the detection of a specific nucleic acid sequence. Multiple probes may be labeled with a different colored fluorophore. The probe may be labeled with a fluorescent tag at one end and a fluorescent quencher at the other end. Two fluorescent quenchers may be included at one end or within the probe sequence. For example, the fluorophores may be selected from the group consisting of fluorescein, hexachlorofluorescein, TEX 615, and TYE™ 665. The fluorophores may excite between 450 nm and 763 nm and emit between 500 nm and 800 nm. For example, the quenchers may be selected from the group consisting of Iowa Black® quenchers and Black Hole Quenchers®. Peak absorbance of each quencher may be at 531 nm, 534 nm, 578 nm, or 656 nm.

Multiple hydrolysis and/or hybridization probes can be added to the same nucleic acid amplification reaction. The selection of the fluorescent labels may depend on the type of hydrolysis and/or hybridization probe used, the number of targets to be detected and the type of thermal cycler used. Preferable combinations of fluorophores and quenchers for multiplex reactions require appropriate excitation wavelengths and little to no overlap in their emission spectra as well as reduction of background fluorescence. It is contemplated that the probe sequences of the present teachings may be labeled with any suitable fluorophore and quencher combinations. For example, any fluorophore of the present teachings may be attached to any probe DNA sequence of the present teachings.

The one or more primers and/or probes maybe selected from the group consisting of: TGGCCAGAACTGACAGGCAAA, TTTCTCCTGAACGTGGCTGGC, 56-FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC, 5TEX615/TATCATTGGTGGTGCCGTAGTCGC/3IAbRQSp, GAGAGGATGAYCAGCCACAC, CGCCCATTGTSCAATATTCC, 5TYE665/TGAGACACGGTCCAGACTCCTACG/3IAbRQSp, AATCACAGGGCGTAGTTGTG, ACCCACCAGCCAATCTTAGG, 56-FAM/TAGCTTGAT/ZEN/CGCCCTCGATTTGGG/3IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ/, GGCGGCGTTGATGTCCTTCG, CCATTCAGCCAGATCGGCATC, 5TEX615/AGCTCTTCTATCCTGGTGCTGCG/3IAbRQSp, AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG, 5TEX615/CATCAGGACAAGATGGGCGGTATG/3IAbRQSp, GCTGCTCAAGGAGCACAGGAT, CACATTGACATAGGTGTGGTGC, 56-FAM/AGGATGGCA/ZEN/AGGCCCACTATTTCA/3IABkFQ, AACAGCCTCAGCAGCCGGTTA, TTCGCCGCAATCATCCCTAGC, 5HEX/AGCCATTAC/ZEN/GTTCCAGAGTTGCGT/3IABkFQ, GCCGAGGCTTACGGGATCAAG, CAAAGCGCGTAACCGGATTGG, 5TEX615/TCTGCTGAAGTTTRYCGAGGCMAA/3IAbRQSp, AACTTTCACAGGTGTGCTGGGT, CCGTACGCATACTGGCTTTGC, 56-FAM/AAACCGGGC/ZEN/GATATGCGTCTGTAT/3IABkFQ/, CTGGGTTCTATAAGTAAAACCTTCACCGG, CTTCCACTGCGGCTGCCAGTT, 5HEX/GATGCCATT/ZEN/GCYCGSGGTGAAAT/3IABkFQ, CCGAAGCCTATGGCGTGAAATCC, GCAATGCCCTGCTGGAGCG, 5TEX615/ATGTTGGCCTGAACCCAGCG/3IAbRQSp.

Primers and/or probes included in this group may or may not be degenerate at any nucleotide position. [SEQ. ID NOS 67-118]

The kit may include one or more primer-probe multiplex mixes. The primer-probe multiplex mix may include one or more internal controls. The primer-probe multiplex mix and one or more internal controls may be enclosed in one container, such as a vial. The primer-probe multiplex mix and one or more internal controls may be enclosed in more than one container, such as vials.

A primer-probe mix may include sequences for detecting any combination of the following genes: CMY-2-like, CTX-M-14-like, CTX-M-15-like, IMP-like, VIM-like, DHA-like, KPC-like, NDM-like, MOX-like, ACC-like, FOX-like, DHA-like, EBC-like, OXA-143-like, OXA-23-like, OXA-51-like, OXA-48-like, OXA-58-like and OXA-24/40-like.

For example, the kit may include a first primer-probe mix and one or more internal controls in a first vial and a second primer-probe mix and one or more internal controls in a second vial. For example, the kit may include a first primer-probe mix and one or more internal controls in a first vial, a second primer-probe mix and one or more internal controls in a second vial and a third primer-probe mix and one or more internal controls in a third vial. Each vial may contain different mixtures. Each vial may contain the same mixture.

The kit may include at least one control DNA mix. The kit may include one or more DNA control mixes. The kit may include exactly two control DNA mixes. The kit may include exactly three control DNA mixes. The DNA control mix may include at least one DNA sequence corresponding to at least one gene family and at least one internal control DNA sequence. The DNA control mix may be enclosed in one container, such as a vial. The DNA control mix may be enclosed in more than one container, such as vials.

For example, the kit may include a first DNA control mix in a first vial and a second DNA control mix in a second vial. For example, the kit may include a first DNA control mix in a first vial, a second DNA control mix in a second vial and a third DNA control mix in a third vial. Each vial may contain different mixtures. Each vial may contain the same mixture.

In one example, the kit includes three primer-probe multiplex mix vials including internal controls and three DNA control mix vials. The three primer-probe multiplex mixes may provide for identification of up to nine antibiotic resistance genes and internal controls. A first primer-probe mix may include sequences for detecting gene families which are CMY-2-like, CTX-M-14-like, CTX-M-15-like and internal controls. A second primer-probe mix may include sequences for detecting gene families which are OXA-48-like, IMP-like, VIM-like and internal controls. A third primer-probe mix may include sequences for detecting gene families which are DHA-like, KPC-like, NDM-like and internal controls. The one or more DNA control mixes may be plasmid or vector controls. A first DNA control mix may include DNA sequences for CMY-2, CTX-M-14, CTX-M-15 and an internal control DNA sequence. A second DNA control mix may include DNA sequences for OXA-48, IMP, VIM and an internal control DNA sequence. A third DNA control mix may include DNA sequences for DHA, KPC, NDM and an internal control DNA sequence.

It is contemplated that the combination of gene families may vary. For example, a primer-probe mix may include sequences for detecting any combination of the following genes: CMY-2-like, CTX-M-14-like, CTX-M-15-like, and OXA-48-like, IMP-like, VIM-like, DHA-like, KPC-like and NDM-like. It is further contemplated that additional β-lactamase gene targets may be included in the primer-probe mix or mixes.

The first primer-probe mix may include one or more primers and/or probes selected from the group consisting of: TGGCCAGAACTGACAGGCAAA, TTTCTCCTGAACGTGGCTGGC, 56FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC and 5TEX615/TATCATTGGTGGTGCCGTAGTCGC/3IAbRQSp. The first primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 152-163]

The kit may include a first, second and third primer and/or probe mix, the first primer and/or probe mix including one or more primers and/or probes selected from the group consisting of: TGGCCAGAACTGACAGGCAAA, TTTCTCCTGAACGTGGCTGGC, 56-FAM/ACGCTAACT/ZEN/CCAGCATTGGTCTGT/3IABkFQ/, CCGTCACGCTGTTGTTAGG, GCTGTGTTAATCAATGCCACAC, 5HEX/AACTTGCCG/ZEN/AATTAGAGCRGCAGT/3IABkFQ, CGTTTCGTCTGGATCGCAC, GCTGGGTAAAATAGGTCACC, 5TEX615/TATCATTGGTGGTGCCGTAGTCGC/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 152-163]

The second primer-probe mix may include one or more primers and/or probes selected from the group consisting of: AATCACAGGGCGTAGTTGTG, ACCCACCAGCCAATCTTAGG, 56-FAM/TAGCTTGAT/ZEN/CGCCCTCGATTTGGG/3IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ, GGCGGCGTTGATGTCCTTCG, CCATTCAGCCAGATCGGCATC and 5TEX615/AGCTCTTCTATCCTGGTGCTGCG/3IAbRQSp. The second primer-probe mix may include one or more internal controls selected from the group consisting of: GAGAGGATGAYCAGCCACAC, CGCCCATTGTSCAATATTCC, and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 164-179]

The kit may include a first, second, and third primer and/or probe mix, the second primer and/or probe mix including one or more primers and/or probes selected from the group consisting of: AATCACAGGGCGTAGTTGTG, ACCCACCAGCCAATCTTAGG, 56-FAM/TAGCTTGAT/ZEN/CGCCCTCGATTTGGG/13IABkFQ/, GCGGAGTTAACTATTGGCTAG, GGCCAAGCTTCTATATTTGCG, 5HEX/TTRTTYGGT/ZEN/GGTTGYTTTRTTAA/3IABkFQ, GCGGAGTTARYTATTGGCTAG, GGCCAAGCYTCTAWATTTGCG, /5HEX/CCGGACGGT/ZEN/CTTGGTAATTTGGGT/3IABkFQ/, /5HEX/CCGTACGGT/ZEN/TTAGGCAATTTGGGT/3IABkFQ, GGCGGCGTTGATGTCCTTCG, CCATTCAGCCAGATCGGCATC, 5TEX615/AGCTCTTCTATCCTGGTGCTGCG/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 164-179]

The third primer-probe mix may include one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG and 5TEX615/CATCAGGACAAGATGGGCGGTATG/3IAbRQSp. The third primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 180-191]

The kit may include a first, second and third primer and/or probe mix, the third primer and/or probe mix including one or more primers and/or probes selected from the group consisting of: AACTTTCACAGGTGTGCTGGGT, CCGTACGCATACTGGCTTTGC, 56-FAM/AAACCGGGC/ZEN/GATATGCGTCTGTAT/3IABkFQ/, GTATCGCCGTCTAGTTCTGC, CCTTGAATGAGCTGCACAGTGG, 5HEX/TCGTCGCGG/ZEN/AACCATTCGCTAAA/3IABkFQ/, GTTTGATCGTCAGGGATGGC, GGCGAAAGTCAGGCTGTG, 5TEX615/CATCAGGACAAGATGGGCGGTATG/3IAbRQSp, GAGAGGATGAYCAGCCACAC, CGCCCATTGTSCAATATTCC, and 5TYE665/TGAGACACGGTCCAGACTCCTACG/3IAbRQSp. Primers and/or probes included in this group may or may not be degenerate at any nucleotide position. [SEQ. ID NOS 180-191]

A first DNA control mix may include one or more sequences selected from the group consisting of: TGGCCAGAACTGACAGGCAAACAGTGGCAGGGTATCCGCCTGCTGCACTTAGCCA CCTATACGGCAGGCGGCCTACCGCTGCAGATCCCCGATGACGTTAGGGATAAAGC CGCATTACTGCATTTTTATCAAAACTGGCAGCCGCAATGGACTCCGGGCGCTAAGC GACTTTACGCTAACTCCAGCATTGGTCTGTTTGGCGCGCTGGCGGTGAAACCCTC AGGAATGAGTTACGAAGAGGCAATGACCAGACGCGTCCTGCAACCATTAAAACTG GCGCATACCTGGATTACGGTTCCGCAGAACGAACAAAAAGATTATGCCTGGGGCT ATCGCGAAGGGAAGCCCGTACACGTTTCTCCGGGACAACTTGACGCCGAAGCCTA TGGCGTGAAATCCAGCGTTATTGATATGGCCCGCTGGGTTCAGGCCAACATGGAT GCCAGCCACGTTCAGGAGAAA, CCGTCACGCTGTTGTTAGGAAGTGTGCCGCTGTATGCGCAAACGGCGGACGTACA GCAAAAACTTGCCGAATTAGAGCGGCAGTCGGGAGGCAGACTGGGTGTGGCATT GATTAACACAGC, and CGTTTCGTCTGGATCGCACTGAACCTACGCTGAATACCGCCATTCCCGGCGACCC GAGAGACACCACCACGCCGCGGGCGATGGCGCAGACGTTGCGTCAGCTTACGCT GGGTCATGCGCTGGGCGAAACCCAGCGGGCGCAGTTGGTGACGTGGCTCAAAGG CAATACGACCGGCGCAGCCAGCATTCGGGCCGGCTTACCGACGTCGTGGACTGT GGGTGATAAGACCGGCAGCGGCGACTACGGCACCACCAATGATATTGCGGTGATC TGGCCGCAGGGTCGTGCGCCGCTGGTTCTGGTGACCTATTTTACCCAGC. The first DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 261-264]

A second DNA control mix may include one or more sequences selected from the group consisting of: AATCACAGGGCGTAGTTGTGCTCTGGAATGAGAATAAGCAGCAAGGATTTACCAAT AATCTTAAACGGGCGAACCAAGCATTTTTACCCGCATCTACCTTTAAAATTCCCAAT AGCTTGATCGCCCTCGATTTGGGCGTGGTTAAGGATGAACACCAAGTCTTTAAGTG GGATGGACAGACGCGCGATATCGCCACTTGGAATCGCGATCATAATCTAATCACC GCGATGAAATATTCAGTTGTGCCTGTTTATCAAGAATTTGCCCGCCAAATTGGCGA GGCACGTATGAGCAAGATGCTACATGCTTTCGATTATGGTAATGAGGACATTTCGG GCAATGTAGACAGTTTCTGGCTCGACGGTGGTATTCGAATTTCGGCCACGGAGCAAATCAGCTTTTTAAGAAAGCTGTATCACAATAAGTTACACGTATCGGAGCGCAGCC AGCGTATTGTCAAACAAGCCATGCTGACCGAAGCCAATGGTGACTATATTATTCGG GCTAAAACTGGATACTCGACTAGAATCGAACCTAAGATTGGCTGGTGGGT, GCGGAGTTAGTTATTGGCTAGTTAAAAATAAAATTGAAGTTTTTTATCCCGGCCCGGGGCACACTCAAGATAACGTAGTGGTTTGGTTACCTGAAAAGAAAATTTTATTCGGT GGTTGTTTTGTTAAACCGGACGGTCTTGGTAATTTGGGTGACGCAAATTTAGAAGC TTGGCC and GGCGGCGTTGATGTCCTTCGGGCGGCTGGGGTGGCAACGTACGCATCACCGTCG ACACGCCGGCTAGCCGAGGTAGAGGGAACGAGATTCCCACGCACTCTCTAGAA GGACTCTCATCGAGCGGGGACGCAGTGCGCTTCGGTCCAGTAGAACTCTTCTATC CTGGTGCTGCGCATTCGACCGACAACTTAGTTGTGTACGTCCCGTCTGCGAGTGT GCTCTATGGTGGTTGTGCGATTCATGAGTTGTCACGCACGTCTGCGGGGAACGTG GCCGATGCCGATCTGGCTGAATGG. The second DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 265-268]

A third DNA control mix may include one or more sequences selected from the group consisting of: AACTTTCACAGGTGTGCTGGGTGCGGTTTCTGTGGCGAAAAAAGAGATGGCGCTG AATGATCCGGCGGCAAAATACCAGCCGGAGCTGGCTCTGCCGCAGTGGAAGGGG ATCACATTGCTGGATCTGGCTACCTATACCGCAGGCGGACTGCCGTTACAGGTGC CGGATGCGGTAAAAAGCCGTGCGGATCTGCTGAATTTCTATCAGCAGTGGCAGCC GTCCCGGAAACCGGGCGATATGCGTCTGTATGCAAACAGCAGTATCGGCCTGTTT GGTGCTCTGACCGCAAACGCGGCGGGGATGCCGTATGAGCAGTTGCTGACTGCA CGGATCCTGGCACCGCTGGGGTTATCTCACACCTTTATTACTGTGCCGGAAAGTG CGCAAAGCCAGTATGCGTACGG, GTATCGCCGTCTAGTTCTGCTGTCTTGTCTCTCATGGCCGCTGGCTGGCTTTTCTG CCACCGCGCTGACCAACCTCGTCGCGGAACCATTCGCTAAACTCGAACAGGACTT TGGCGGCTCCATCGGTGTGTACGCGATGGA TACCGGCTCAGGCGCAACTGTAAGT
TACCGCGCTGAGGAGCGCTTCCCACTGTGCAGCT-CATTCAAGG and GTTTGATCGTCAGG-GATGGCGGCCGCGTGCTGGTGGTCGA-TACCGCCTGGACCG
ATGACCAGACCGCCCAGATCCTCAACTGGAT-CAAGCAGGAGATCAACCTGCCGGT
CGCGCTGGCGGTGGTGACTCACGCG-CATCAGGACAAGATGGGCGGTATGGACGC GCTG-CATGCGGCGGGGATTGCGACTTATGC-CAATGCGTTGTCGAACCAGCTTGCC
CCGCAAGAGGG-GATGGTTGCGGCGCAACACAGCCTGACTTTCGCC.
The third DNA control mix may include the following internal control sequence: GAGAGGATGACCAGC-CACACTGGAACTGAGACACGGTCCAGACTCC-TACGGGAG GCAGCAGTGGGGAATAT-TGCACAATGGGCG. A DNA control mix may include a combination of the one or more said group of sequences and the said internal control sequence. A DNA control mix may include any combination of sequences from the first control mix, the second control mix, the third control mix and the internal control sequence. [SEQ. ID NOS 269-272]

In one example, the kit includes two primer-probe multiplex mix vials including internal controls and two DNA control mix vials. The two primer-probe multiplex mixes may provide for identification of up to six antibiotic resistance genes and internal controls. A first primer-probe mix may include sequences for detecting gene families which are MOX-like, ACC-like, FOX-like and internal controls. A second primer-probe mix may include sequences for detecting gene families which are DHA-like, ACT/MIR-like, CMY-2-like and internal controls. A first DNA control mix may include DNA sequences for MOX, ACC, FOX and an internal control DNA sequence. A second DNA control mix may include DNA sequences for DHA, ACT/MIR, CMY-2 and an internal control DNA sequence.

It is contemplated that the combination of gene families may vary. For example, a primer-probe mix may include sequences for detecting any combination of the following genes: MOX-like, ACC-like, FOX-like, DHA-like, ACT/MIR-like and CMY-2-like. It is further contemplated that additional β-lactamase gene targets may be included in the primer-probe mix or mixes.

The first primer-probe mix may include one or more primers and/or probes selected from the group consisting of: GCTGCTCAAGGAGCACAGGAT, CACATTGACAT-AGGTGTGGTGC, 56-FAM/AGGATGGCA/ZEN/AGGCCCACTATTTCA/3IABkFQ,
AACAGCCTCAGCAGCCGGTTA, TTCGCCGCAAT-CATCCCTAGC, 5HEX/AGCCATTAC/ZEN/GTTCCAGAGTTGCGT/3IABkFQ, GCCGAGGCT-TACGGGATCAAG, CAAAGCGCGTAACCGGATTGG and 5TEX615/TCTGCTGAAGTTTRYCGAGGCMAA/3IAbRQSp. The first primer-probe mix may include one or more internal controls selected from the group consisting of: GAGAGGATGAYCAGCCACAC, CGCCCATTGTS-CAATATTCC and 5TYE665/TGAGACACGGTCCA-GACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 192-203]

The second primer-probe mix may include one or more primers and/or probes selected from the group consisting of: AACTTTCACAGGTGTGCTGGGT, CCGTACGCAT-ACTGGCTTTGC, 56-FAM/AAACCGGGC/ZEN/GA-TATGCGTCTGTAT/3IABkFQ, CTGGGTTC-TATAAGTAAAACCTTCACCGG,
CTTCCACTGCGGCTGCCAGTT, 5HEX/GATGCCATT/ZEN/GCYCGSGGTGAAAT/3IABkFQ, CCGAAGCC-TATGGCGTGAAATCC, GCAATGCCCTGCTGGAGCG, and 5TEX615/ATGTTGGCCTGAACCCAGCG/3IAbRQSp. The second primer-probe mix may include one or more internal controls selected from the group consisting of: GAGAGGATGAYCAGCCACAC, CGCCCATTGTS-CAATATTCC and 5TYE665/TGAGACACGGTCCA-GACTCCTACG/3IAbRQSp. A primer-probe mix may include a combination of the one or more said group of primers and/or probes and the one or more said group of internal controls. The primer-probe mix including internal controls may be a multiplex mix. [SEQ. ID NOS 204-215]

The kit may include exactly two primer and/or probe mixes, a first primer and/or probe mix including one or more primers and/or probes selected from the group consisting of: GCTGCTCAAGGAGCACAGGAT, CACATTGACAT-AGGTGTGGTGC, 56-FAM/AGGATGGCA/ZEN/AGGCCCACTATTTCA/3IABkFQ,
AACAGCCTCAGCAGCCGGTTA, TTCGCCGCAAT-CATCCCTAGC, 5HEX/AGCCATTAC/ZEN/GTTCCAGAGTTGCGT/3IABkFQ, GCCGAGGCT-TACGGGATCAAG, CAAAGCGCGTAACCGGATTGG, 5TEX615/TCTGCTGAAGTTTRYCGAGGCMAA/3IAbRQSp, GAGAGGATGAYCAGCCACAC, CGCC-CATTGTSCAATATTCC, and 5TYE665/TGA-GACACGGTCCAGACTCCTACG/3IAbRQSp; and a second primer and/or probe mix including one or more primers and/or probes selected from the group consisting of: AACTTTCACAGGTGTGCTGGGT, CCGTACGCAT-ACTGGCTTTGC, 56-FAM/AAACCGGGC/ZEN/GA-TATGCGTCTGTAT/3IABkFQ, CTGGGTTC-TATAAGTAAAACCTTCACCGG,
CTTCCACTGCGGCTGCCAGTT, 5HEX/GATGCCATT/ZEN/GCYCGSGGTGAAAT/3IABkFQ, CCGAAGCC-TATGGCGTGAAATCC, GCAATGCCCTGCTGGAGCG, 5TEX615/ATGTTGGCCTGAACCCAGCG/3IAbRQSp, GAGAGGATGAYCAGCCACAC, CGCCCATTGTS-CAATATTCC, and 5TYE665/TGAGACACGGTCCA-GACTCCTACG/3IAbRQSp. Primers and/or probes included in this group may or may not be degenerate at any nucleotide position. [SEQ. ID NOS 192-215]

A first DNA control mix may include one or more sequences selected from the group consisting of: GCTGCT-CAAGGAGCACAGGATCCCGGG-CATGGCGGTGGCCGTGCTCAAGGATGG CAAGGCC-CACTATTTCAATTACGGGGTGGCCAACCGGGAGA-GCGGGGCCAGCGT CAGCGAGCA-GACCCTGTTCGAGATAGGATCCGTGAGCAA-GACCCTGACTGCGACC CTGGGGGCC-TATGCGGTGGTCAAGGGAGCGATGCAGCTGGATG-ACAAGGCGAGC CGGCACGCGCCCTGGCTCAAGG-GATCCGTCTTTGACAGCATCACCATGGGGGAG
CTTGCCACCTACAGCGCCGGAGGCCTGC-CACTGCAATTCCCCGAGGAGGTGGATT
CATCCGAGAAGATGCGCGCCTAC-TACCGCCAGTGGGCCCCTGTCTATTCGCCGGG
CTCCCATCGCCAGTACTCCAACCCCAGCAT-AGGGCTGTTCGGCCACCTGGCGGCGAGCAGCCT-GAAGCAGCCATTTGCCCAGTTGATGGAGCA-GACCCTGCTGCCCGGG
CTCGGCATGCACCACACCTATGTCAATGTG, AACAGCCTCAGCAGCCGGTTACGGAAAATACGTT-ATTTGAAGTGGGTTCGCTGAGT
AAAACGTTTGCTGCCACCTTGGCGTCC- TATGCGCAGGTGAGCGGTAAGCTGTCTTT GGATCAAAGCGTTAGCCATTACGTTCCAGAGTTGCGTGGCAGCAGCTTTGACCAC GTTAGCGTACTCAATGTGGGCACGCATACCTCAGGCCTACAGCTATTTATGCCGGA AGATATTAAAAATACCACACAGCTGATGGCTTATCTAAAAGCATGGAAACCTGCCGATGCGGCTGGAACCCATCGCGTTTATTCCAATATCGGTACTGGTTTGCTAGGGATG ATTGCGGCGAA and GCCGAGGCTTACGGGATCAAGACCGGCTCGGCGGATCTGCTGAAGTTTACCGAGGCCAACATGGGGTATCAGGGAGATGCCGCGCTAAAAACGCGGATCGCGCTGACCCATACCGGTTTCTACTCGGTGGGAGACATGACTCAGGGGCTGGGTTGGGAGAGCT ACGCCTATCCGTTGACCGAGCAGGCGCTGCTGGCGGGCAACTCCCCGGCGGTGA GCTTCCAGGCCAATCCGGTTACGCGCTTTG. The first DNA control mix may include the following internal control sequence: GAGAGGATGACCAGCCACACTGGAACTGAGACACGGTCCAGACTCCTACGGGAGGCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 273-276]

A second DNA control mix may include one or more sequences selected from the group consisting of: AACTTTCACAGGTGTGCTGGGTGCGGTTTCTGTGGCGAAAAAAGAGATGGCGCTG AATGATCCGGCGGCAAAATACCAGCCGGAGCTGGCTCTGCCGCAGTGGAAGGGG ATCACATTGCTGGATCTGGCTACCTATACCGCAGGCGGACTGCCGTTACAGGTGC CGGATGCGGTAAAAAGCCGTGCGGATCTGCTGAATTTCTATCAGCAGTGGCAGCC GTCCCGGAAACCGGGCGATATGCGTCTGTATGCAAACAGCAGTATCGGCCTGTTGGTGCTCTGACCGCAAACGCGGCGGGGATGCCGTATGAGCAGTTGCTGACTGCACGGATCCTGGCACCGCTGGGGTTATCTCACACCTTTATTACTGTGCCGGAAAGTGCGCAAAGCCAGTATGCGTACGG, TCGGTAAAGCCGATGTTGCGGCGAACAAACCCGTCACCCCGCAAACCCTGTTTGA GCTGGGCTCTATAAGTAAAACCTTCACCGGCGTACTGGGCGGCGATGCCATTGCCCGGGGTGAAATAGCGCTGGGCGATCCGGTAGCAAAATACTGGCCTGAGCTCACG GGCAAGCAGTGGCAGGGCATTCGCATGCTGGATCTGGCAACCTATACCGCAGGCGGTCTGCCGTTACAGGTGCCGGATGAGGTCACGGATACCGCCTCTCTGCTGCGCTTTTATCAAAACTGGCAGCCGCAGTGGAAG and CCGAAGCCTATGGCGTGAAATCCAGCGTTATTGATATGGCCCGCTGGGTTCAGGC CAACATGGATGCCAGCCACGTTCAGGAGAAAACGCTCCAGCAGGGCATTGC. The second DNA control mix may include the following internal control sequence: GAGAGGATGACCAGCCACACTGGAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 277-280]

In one example, the kit includes two primer-probe multiplex mix vials including internal controls and two DNA control mix vials. The two primer-probe multiplex mixes may provide for identification of up to six antibiotic resistance genes and internal controls. A first primer-probe mix may include sequences for detecting gene families which are OXA-143-like, OXA-23-like, OXA-51-like and internal controls. A second primer-probe mix may include sequences for detecting gene families which are OXA-48-like, OXA-58-like, OXA-24/40-like and internal controls. A first DNA control mix may include DNA sequences for OXA-143, OXA-23, OXA-51 and an internal control DNA sequence. A second DNA control mix may include DNA sequences for OXA-48, OXA-58 and OXA 24/40 and an internal control DNA sequence.

It is contemplated that the combination of gene families may vary. For example, a primer-probe mix may include sequences for detecting any combination of the following genes: OXA-143-like, OXA-23-like, OXA-51-like, OXA-48-like, OXA-58-like and OXA-24/40-like. It is further contemplated that additional β-lactamase gene targets may be included in the primer-probe mix or mixes.

The first primer-probe mix may include one or more primers and/or probes selected from the group consisting of: AGCACATACAGAATATGTCCCTGC, ACCTGTTAACCAACCTACTTGAGGG, /56-FAM/TTGCAAGACGGACTGGCTTAGACC/3BHQ_1/, CCTGATCGGATTGGAGAACC, CTACCTCTTGAATAGGCGTAACC, /5TEX615/ACGTCGCGCAAGTTCCTGATAGAC/3IAbRQSp/, TAGTGACTGCTAATCCAAATCACAG, GCACGAGCAAGATCATTACCATAGC, /5HEX/AGTTATCCAACAAGGCCAAACTCAACA/3BHQ_1/. [SEQ. ID NOS 119-127] The first primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix.

The second primer-probe mix may include one or more primers and/or probes selected from the group consisting of: AATCACAGGGCGTAGTTGTG, ACCCACCAGCCAATCTTAGG, /5HEX/TAGCTTGATCGCCCTCGATTTGGG/3BHQ_1/, GTGGGATGGAAAGCCACG, CACTTGCGGGTCTACAGC, /56-FAM/TTACTTTGGGCGAAGCCATGCAAG/3BHQ_1/, CACCTATGGTAATGCTCTTGC, CTGGAACTGCTGACAATGCC, /5TEX615/TGGGAGAAAGATATGACTTTAGGTGAGGCA/3IAbRQSp/. [SEQ. ID NOS 128-136] The second primer-probe mix may include one or more internal controls selected from the group consisting of: GAGAGGATGAYCAGCCACAC, CGCCCATTGTSCAATATTCC and 5TYE665/TGAGACACGGTCCAGACTCCTACG/3IAbRQSp. A primer-probe mix may include a combination of the one or more said group of primers and/or probes and the one or more said group of internal controls. The primer-probe mix including internal controls may be a multiplex mix.

The kit may include exactly two primer and/or probe mixes, a first primer and/or probe mix including one or more primers and/or probes selected from the group consisting of: AGCACATACAGAATATGTCCCTGC, ACCTGTTAAC-CAACCTACTTGAGGG, /56-FAM/TTGCAA-GACGGACTGGCTTAGACC/3BHQ_1/, CCTGATCG-GATTGGAGAACC, CTACCTCTTGAATAGGCGTAACC, /5TEX615/ACGTCGCGCAAGTTCCTGATAGAC/3IAbRQSp/, TAGTGACTGCTAATCCAAATCACAG, GCACGAGCAAGATCATTACCATAGC, /5HEX/AGT-TATCCAACAAGGCCAAACTCAACA/3BHQ_1/, GAGAGGATGAYCAGCCACAC, CGCCCATTGTS-CAATATTCC and 5TYE665/TGAGACACGGTCCA-GACTCCTACG/3IAbRQSp; and a second primer and/or probe mix including one or more primers and/or probes selected from the group consisting of: AAT-CACAGGGCGTAGTTGTG, ACCCACCAGCCAATCT-TAGG, /5HEX/TAGCTTGATCGCCCTCGATTTGGG/3BHQ_1/, GTGGGATGGAAAGCCACG, CACTTGCGGGTCTACAGC, /56-FAM/TTACTTTGGGCGAAGCCATGCAAG/3BHQ_1/, CACC-TATGGTAATGCTCTTGC, CTG-GAACTGCTGACAATGCC, /5TEX615/TGGGAGAAAGATATGACTTTAGGTGAGGCA/3IAbRQSp/, GAGAGGATGAYCAGCCAC-AC, CGCCCATTGTSCAATATTCC and 5TYE665/TGA-GACACGGTCCAGACTCCTACG/3IAbRQSp. Primers and/or probes included in this group may or may not be degenerate at any nucleotide position. [SEQ. ID NOS 216-239]

A first DNA control mix may include one or more sequences selected from the group consisting of: AGCA-CATACAGAATATGTCCCTGCATCAACATTTAA-GATGCTAAATGCCTTAATTGG ACTAGAAAATCAT-AAAGCTACAACAACTGAGATTTTCAAATGGGACG-GTAAAAAGAGATCTTATCCCATGTGGGAAAAAGA-TATGACTTTAGGTGATGCCATGGCACTTTCA GCAGTTCCTGTATATCAAGAACTTGCAA-GACGGACTGGCTTAGACCTAATGCAAAA AGAAGT-TAAACGGGTTGGTTTTGGTAATATGAACATTG-GAACACAAGTTGATAACTT CTGGTTGGTTGGCCCCCTCAAGATTACACCAATA-CAAGAGGTTAATTTTGCCGATG ATTTTGCAAATAATCGATTACCCTTTAAATTAGA-GACTCAAGAAGAAGTTAAAAAAATGCTTCTGAT-TAAAGAATTCAATGGTAGTAAAATT-TATGCAAAAAGCGGCTGGGGAA TGGATGTAACCCCTCAAGTAGGTTGGTTAACAGGT, CCTGATCGGATTGGAGAACCAGAAAACGGATAT-TAATGAAATATTTAAATGGAAGG GCGAGAAAAGGTCATTTACCGCTTGGGAAAAAGA-CATGACACTAGGAGAAGCCAT GAAGCTTTCTGCAGTCCCAGTCTATCAG-GAACTTGCGCGACGTATCGGTCTTGATC TCATGCAAAAAGAAGTAAAACGTAT-TGGTTTCGGTAATGCTGAAATTGGACAGCAG GTT-GATAATTTCTGGTTGGTAGGACCATTAAAGGT-TACGCCTATTCAAGAGGTAG and TAGTGACTGCTAATCCAAATCACAGCGCTT-CAAAATCTGATGAAAAGCAGAGAAA ATTAAAAATTTATTTAACGAAGTACACAC-TACGGGTGTTTTAGTTATCCAACAAGGC CAAACT-CAACAAAGCTATGGTAATGATCTTGCTCGTGC. The first DNA control mix may include the following internal control sequence: GAGAGGATGACCAGCCACACTG-GAACTGAGACACGGTCCAGACTCCTACGGGAG GCAGCAGTGGGGAATATTGCACAATGGGCG. A DNA control mix may include a combination of the one or more said group of sequences and the said internal control sequence. A DNA control mix may include any combination of sequences from the first control mix, the second control mix and the internal control sequence. [SEQ. ID NOS 281-284]

A second DNA control mix may include one or more sequences selected from the group consisting of: AAT-CACAGGGCGTAGTTGTGCTCTGGAAT-GAGAATAAGCAGCAAGGATTTACCAAT AATCT-TAAACGGGCGAACCAAGCATTTTTACCCGCATCT-ACCTTTAAAATTCCCAAT AGCTTGATCGCCCTCGAT-TTGGGCGTGGTTAAGGATGAACACCAAGTCTT-TAAGTG GGATGGACAGACGCGCGATATCGC-CACTTGGAATCGCGATCATAATCTAATCACC GCGATGAAATATTCAGTTGTGCCTGTTTATCA AGAATTTGCCCGCCAAATTGGCGAGGCACGTAT-GAGCAAGATGCTACATGCTTTCGATTATGGTAAT-GAGGACATTTCGGGCAATGTAGACA GTTTCTGGCTCGACGGTGGTATTCGAATTTCGGC-CACGGAGCAAATCAGCTTTTTAAGAAAGCTGTAT-CACAATAAGTTACACGTATCGGAGCGCAGCC AGCGTATTGTCAAACAAGCCATGCTGACCGAAGC-CAATGGTGACTATATTATTCGGGCTAAAACTGGA-TACTCGACTAGAATCGAACCTAAGAT-TGGCTGGTGGGT, GTGGGATGGAAAGCCACGTTTTTT-TAAAGCATGGGACAAAGATTTTACTTTGGGCG AAGCCATGCAAGCATCTACAGTGCCTGTATAT-CAAGAATTGGCACGTCGTATTGGTCCAAGCT-TAATGCAAAGTGAATTGCAACGTATTGGT-TATGGCAATATGCAAATAGG CACGGAAGTTGATCAATTTTGGTT-GAAAGGGCCTTTGACAATTACACCTATACAAG AAGTAAAGTTTGTGTATGATTTAGCC-CAAGGGCAATTGCCTTTTAAACCTGAAGTTC AGCAACAAGT-GAAAGAGATGTTGTATGTAGAGCGCAGAGGG-GAGAATCGTCTATATGCTAAAAGTGGCTGGG-GAATGGCTGTAGACCCGCAAGTG, CACTTGCGGGTCTACAGCCATTCCCCAGCCACTTT-TAGCATATAGACGATTCTCCCCTCTGCGCTCTA-CATACAACATCTCTTTCACTTGTTGCT-GAACTTCAGGTTTAAAAG GCAATTGCCCTTGGGCTAAATCATACACAAACTT-TACTTCTTGTATAGGTGTAATTG TCAAAGGCCCTTT-CAACCAAAATTGATCAACTTCCGTGCCTATTTGCAT-ATTGCCAT AACCAATACGTTGCAATTCACTTTGCAT-TAAGCTTGGACCAATACGACGTGCCAATT CTTGA-TATACAGGCACTGTAGATGCTTGCATGGCTTCGCC-CAAAGTAAAATCTTTGT CCCATGCTTTAAAAAAACGTGGCTTTCCATCCCAC, and CACCTATGGTAATGCTCTTGCA CGAGCAAATAAAGAATATGTCCCTGCATCAACATT TAAGATGCTAAATGCTTTAATCGGGCTAGAAAAT-CATAAAGCAACAACAAATGAGAT TTTCAAATGG-GATGGTAAAAAAGAACTTATCCTATGTGG-GAGAAAGATATGACTTT AGGTGAGGCAATGGCATTGTCAGCAGTTCCAG. The second DNA control mix may include the following internal control sequence: GAGAGGATGACCAGCCACACTG-GAACTGAGACACGGTCCAGACTCCTACGGGAG GCAGCAGTGGGGAATATTGCACAATGGGCG. A DNA control mix may include a combination of the one or more said group of sequences and the said internal control sequence additional β-lactamase. A DNA control mix may include any combination of sequences from the first control mix, the second control mix and the internal control sequence. [SEQ. ID NOS 285-289]

In one example, the kit includes one primer-probe multiplex mix vials including internal control and one DNA control mix vial. A primer-probe mix may include sequences for detecting MCR gene families and internal control.

The primer-probe mix may include primers and/or probes selected from the group consisting of: CCGTGTATGTTCAGCTAT, CTTATCCATCACGCCTTT, /5TEX615/TATGATGTCGATACCGCCAAATACCA/3IAbRQSp/, CTGTATGTCAGCGATCAT, GATGCCAGTTTGCTTATCC, /56-FAM/AAGTCTGGG/ZEN/TGAGAACGGTGTCTAT/3IABkFQ/, CAGTCAGTATGCGAGTTTC, AAAATTCGCCAAGCCATC, and /5HEX/TGCATAAGC/ZEN/CAGTGCGTTTT-TATAT/3IABkFQ/. The primer-probe mix may include one or more internal controls selected from the group consisting of: GAGAGGATGAYCAGCCACAC, CGCCCATTGTS-CAATATTCC and 5TYE665/TGAGACACGGTCCA-GACTCCTACG/3IAbRQSp. The primer-probe mix may include a combination of the one or more said group of primers and/or probes and the one or more said group of internal controls. The primer-probe mix including internal controls may be a multiplex mix. [SEQ. ID NOS 137-145]

A DNA control mix may include one or more sequences selected from the group consisting of

```
ATGATGCAGCATACTTCTGTGTGGTACCGACGCTCGGTCAGTCCGTTTGT
TCTTGTGGGAGTGTTGCCGTTTTCTTGACCGCGACCGCCAATCTTACCTT
TTTTGATAAAATCAGCCAAACCTATCCCATCGCGGACAATCTCGGCTTTG
TGCTGACGATCGCTGTCGTGCTCTTTGGCGCGATGCTACTGATCACCACG
CTGTTATCATCGTATCGCTATGTGCTAAAGCCTGTGTTGATTTTGCTATT
AATCATGGGCGCGGTGACCAGTTATTTTACTGACACTTATGGCACGGTCT
ATGATACGACCATGCTCCAAAATGCCCTACAGACCGACCAAGCCGAGACC
AAGGATCTATTAAACGCAGCGTTTATCATGCGTATCATTGGTTTGGGTGT
GCTACCAAGTTTGCTTGTGGCTTTTGTTAAGGTGGATTATCCGACTTGGG
GCAAGGGTTTGATGCGCCGATTGGGCTTGATCGTGGCAAGTCTTGCGCTG
ATTTTACTGCCTGTGGTGGCGTTCAGCAGTCATTATGCCAGTTTCTTTCG
CGTGCATAAGCCGCTGCGTAGCTATGTCAATCCGATCATGCCAATCTACT
CGGTGGGTAAGCTTGCCAGTATTGAGTATAAAAAGCCAGTGCGCCAAAA
GATACCATTTATCACGCCAAAGACGCGGTACAAGCAACCAAGCCTGATAT
GCGTAAGCCACGCCTAGTGGTGTTCGTCGTCGGTGAGACGGCACGCGCCG
ATCATGTCAGCTTCAATGGCTATGAGCGCGATACTTTCCCACAGCTTGCC
AAGATCGATGGCGTGACCAATTTTAGCAATGTCACATCGTGCGGCACATC
GACGGCGTATTCTGTGCCGTGTATGTTCAGCTATCTGGGCGCGGATGAGT
ATGATGTCGATACCGCCAAATACCAAGAAAATGTGCTGGATACGCTGGAT
CGCTTGGGCGTAAGTATCTTGTGGCGTGATAATAATTCGGACTCAAAAGG
CGTGATGGATAAGCTGCCAAAAGCGCAATTTGCCGATTATAAATCCGCGA
CCAACAACGCCATCTGCAACACCAATCCTTATAACGAATGCCGCGATGTC
GGTATGCTCGTTGGCTTAGATGACTTTGTCGCTGCCAATAACGGCAAAGA
TATGCTGATCATGCTGCACCAAATGGGCAATCACGGGCCTGCGTATTTTA
```

-continued

```
AGCGATATGATGAAAAGTTTGCCAAATTCACGCCAGTGTGTGAAGGTAAT
GAGCTTGCCAAGTGCGAACATCAGTCCTTGATCAATGCTTATGACAATGC
CTTGCTTGCCACCGATGATTTCATCGCTCAAAGTATCCAGTGGCTGCAGA
CGCACAGCAATGCCTATGATGTCTCAATGCTGTATGTCAGCGATCATGGC
GAAAGTCTGGGTGAGAACGGTGTCTATCTACATGGTATGCCAAATGCCTT
TGCACCAAAAGAACAGCGCAGTGTGCCTGCATTTTTCTGGACGGATAAGC
AAACTGGCATCACGCCAATGGCAACCGATACCGTCCTGACCCATGACGCG
ATCACGCCGACATTATTAAAGCTGTTTGATGTCACCGCGGACAAAGTCAA
AGACCGCACCGCATTCATCCGCTGA
```
and
```
ATGACATCACATCACTCTTGGTATCGCTATTCTATCAATCCTTTTGTGCT
GATGGGTTTGGTGGCGTTATTTTTGGCAGCGACAGCGAACCTGACATTTT
TTGAAAAAGCGATGGCGGTCTATCCTGTATCGGATAACTTAGGCTTTATC
ATCTCAATGGCGGTGGCGGTGATGGGTGCTATGCTACTGATTGTCGTGCT
GTTATCCTATCGCTATGTGCTAAAGCCTGTCCTGATTTTGCTACTGATTA
TGGGTGCGGTGACGAGCTATTTTACCGATACTTATGGCACGGTCTATGAC
ACCACCATGCTCCAAAATGCCATGCAAACCGACCAAGCCGAGTCTAAGGA
CTTGATGAATTTGGCGTTTTTTGTGCGAATTATCGGGCTTGGCGTGTTGC
CAAGTGTGTTGGTCGCAGTTGCCAAAGTCAATTATCCAACATGGGGCAAA
GGTCTGATTCAGCGTGCGATGACATGGGGTGTCAGCCTTGTGCTGTTGCT
TGTGCCGATTGGACTATTTAGCAGTCAGTATGCGAGTTTCTTTCGGGTGC
ATAAGCCAGTGCGTTTTTATATCAACCCGATTACGCCGATTTATTCGGTG
GGTAAGCTTGCCAGTATCGAGTACAAAAAAGCCACTGCGCCAACAGACAC
CATCTATCATGCCAAAGACGCCGTGCAGACCACCAAGCCGAGCGAGCGTA
AGCCACGCCTAGTGGTGTTCGTCGTCGGTGAGACGGCGCGTGCTGACCAT
GTGCAGTTCAATGGCTATGGCCGTGAGACTTTCCCGCAGCTTGCCAAAGT
TGATGGCTTGGCGAATTTTAGCCAAGTGACATCGTGTGGCACATCGACGG
CGTATTCTGTGCCGTGTATGTTCAGCTATTTGGGTCAAGATGACTATGAT
GTCGATACCGCCAAATACCAAGAAAATGTGCTAGATACGCTTGACCGCTT
GGGTGTGGGTATCTTGTGGCGTGATAATAATTCAGACTCAAAAGGCGTGA
TGGATAAGCTACCTGCCACGCAGTATTTTGATTATAAATCAGCAACCAAC
AATACCATCTGTAACACCAATCCCTATAACGAATGCCGTGATGTCGGTAT
GCTTGTCGGGCTAGATGACTATGTCAGCGCCAATAATGGCAAAGATATGC
TCATCATGCTACACCAAATGGGCAATCATGGGCCGGCGTACTTTAAGCGT
TATGATGAGCAATTTGCCAAATTCACCCCCGTGTGCGAAGGCAACGAGCT
TGCCAAATGCGAACACCAATCACTCATCAATGCCTATGACAATGCGCTAC
TTGCGACTGATGATTTTATCGCCAAAAGCATCGATTGGCTAAAAACGCAT
GAAGCGAACTACGATGTCGCCATGCTCTATGTCAGTGACCACGGCGAGAG
CTTGGGCGAAAATGGTGTCTATCTGCATGGTATGCCAAATGCCTTTGCAC
CAAAAGAACAGCGAGCTGTGCCTGCGTTTTTTGGTCAAATAATACGACA
TTCAAGCCAACTGCCAGCGATACTGTGCTGACGCATGATGCGATTACGCC
```

-continued
AACACTGCTTAAGCTGTTTGATGTCACAGCGGGCAAGGTCAAAGACCGCG
CGGCATTTATCCAGTAA.

The DNA control mix may include the following internal control sequence: GAGAGGATGACCAGCCACACTG-GAACTGAGACACGGTCCAGACTCCTACGGGAG GCAGCAGTGGGGAATATTGCACAATGGGCG. A DNA control mix may include a combination of the one or more said group of sequences and the said internal control sequence. [SEQ. ID NOS 290-292]

In one example, the kit includes one primer-probe multiplex mix vial including internal control and one DNA control mix vial. A primer-probe mix may include sequences for detecting TEM-like and SHV-like gene families and internal control.

The primer-probe mix may include primers and/or probes selected from the group consisting of: AGATCAGTTGGGTGCACG, TGCTTAATCAGT-GAGGCACC, /56-FAM/ATGAAGCCA/ZEN/TAC-CAAACGACGAGC/3IABkFQ/, CTGGAGCGAAA-GATCCACTA, ATCGTCCACCATCCACTG, and /5HEX/CCAGATCGG/ZEN/CGACAACGTCACC/3IABkFQ/.
The primer-probe mix may include one or more internal controls selected from the group consisting of: GAGAG-GATGAYCAGCCACAC, CGCCCATTGTSCAATATTCC and 5TYE665/TGAGACACGGTCCAGACTCCTACG/3IAbRQSp. The primer-probe mix may include a combination of the one or more said group of primers and/or probes and the one or more said group of internal controls. The primer-probe mix including internal controls may be a multiplex mix. [SEQ. ID NOS 240-248]

A DNA control mix may include one or more sequences selected from the group consisting of: AGATCAGTTGGGTGCACGAGTGGGTTA-CATCGAACTGGATCTCAACAGCGGTAAG ATCCTT-GAGAGTTTTCGCCCCGAAGAACGTTTTCCAATGAT-GAGCACTTTTAAAGTT
CTGCTATGTGGTGCGGTATTATCCCGTGTTGACG CCGGGCAAGAGCAACTCGGTC GCCGCATACACT-ATTCTCGAAATGACTTGGTTGAGTACTCACCAGT-CACAGAAAAG CATCTTACGGATGGCATGACA GTAAGAGAATTATGCAGTGCTGCCATAACCATGAG TGATAACACTGCGGCCAACTTACTTCTGACAAC-GATCGGAGGACCGAAGGAGCTA ACCGCTTTTTTGCACAACATGGGGGAT-CATGTAACTCGCCTTGATCGTTGGGAACCGGAGCT-GAATGAAGCCATACCAAACGACGAGCGTGACAC-CACGACGCCTGCAGC
AATGGCAACAACGTTGCGCAAACTAT-TAACTGGCGAACTACTTACTCTAGCTTCCC GGCAACAATTAATAGACTGGATGGAGGCGGA-TAAAGTTGCAGGACCACTTCTGCG CTCGGCCCTTCCGGCTGGCTGGTTTATTGCTGA-TAAATCTGGAGCCAGTGAGCGT GGGTCTCGCGGTATCATTGCAGCACTGGGGCCA-GATGGTAAGCCCTCCCGTATCG TAGTTATCTA-CACGACGGGGAGTCAGGCAACTATGGAT-GAACGAAATAGACAGATC
GCTGAGATAGGTGCCTCACTGATTAAGCA and CTG-GAGCGAAAGATCCACTATCGCCAGCAG-GATCTGGTGGACTACTCGCCGGTCA GCGAAAAACACCTTGCCGACGG-CATGACGGTCGGCGAACTCTGCGCCGCCGCCA TTACCATGAGCGATAACAGCGCCGC-CAATCTGCTGCTGGCCACCGTCGGCGGCC CCGCAGGATTGACTGCCTTTTTGCGCCA-GATCGGCGACAACGTCACCCGCCTTGA CCGCTGG-GAAACGGAACTGAAT-
GAGGCGCTTCCCGGCGACGCCCGCGACACCAC TACCCCGGCCAGCATGGCCGCGACCC TGCGCAAGCTGCTGACCAGCCAGCGTCT GAGCGCCCGTTCGCAACGGCAGCTGCTGCAGTG-GATGGTGGACGAT. The DNA control mix may include the following internal control sequence: GAGAG-GATGACCAGCCACACTGGAACTGA-GACACGGTCCAGACTCCTACGGGAG GCAGCAGTGGGGAATATTGCACAATGGGCG. A DNA control mix may include a combination of the one or more said group of sequences and the said internal control sequence. [SEQ. ID NOS 293-295]

The primer-probe multiplex mix may comprise different oligonucleotide sequences. An oligonucleotide sequence may be utilized as a primer. An oligonucleotide sequence may be utilized as a probe. An oligonucleotide sequence may be utilized as an internal control sequence. The oligonucleotide concentration of a primer and/or probe sequence may range from 0.05 μM to 60 μM. For example, the oligonucleotide concentration of a primer and/or probe sequence may range from 3 μM to 8 μM. For example, the oligonucleotide concentration of an internal control sequence may range from 2 μM to 6 μM. For example, the oligonucleotide concentration of an internal control sequence may range from 2 μM to 8 μM. The vial oligonucleotide concentrations may be prepared as a 10× stock solution.

The synthetic gene size of a DNA control sequence may be from about 84 bp to about 533 bp. The concentration of a DNA control sequence may be about 25 ng/μl. The concentration of a DNA control sequence may be from 0.033 ng/μL to about 0.5 ng/μl.

The present teachings provide methods for detection of β-lactamase gene families from a biological sample. Preferably, the sample includes Gram-negative bacteria. The method may include sample processing. The method may include extracting DNA from the sample. The method may include extracting RNA from the sample. The method may include the use of assays of the present teachings. The assays may be included in a kit or kits. The method may include employing the kit of the present teachings for the detection of multiple β-lactamase gene families from a biological sample.

The method may include employing the kit for analysis of nucleic acid contained in a clinical sample. The method may include employing the kit for analysis of DNA extracted from a clinical sample. The method may include employing the kit for analysis of DNA extracted from an overnight bacterial culture of a clinical sample.

The method may include amplifying a targeted DNA sequence by real-time polymerase reaction. The method may include amplifying several targeted DNA sequences by multiplex real-time polymerase reaction. The method may include analyzing the amplified sequences or amplicons. The method may include detecting the presence or absence of β-lactamase genes. The method may include detecting the presence or absence of ampC β-lactamase genes. The method may include identifying up to six β-lactamase gene families. The method may include identifying up to nine β-lactamase gene families. The method may include identifying up to fifteen β-lactamase gene families. The method may include identifying up to twenty β-lactamase gene families. The method may include identifying from about six to about thirty β-lactamase gene families. The method may include analyzing collected data.

Figure 2:
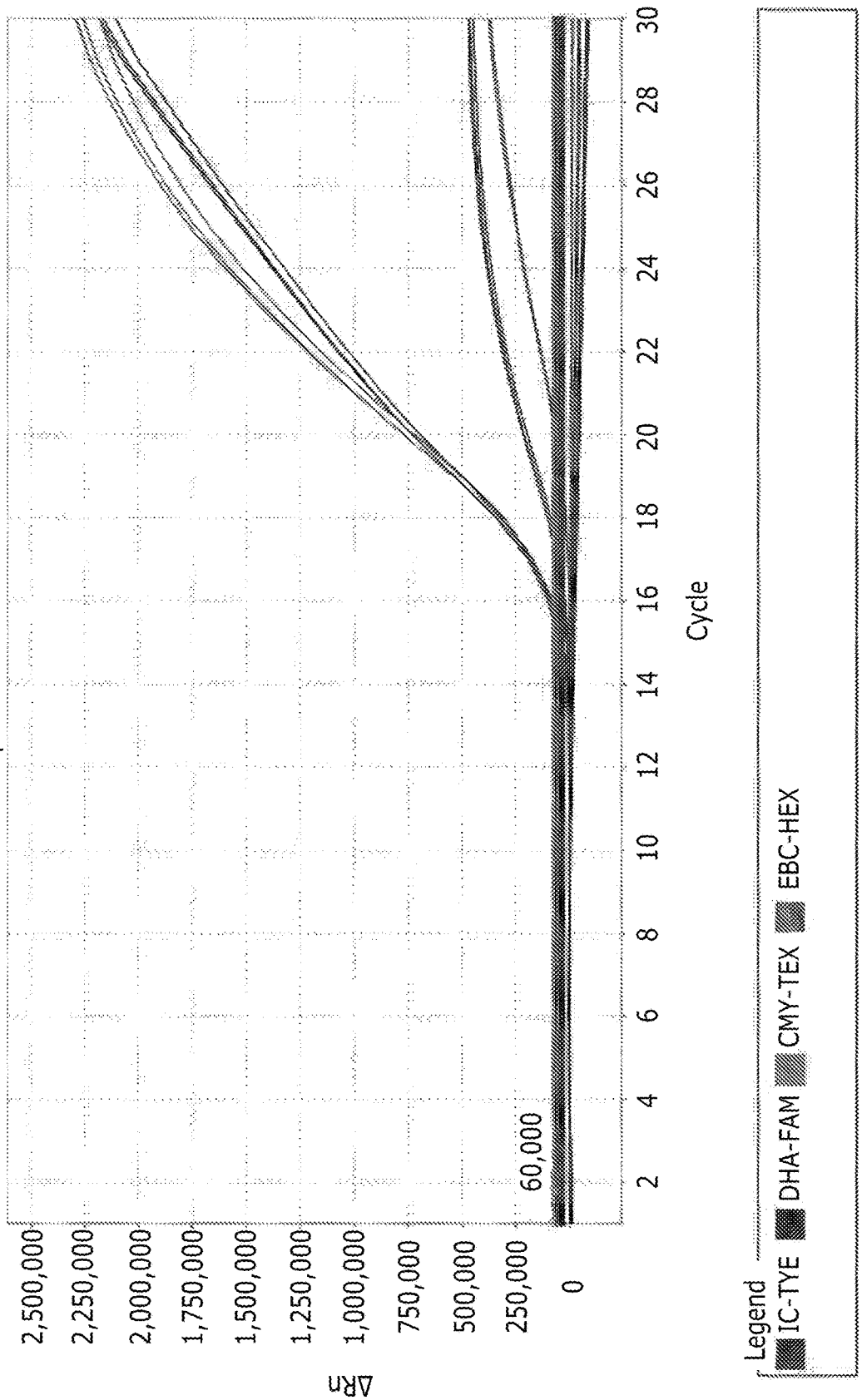
FIG. 2 depicts an amplification plot of an exemplary mix 2 of a kit including ampC gene targets.
Figure 3:
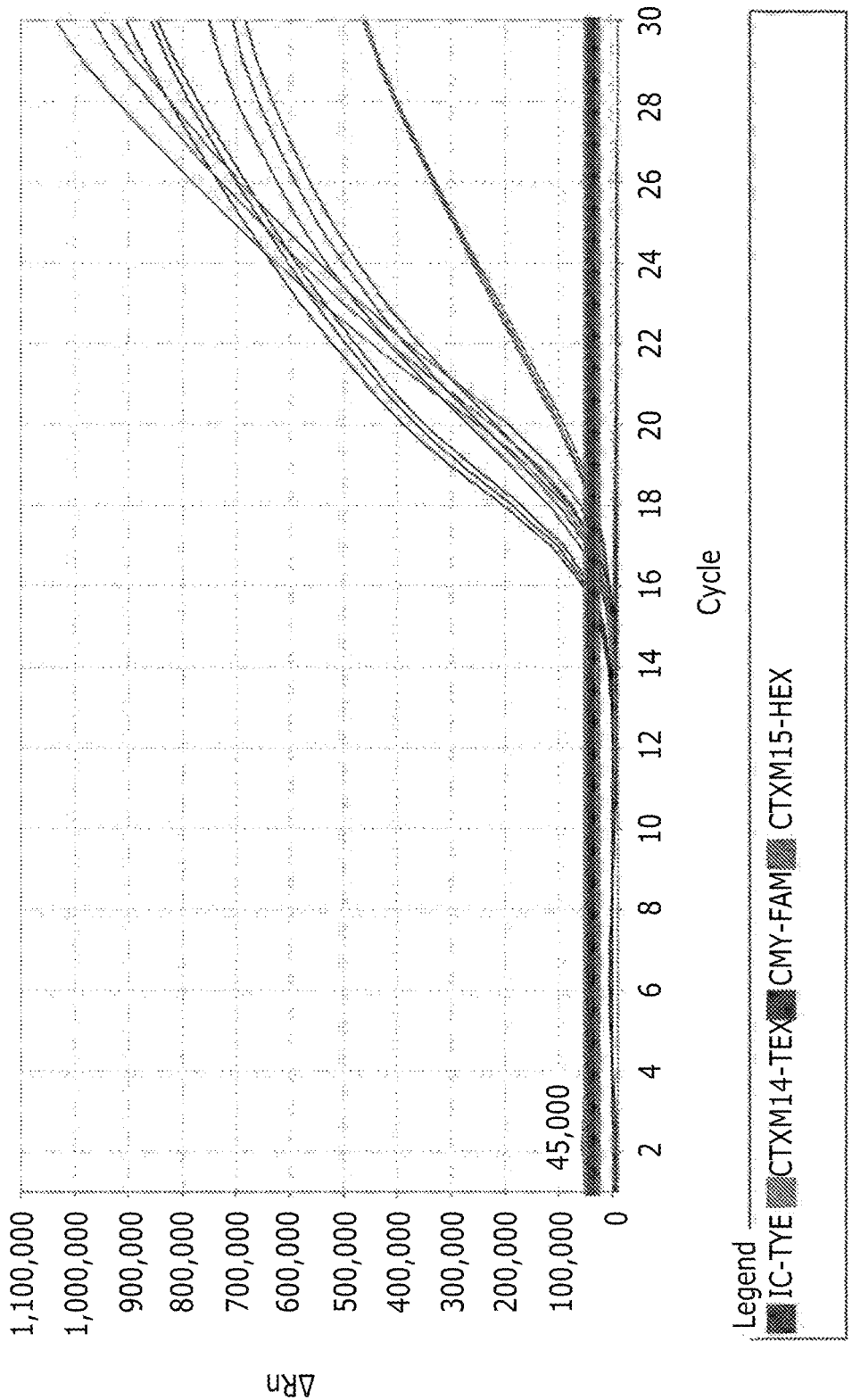
FIG. 3 depicts an amplification plot of an exemplary mix 1 of a kit including β-lactamase gene targets.
Figure 4:
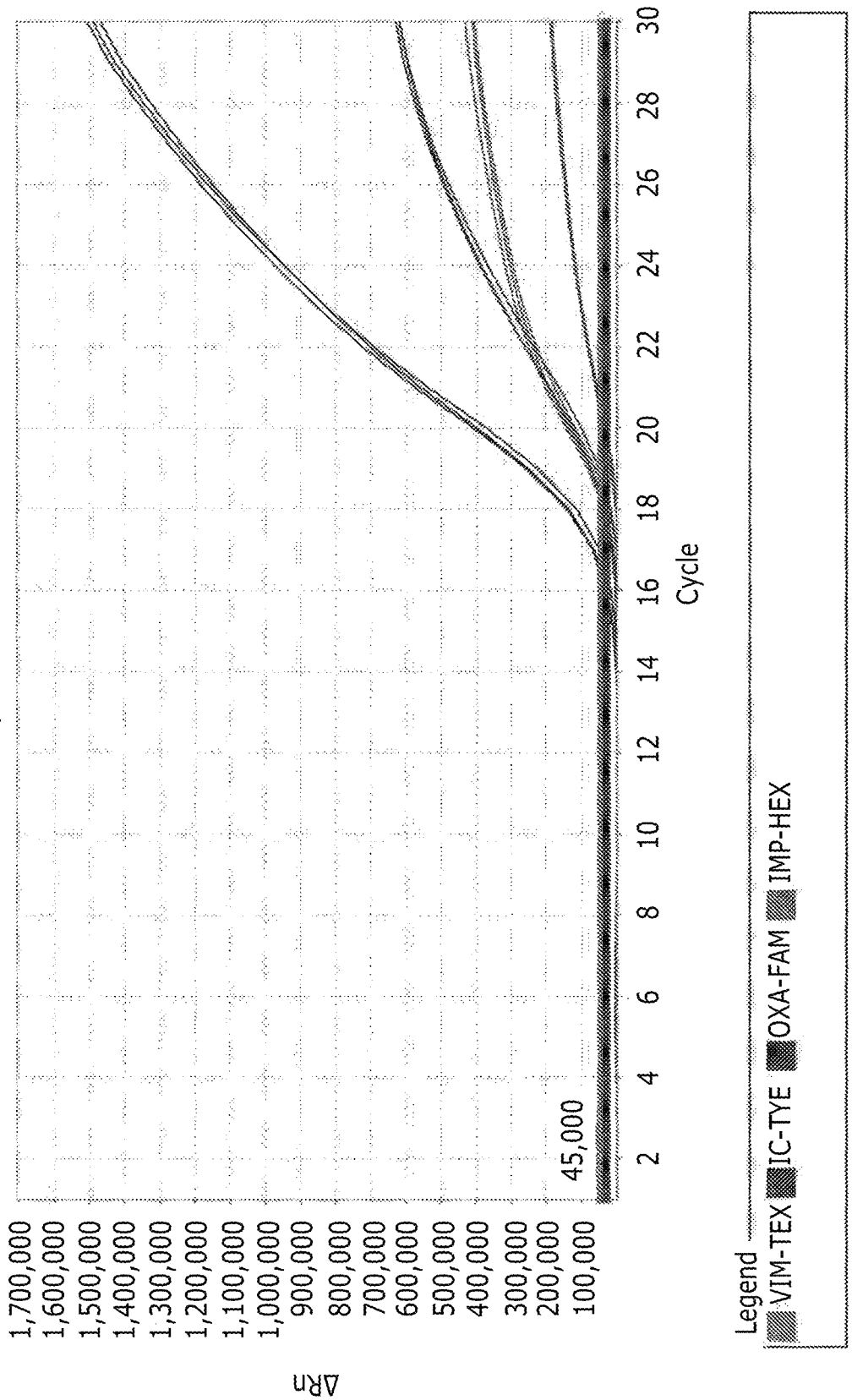
FIG. 4 depicts an amplification plot of an exemplary mix 2 of a kit including β-lactamase gene targets.
Figure 5:
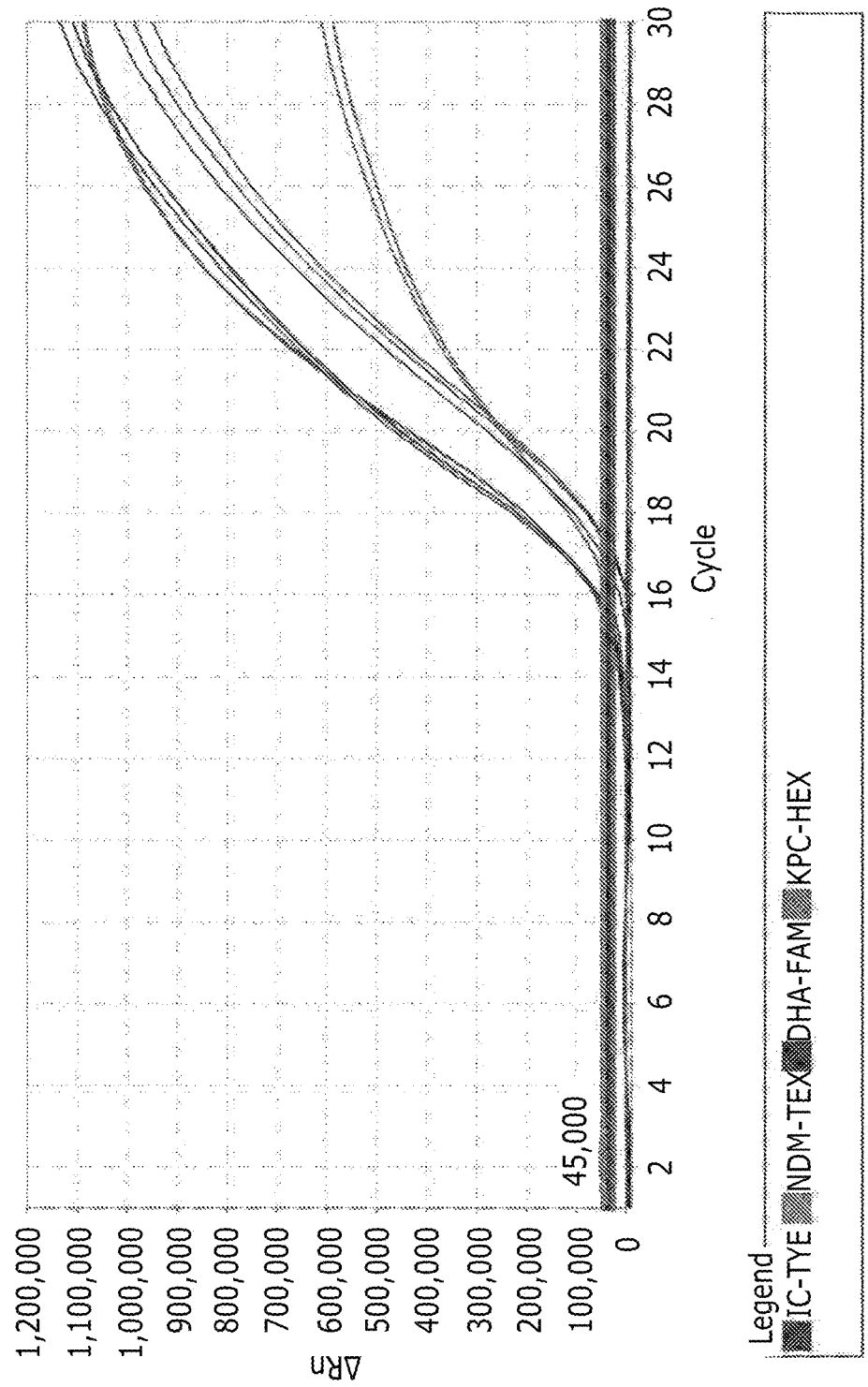
FIG. 5 depicts an amplification plot of an exemplary mix 3 of a kit including β-lactamase gene targets.
Figure 6:
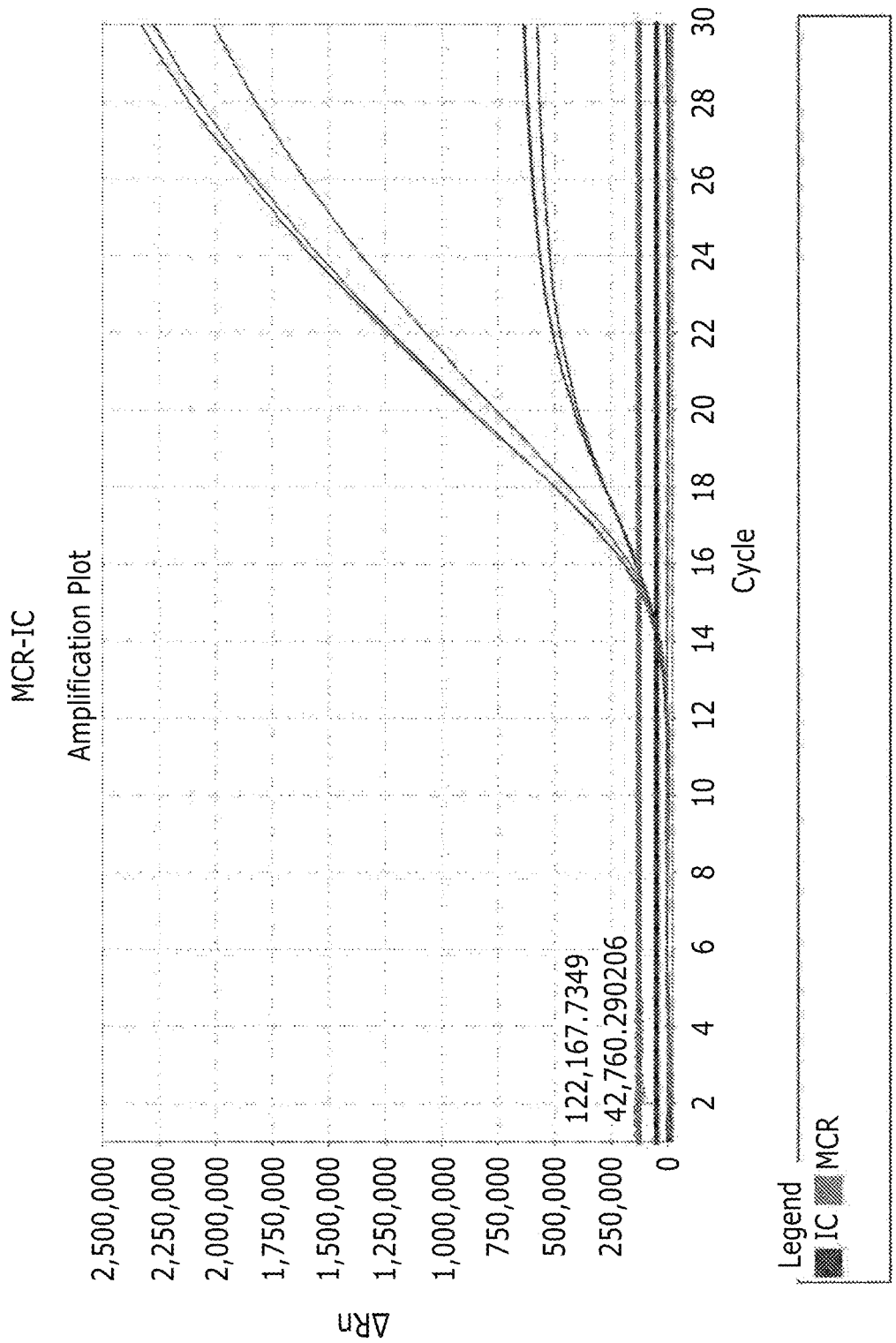
FIG. 6 depicts an amplification plot of an exemplary internal control mix of a kit including MCR gene targets.
Figure 7:
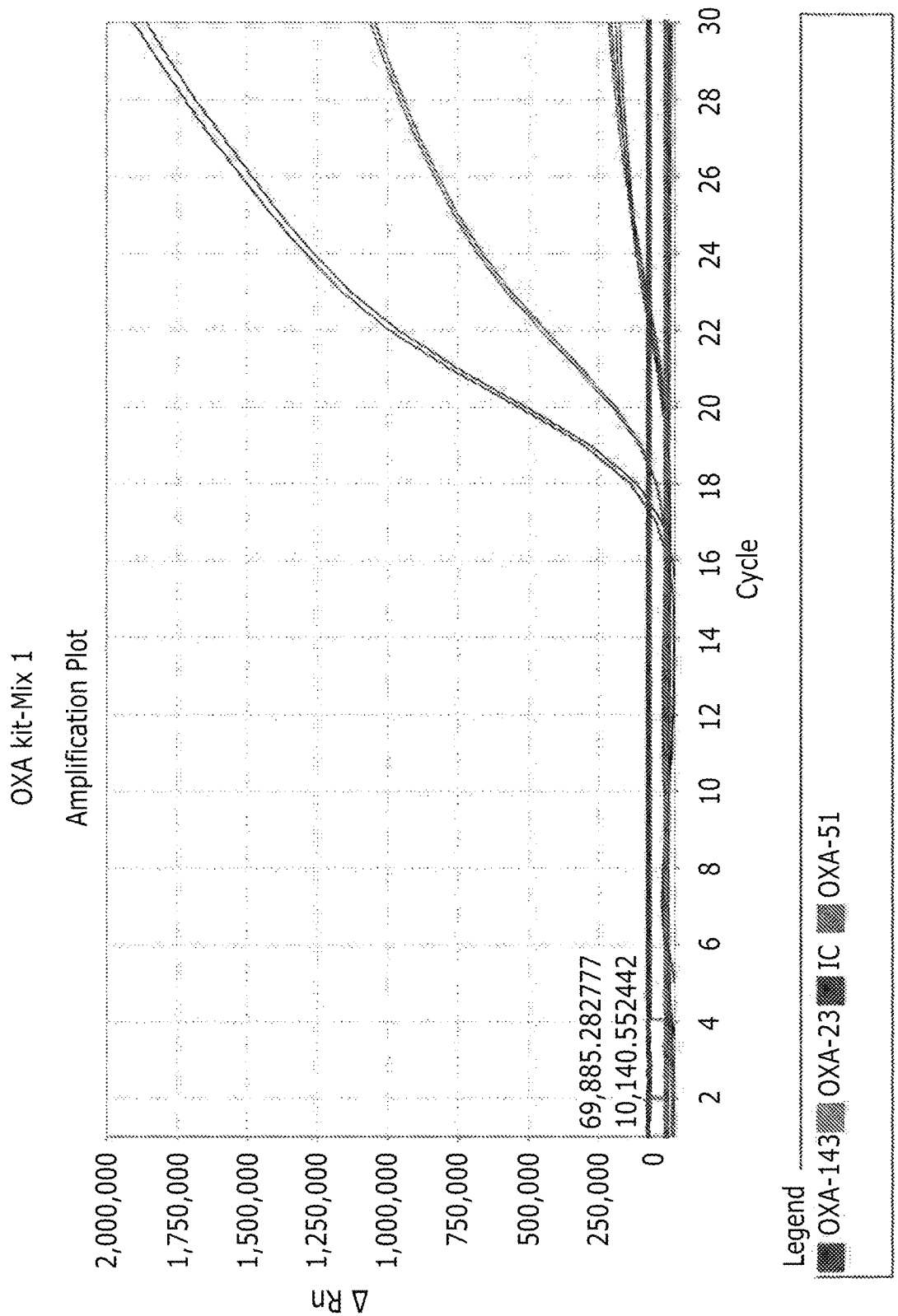
FIG. 7 depicts an amplification plot of an exemplary mix 1 of a kit including OXA gene targets.
Figure 8:
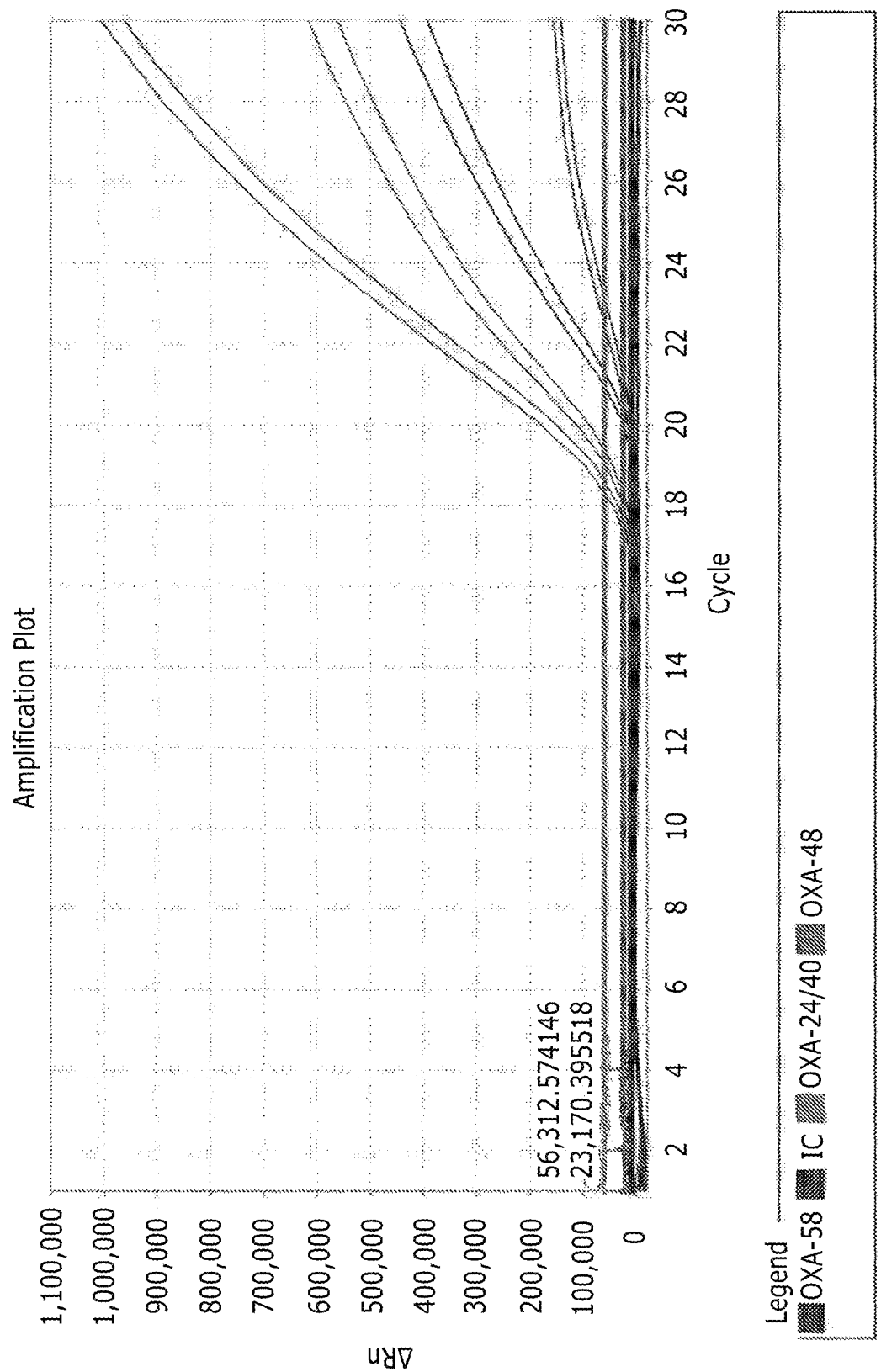
FIG. 8 depicts an amplification plot of an exemplary mix 2 of a kit including OXA gene targets.
Figure 9:
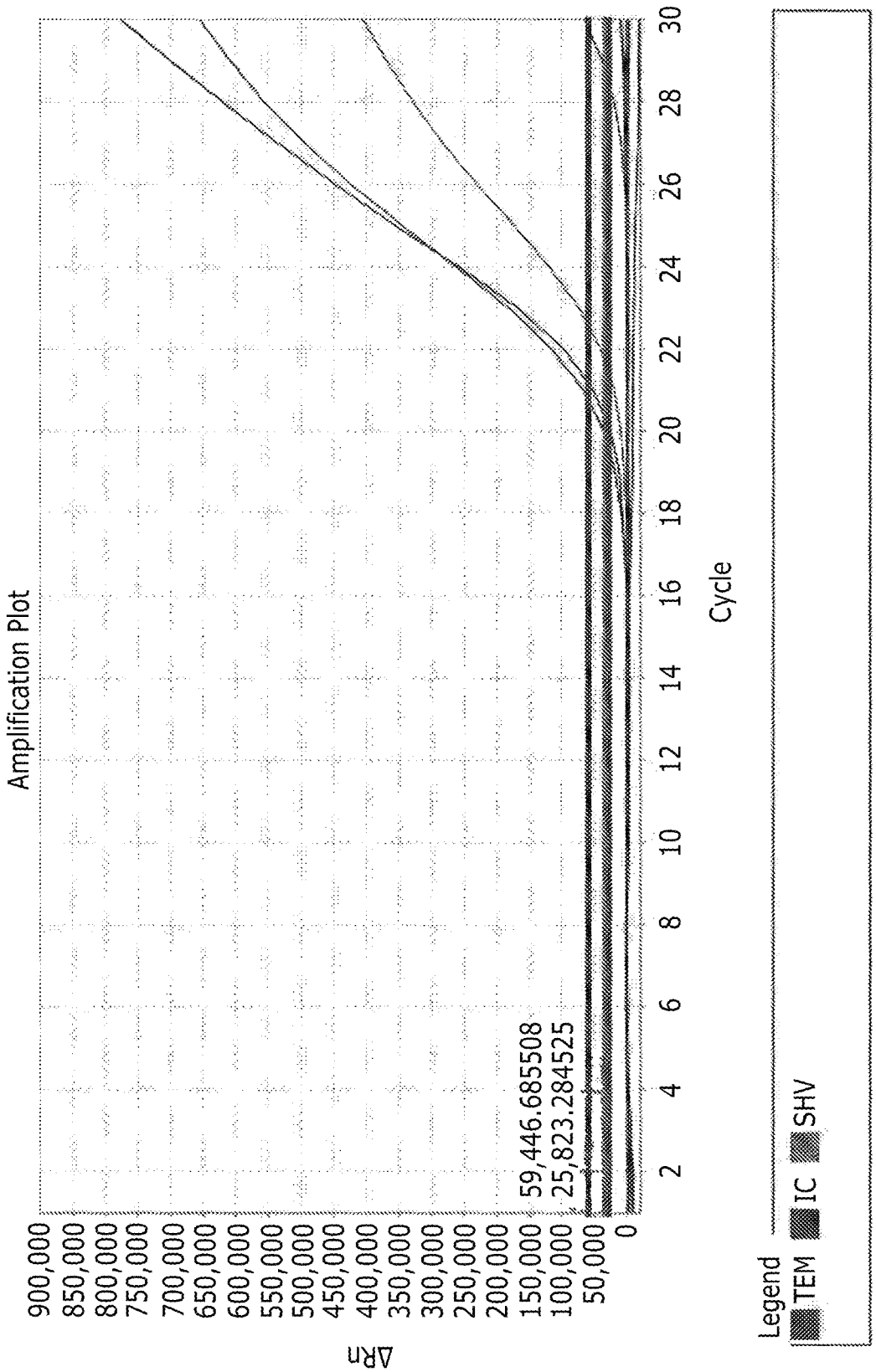
FIG. 9 depicts an amplification plot of an exemplary internal control mix of a kit including SHV-TEM gene targets.

Examples of real-time PCR amplification curves obtained on the ABI QS7 Flex-Real-Time System for some of the multiplex mixes described herein are shown in FIGS. 1-9. FIG. 1 depicts an amplification plot of an exemplary mix 1 including ampC gene targets. FIG. 2 depicts an amplification plot of an exemplary mix 2 including ampC gene targets. FIG. 3 depicts an amplification plot of an exemplary mix 1 including β-lactamase gene targets. FIG. 4 depicts an amplification plot of an exemplary mix 2 including β-lactamase gene targets. FIG. 5 depicts an amplification plot of an exemplary mix 3 including β-lactamase gene targets. FIG. 6 depicts an amplification plot of an exemplary internal control mix including MCR gene targets. FIG. 7 depicts an amplification plot of an exemplary mix 1 including OXA gene targets. FIG. 8 depicts an amplification plot of an exemplary mix 2 including OXA gene targets. FIG. 9 depicts an amplification plot of an exemplary internal control mix including SHV-TEM gene targets.

The method may include using one or more oligonucleotide primers that are complementary to at least a portion of the nucleic acid sequence of interest. The method may include annealing several pairs of primers to different target DNA sequences. The method may include annealing primer/probe sequences to bacterial nucleic acid sequences comprising targeted antibiotic resistant gene family variants of β-lactamases. The primer and/or probe sequences may anneal with 100% specificity to the target gene variants. The primer and/or probe sequences may anneal with about 95% specificity to the target gene variants. The primer and/or probe sequences may anneal with about 90% to about 100% specificity to the target gene variants. The primer and/or probe sequences may anneal with about 80% to about 100% specificity to the target gene variants.

The method may include using temperature mediated DNA polymerase. The method may include using fluorescent dyes. The method may include the using sequence specific DNA probes including oligonucleotides labeled with a reporter. The method may include using a microarray.

The method may include using a thermal cycler. For example, the kit of the present teachings may be utilized with the following PCR systems: Streck ZULU RT™ PCR System, Applied Biosystems (ABI) QuantStudio 7 (QS7) Flex Real-Time System, ABI 7500 Real-Time PCR System, QIAGEN Rotor-Gene® Q, and CFX96 Touch™ Real-Time PCR Detection System, Applied Biosystems™ 7500 Fast Dx Real-Time PCR Instrument, Roche LightCycler®480 I and II, and Cepheid SmartCycler®. It is contemplated that any detection system capable of detecting the multiplex fluorescent signal provided in the kit of the present teachings may be suitable.

The method may include real-time monitoring of qPCR reaction products. The probes may generate a signal when hyrodolyzed by the DNA polymerase causing liberation of a detectable fluorescent signal. The real-time monitoring method may employ fluorescence at different wavelengths. The method may include the use of DNA-intercalating fluorescent dyes. The method may include the use of a target specific nucleotide probe labeled with a fluorescent tag at one end. The other end of the hybridization probe may be labeled with a fluorescent quencher. Fluorescent hybridization probes generate a fluorescence signal only when they bind to their target and enable real-time of monitoring of nucleic acid amplification assays.

Surprisingly, some DNA targets detected with these kits, allow for amplification of regions of DNA much larger than the conventional wisdom within the real-time PCR field. For example, most amplicons would traditionally be between 50 to 150 base pairs in size. The present teachings allow for successfully amplified amplicons up to 553 base pairs by real-time PCR.

There may be one or more benefits to detecting larger amplicons. Larger amplicons may, in some cases, provide greater specificity for a specific antibiotic resistance gene family. Detection of larger amplicons may permit detection of an increased number of gene variants within a given resistance gene family. Detection of larger amplicons may also allow confirmation by agarose gel electrophoresis since the molecular sizes of each gene that is detected can be resolved from one another.

The efficiency of detection for each target in a dilution series may be measured for amplicons between 25 base pairs and 2000 base pairs. The efficiency of the PCR for amplicons within this size range may be from 80% to 110%. More specifically, the efficiency of the reactions may be from 90% to 105%. The coefficient of determination may be from 0.98 to 1.1. More specifically, the coefficient of determination may be from 0.99 to 1.0. The limit of detection may be from 0.1 copies to $1\times10^{10}$ copies.

Alternate sequences for primer, probes, and DNA controls for β-lactamase gene targets of the present teachings are depicted in Table 2 and Table 3. [SEQ. ID NOS 1-48 and SEQ. ID NOS 49-66]

Primers and/or probes may be degenerate at any nucleotide position. Primers and/or probes may not be degenerate at any nucleotide position. Any suitable fluorophore and/or quencher and nucleic acid sequence combination may be used. For example, a probe may be labeled with a fluorescent tag at one end and a fluorescent quencher at the other end. For example, a probe may be labeled with a fluorescent tag at one end and a fluorescent quencher at the other end. For example, two fluorescent quenchers may be included at one end or within the probe sequence. It is contemplated that the probe sequences of the present teachings may be labeled with any suitable fluorophore and quencher combinations. For example, any fluorophore of the present teachings may be attached to any probe DNA sequence of the present teachings.

TABLE 2

| | Primer/Probe | Sequence |
|---|---|---|
| SEQ ID NO. 1 | MOX F' | AGA CCC TGT TCG AGA TAG |
| SEQ ID NO. 2 | MOX R' | ATG GTG ATG CTG TCA AAG |
| SEQ ID NO. 3 | MOX-FAM | 5'-56-FAM-CGT GAG CAA GAC CCT GAC TG-3'BHQ1 |
| SEQ ID NO. 4 | FOX F' | ACT ATT TCA ACT ATG GGG TT |

TABLE 2-continued

| | Primer/Probe | Sequence |
|---|---|---|
| SEQ ID NO. 5 | FOX R' | TTG TCA TCC AGC TCA AAG |
| SEQ ID NO. 6 | FOX-TEX | 5'-Tex615-TGA CCG CAG CAT AGG CAC-3'BHQ_2 |
| SEQ ID NO. 7 | EBC F' | GTG GCG GTG ATT TAT GAG |
| SEQ ID NO. 8 | EBC R' | CGG TGA AGG TTT TAC TTA TAG AA |
| SEQ ID NO. 9 | EBC-HEX | 5'-5HEX/CAGCCGCAC/ZEN/TACTTCACCT/-3'BHQ_1 |
| SEQ ID NO. 10 | DHA F' | TGCGTACGGTTATGAGAACAA |
| SEQ ID NO. 11 | DHA R' | CCCAGCGCAGCATATCTT |
| SEQ ID NO. 12 | DHA-FAM | ATGCGGAATCTTACGGCGTGGAAT |
| SEQ ID NO. 13 | CMY F' | TCC AGC GTT ATT GAT ATG G |
| SEQ ID NO. 14 | CMY R' | CAT CTC CCA GCC TAA TCC |
| SEQ ID NO. 15 | CMY-TEX | 5'TexRd-XN/ACATATCGCCAATACGCCAGT/3IAPRQSp/-3' |
| SEQ ID NO. 16 | ACC F' | GCCGCTGATGCAGAAGAATA |
| SEQ ID NO. 17 | ACC R' | TTT GCC GCT AAC CCA TAG TT |
| SEQ ID NO. 18 | ACC-HEX | 5'-/5HEX/TCA CTG CGA/ZEN/CCG ACA TAC CG/3IABkFQ/-3' |
| SEQ ID NO. 19 | IC F' | GAG AGG ATG ACC AGC CAC AC |
| SEQ ID NO. 20 | IC R' | AGT ACT TTA CAA CCC GAA GGC |
| SEQ ID NO. 21 | IC-TYE | 5'/5TYE665/TGA GAC ACG GTC CAG ACT CCT ACG G/3BHQ_2/-3' |
| SEQ ID NO. 22 | CTX-M-14 F' | 5'-TTGGTGACGTGGCTCAAA-3' |
| SEQ ID NO. 23 | CTX-M-14 R' | 5'-ATATCATTGGTGGTGCCGTAG-3' |
| SEQ ID NO. 24 | CTX-M-14-FAM | 5'-/56-FAM/CGTGGACTG/ZEN/TGGGTGATAAGACCG/3IABkFQ/-3' |
| SEQ ID NO. 25 | CTX-M-15 F' | 5'-GTCACGCTGTTGTTAGGAAGT-3' |
| SEQ ID NO. 26 | CTX-M-15 R' | 5'-TAATCAATGCCACACCCAGTC-3' |
| SEQ ID NO. 27 | CTX-M-15-TEX615 | 5'-/5TEX615/AACTTGCCGAATTAGAGCGGCAGT/3BHQ_2/-3' |
| SEQ ID NO. 28 | OXA48-F' | 5'-AGCAGCAAGGATTTACCAATAATC-3' |
| SEQ ID NO. 29 | OXA48-R' | 5'-CGTCTGTCCATCCCACTTAAA-3' |
| SEQ ID NO. 30 | OXA48-HEX | 5'-/5HEX/TAGCTTGAT/ZEN/CGCCCTCGATTTGGG/3IABkFQ/-3' |
| SEQ ID NO. 31 | CMY F' | 5'-TCCAGCGTTATTGATATGG-3' |
| SEQ ID NO. 32 | CMY R' | 5'-CATCTCCCAGCCTAATCC-3' |
| SEQ ID NO. 33 | CMY-TxR | 5-/5TexRd-XN/ACATATCGCCAATACGCCAGT/3IAbRQSp/-3' |
| SEQ ID NO. 34 | NDM F' | 5'-TTTGATCGTCAGGGATGGC-3' |
| SEQ ID NO. 35 | NDM R' | 5'-CAGGTTGATCTCCTGCTTGAT-3' |
| SEQ ID NO. 36 | NDM-HEX | 5-/5HEX/AGACCGCCC/ZEN/AGATCCTCAACTG/3IABkFQ/-3' |
| SEQ ID NO. 37 | KPC F' | 5'-CGCTAAACTCGAACAGGACTT-3' |
| SEQ ID NO. 38 | KPC R' | 5'-TAACTTACAGTTGCGCCTGAG-3' |
| SEQ ID NO. 39 | KPC-FAM | 5'-/5TYE665/ATCGGTGTGTACGCGATGGATACC/3BHQ_2/-3' |
| SEQ ID NO. 40 | VIM F' | 5'-CATTCGACCGACAACTTAG-3' |

TABLE 2-continued

| | Primer/Probe | Sequence |
|---|---|---|
| SEQ ID NO. 41 | VIM R' | 5'-CGTGCGTGACAACTCAT-3' |
| SEQ ID NO. 42 | VIM-TEX | 5'45TEX615/TGTGCTCTATGGTGGTTGTGCGAT/3BHQ_2/-3' |
| SEQ ID NO. 43 | DHA F' | 5'-TGCGTACGGTTATGAGAACAA-3' |
| SEQ ID NO. 44 | DHA R' | 5'-CCCAGCGCAGCATATCTT-3' |
| SEQ ID NO. 45 | DHA-FAM | 5'-/56-FAM/ATGCGGAAT/ZEN/CTTACGGCGTGAAAT/3IABkFQ-3' |
| SEQ ID NO. 46 | IMP F' | 5'-ACGTAGTGGTTTGGTTACCTG-3' |
| SEQ ID NO. 47 | IMP R' | 5'-AAGCTTCTAAATTTGCGTCACC-3' |
| SEQ ID NO. 48 | IMP-TYE705 | 5'-/5HEX/TTTGTTAAA/ZEN/CCGGACGGTCTTGGT/3IABkFQ/-3' |

TABLE 3

| | DNA Control | Sequence |
|---|---|---|
| SEQ ID NO. 49 | MOX | AACCGGGAGAGCGGGGCCAGCGTCAGCGAGCAGACCCTGTTCGAGATAGGATCCGTGAGCAAGACCCTGACTGCGACCCTGGGGGCCTATGCGGTGGTCAAGGGAGCGATGCAGCTGGATGACAAGGCGAGCCGGCACGCGCCCTGGCTCAAGGGATCCGTCTTTGACAGCATCACCATGGGGGAGCTTGCCACCTACAGC |
| SEQ ID NO. 50 | FOX | GGGGATGGCGGTCGCCGTGCTGAAAGATGGCAAGGCCCACTATTTCAACTATGGGGTTGCCAACCGCGAGAGTGGTCAGCGCGTCAGCGAGCAGACCCTGTTCGAGATTGGCTCGGTCAGCAAGACCCTGACCGCGACCCTCGGTGCCTATGCTGCGGTCAAGGGGGGCTTTGAGCTGGATGACAAGGTGAGCCAGCACGCCCCCTGGCTCAAAGGTTCCGCCTTTGATGGTGTGACCAT |
| SEQ ID NO. 51 | EBC | GGACCGTTACGCCGCTGATGAAAGCGCAGGCCATTCCGGGTATGGCGGTGGCGGTGATTTATGAGGGTCAGCCGCACTACTTCACCTTCGGTAAAGCCGATGTTGCGGCGAACAAACCTGTCACTCCACAAACCTTGTTCGAACTGGGTTCTATAAGTAAAACCTTCACCGGCGTACTCGGTGGCGATGCCATTGCTCGCGGTGAAATATCGCTGGGCGA |
| SEQ ID NO. 52 | DHA | GACTGCACGGATCCTGGCACCGCTGGGGTTATCTCACACCTTTATTACTGTGCCGGAAAGTGCGCAAAGCCAGTATGCGTACGGTTATGAGAACAAAAAACCGGTCCGCGTGTCGCCGGGACAGCTTGATGCGGAATCTTACGGCGTGGAATCCGCCTCAAAAGATATGCTGCGCTGGGCGGAAATGAATATGGAGCCGTCACGGGCCGGTAATGCGGAT |
| SEQ ID NO. 53 | CMY | GCCTGTACACGTTTCTCCGGGACAACTTGACGCCGAAGCCTATGGCGTGAAATCCAGCGTTATTGATATGGCCCGCTGGGTTCAGGTCAACATGGACGCCAGCCGCGTTCAGGAGAAAACGCTCCAGCAGGGCATTGCGCTTGCGCAGTCTCGCTACTGGCGTATTGGCGATATGTACCAGGGATTAGGCTGGGAGATGCTGAACTGGCCGCTGAAAGCTGATTCGATCATCAACGGTAGCGACAGCAAAGTGGCATTGG |
| SEQ ID NO. 54 | ACC | GAGAGCAAAATTAAAGACACCGTTGATGACCTGATCCAGCCGCTGATGCAGAAGAATAATATTCCCGGTATGTCGGTCGCAGTGACCGTCAACGGTAAAAACTACATTTATAACTATGGGTTAGCGGCAAAACAGCCTCAGCAGCCGGTT |
| SEQ ID NO. 55 | IC | AGCTTGTTGGTGGGGTAACGGCTCACCAAGGCGACGATCCCTAGCTGGTCTGAGAGGATGACCAGCCACACTGGAACTGAGACACGGTCCAGACTCCTACGGGAGGCAGCAGTGGGGAATATTGCACAATGGGCGCAAGCCTGATGCAGCCATGCCGCGTGTATGAAGAAGGCCTTCGGGTTGTAAAGTACTTTCAGCGGGGAGGAAGGGAGTAAAGTTAATACCTTTGCTCATTGACGTTACCCGCAGAAGAAGCACCGGCTAACTCCG |
| SEQ ID NO. 56 | CTX-M-14 | CGTTTCGTCTGGATCGCACTGAACCTACGCTGAATACCGCCATTCCCGGCGACCCGAGAGACACCACCACGCCGCGGGCGATGGCGCAGACGTTGCGTCAGCTTACGCTGGGTCATGCGCTGGGCGAAACCCAGCGGGCGCAGTTGGTGACGTGGCTCAAAGGCAATACGACCGGCGCAGCCAGCATTCGGGCCGGCTTACCGACGTCGTGGACTGTGGGTGATAAGACCGGCAGCGGCGACTACGGCACCACCAATGATATTGCGGTGATCTGGCCGCAGGGTCGTGCGCCGCTGGTTCTGGTGACCTATTTTACCCAGC |

TABLE 3-continued

| | DNA Control | Sequence |
|---|---|---|
| SEQ ID NO. 57 | CTX-M-15 | CCGTCACGCTGTTGTTAGGAAGTGTGCCGCTGTATGCGCAAACGGCGGAC<br>GTACAGCAAAAACTTGCCGAATTAGAGCGGCAGTCGGGAGGCAGACTGG<br>GTGTGGCATTGATTAACACAGC |
| SEQ ID NO. 58 | OXA | AATCACAGGGCGTAGTTGTGCTCTGGAATGAGAATAAGCAGCAAGGATTT<br>ACCAATAATCTTAAACGGGCGAACCAAGCATTTTTACCCGCATCTACCTTTA<br>AAATTCCCAATAGCTTGATCGCCCTCGATTTGGGCGTGGTTAAGGATGAAC<br>ACCAAGTCTTTAAGTGGGATGGACAGACGCGCGATATCGCCACTTGGAAT<br>CGCGATCATAATCTAATCACCGCGATGAAATATTCAGTTGTGCCTGTTTAT<br>CAAGAATTTGCCCGCCAAATTGGCGAGGCACGTATGAGCAAGATGCTACA<br>TGCTTTCGATTATGGTAATGAGGACATTTCGGGCAATGTAGACAGTTTCTG<br>GCTCGACGGTGGTATTCGAATTTCGGCCACGGAGCAAATCAGCTTTTTAA<br>GAAAGCTGTATCACAATAAGTTACACGTATCGGAGCGCAGCCAGCGTATT<br>GTCAAACAAGCCATGCTGACCGAAGCCAATGGTGACTAATTATTCGGGCT<br>AAAACTGGATACTCGACTAGAATCGAACCTAAGATTGGCTGGCTGGGT |
| SEQ ID NO. 59 | IC | CGGAGTTAGCCGGTGCTTCTTCTGCGGGTAACGTCAATGAGCAAAGGTAT<br>TAACTTTACTCCCTTCCTCCCCGCTGAAAGTACTTTACAACCCGAAGGCTT<br>CTTCATACACGCGGCATGGCTGCATCAGGCTTGCGCCCATTGTGCAATATT<br>CCCCACTGCTGCCTCCCGTAGGAGTCTGGACCGTGTCTCAGTTCCAGTGTG<br>GCTGGTCATCCTCTCAGACCAGCTAGGGATCGTCGCCTTGGTGAGCCGTTA<br>CCCCACCAACAAGCT |
| SEQ ID NO. 60 | CMY | GCCTGTACACGTTTCTCCGGGACAACTTGACGCCGAAGCCTATGGCGTGA<br>AATCCAGCGTTATTGATATGGCCCGCTGGGTTCAGGTCAACATGGACGCC<br>AGCCGCGTTCAGGAGAAAACGCTCCAGCAGGGCATTGCGCTTGCGCAGTC<br>TCGCTACTGGCGTATTGGCGATATGTACCAGGGATTAGGCTGGGAGATGC<br>TGAACTGGCCGCTGAAAGCTGATTCGATCATCAACGGTAGCGACAGCAAA<br>GTGGCATTGG |
| SEQ ID NO. 61 | NDM | GGCGAAAGTCAGGCTGTGTTGCGCCGCAACCATCCCCTCTTGCGGGGCAA<br>GCTGGTTCGACAACGCATTGGCATAAGTCGCAATCCCCGCCGCATGCAGC<br>GCGTCCATACCGCCCATCTTGTCCTGATGCGCGTGAGTCACCACCGCCAGC<br>GCGACCGGCAGGTTGATCTCCTGCTTGATCCAGTTGAGGATCTGGGCGGT<br>CTGGTCATCGGTCCAGGCGGTATCGACCACCAGCACGCGGCCGCCATCCC<br>TGACGATCAAAC |
| SEQ ID NO. 62 | KPC | GTATCGCCGTCTAGTTCTGCTGTCTTGTCTCTCATGGCCGCTGGCTGGCTTT<br>TCTGCCACCGCGCTGACCAACCTCGTCGCGGAACCATTCGCTAAACTCGAA<br>CAGGACTTTGGCGGCTCCATCGGTGTGTACGCGATGGATACCGGCTCAGG<br>CGCAACTGTAAGTTACCGCGCTGAGGAGCGCTTCCCACTGTGCAGCTCATT<br>CAAGG |
| SEQ ID NO. 63 | VIM | CCATTCAGCCAGATCGGCATCGGCCACGTTCCCCGCAGACGTGCGTGACA<br>ACTCATGAATCGCACAACCACCATAGAGCACACTCGCAGACGGGACGTAC<br>ACAACTAAGTTGTCGGTCGAATGCGCAGCACCAGGATAGAAGAGTTCTAC<br>TGGACCGAAGCGCACTGCGTCCCCGCTCGAGTCCTTCTAGAGAGTGCGTG<br>GGAATCTCGTTCCCCTCTACCTCGGCTAGCCGGCGTGTCGACGGTGATGC<br>GTACGTTGCCACCCCAGCCGCCCGAAGGACATCAACGCCGCC |
| SEQ ID NO. 64 | DHA | GACTGCACGGATCCTGGCACCGCTGGGGTTATCTCACACCTTTATTACTGT<br>GCCGGAAAGTGCGCAAAGCCAGTATGCGTACGGTTATGAGAACAAAAAA<br>CCGGTCCGCGTGTCGCCGGGACAGCTTGATGCGGAATCTTACGGCGTGAA<br>ATCCGCCTCAAAAGATATGCTGCGCTGGGCGGAAATGAATATGGAGCCGT<br>CACGGGCCGGTAATGCGGAT |
| SEQ ID NO. 65 | IC | CGGAGTTAGCCGGTGCTTCTTCTGCGGGTAACGTCAATGAGCAAAGGTAT<br>TAACTTTACTCCCTTCCTCCCCGCTGAAAGTACTTTACAACCCGAAGGCTT<br>CTTCATACACGCGGCATGGCTGCATCAGGCTTGCGCCCATTGTGCAATATT<br>CCCCACTGCTGCCTCCCGTAGGAGTCTGGACCGTGTCTCAGTTCCAGTGTG<br>GCTGGTCATCCTCTCAGACCAGCTAGGGATCGTCGCCTTGGTGAGCCGTTA<br>CCCCACCAACAAGCT |
| SEQ ID NO. 66 | IMP | GCGGAGTTAGTTATTGGCTAGTTAAAAATAAAATTGAAGTTTTTTATCCCG<br>GCCCGGGGCACACTCAAGATAACGTAGTGGTTTGGTTACCTGAAAAGAAA<br>ATTTTATTCGGTGGTTGTTTTGTTAAACCGGACGGTCTTGGTAATTTGGGT<br>GACGCAAATTTAGAAGCTTGGCC |

The sequence listing including SEQ ID NOS 1-295 is hereby incorporated by reference for all purposes.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the of a range in terms of "at least 'x' parts by weight of the resulting composition" also contemplates a teaching of ranges of same recited amount of "x" in percent by weight of the resulting composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for ail purposes. The term "consisting essentially of to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist of, or consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A kit for identification of one or more β-lactamase genes, wherein the one or more β-lactamase genes are selected from the group consisting of: CMY-2, DHA, MOX, ACC, FOX, and ACT/MIR genes, the kit comprising probes comprising the following sequences: AGGATGGCAAGGCCCACTATTTCA (SEQ ID NO: 194), AGCCATTACGTTCCAGAGTTGCGT (SEQ ID NO: 197), TCTGCTGAAGTTTRYCGAGGCMAA (SEQ ID NO: 200), TGAGACACGGTCCAGACTCCTACG (SEQ ID NO: 203), AAACCGGGCGATATGCGTCTGTAT (SEQ ID NO: 206), GATGCCATTGCYCGSGGTGAAAT (SEQ ID NO: 209), and ATGTTGGCCTGAACCCAGCG (SEQ ID NO: 212), wherein each probe comprises a fluorophore and/or a fluorescent quencher.

2. The kit of claim 1, including an endogenous internal control.

3. The kit of claim 2, wherein the endogenous internal control targets a conserved region in Gram-negative bacteria.

4. The kit of claim 2, wherein the internal control detects a 16S rRNA gene.

5. The kit of claim 2, wherein the internal control detects a 16S rRNA gene for *E. coli, Pseudomonas, Acinetobacter, Klebsiella,* or *Salmonella*.

6. The kit of claim 1, including at least one control DNA mix.

7. The kit of claim 1, including exactly two control DNA mixes.

8. The kit of claim 1, including exactly three control DNA mixes.

9. The kit of claim 1, including a composition containing a tracking dye.

10. A method for identifying one or more β-lactamase genes selected from the group consisting of CMY-2, DHA, MOX, ACC, FOX, and ACT/MIR, the method comprising assaying a biological sample using the kit of claim 1 to identify the one or more β-lactamase genes, wherein the assaying comprises real-time polymerase chain reaction.

11. The method of claim 10, wherein 0.1 copy to 10,000,000,000 copies of target DNA sequence is detected.

12. The method of claim 10, wherein the biological sample is a clinical sample of blood, plasma, urine or feces, or of rectal, nose, throat, skin, wound or cerebrospinal fluid specimens.

13. The kit of claim 1, further comprising the following primers: GCTGCTCAAGGAGCACAGGAT (SEQ ID NO: 192), CACATTGACATAGGTGTGGTGC (SEQ ID NO: 193), AACAGCCTCAGCAGCCGGTTA (SEQ ID NO: 195), TTCGCCGCAATCATCCCTAGC (SEQ ID NO: 196), GCCGAGGCTTACGGGATCAAG (SEQ ID NO: 198), CAAAGCGCGTAACCGGATTGG (SEQ ID NO: 199), GAGAGGATGAYCAGCCACAC (SEQ ID NO: 201), and CGCCCATTGTSCAATATTCC (SEQ ID NO: 202).

14. The kit of claim 13, further comprising the following primers: AACTTTCACAGGTGTGCTGGGT (SEQ ID NO: 204), CCGTACGCATACTGGCTTTGC (SEQ ID NO: 205), CTTCCACTGCGGCTGCCAGTT (SEQ ID NO: 208), CCGAAGCCTATGGCGTGAAATCC (SEQ ID NO: 210), GCAATGCCCTGCTGGAGCG (SEQ ID NO: 211), GAGAGGATGAYCAGCCACAC (SEQ ID NO: 213), and CGCCCATTGTSCAATATTCC (SEQ ID NO: 214).

15. The kit of claim 14, wherein the contents of the kit are enclosed in one or more containers.

16. The kit of claim 1, further comprising the following primers: AACTTTCACAGGTGTGCTGGGT (SEQ ID NO: 204), CCGTACGCATACTGGCTTTGC (SEQ ID NO: 205), CTTCCACTGCGGCTGCCAGTT (SEQ ID NO: 208), CCGAAGCCTATGGCGTGAAATCC (SEQ ID NO: 210), GCAATGCCCTGCTGGAGCG (SEQ ID NO: 211), GAGAGGATGAYCAGCCACAC (SEQ ID NO: 213), and CGCCCATTGTSCAATATTCC (SEQ ID NO: 214).

17. The kit of claim 1, wherein each probe is labeled with the fluorophore at one end and the fluorescent quencher at the other end.

18. The kit of claim 1, wherein the fluorophore is selected from the group consisting of fluorescein, hexachlorofluorescein, FAM, HEX, TEX615 and TYE665.

19. The kit of claim 1, wherein the fluorophore excites between 450 nm and 763 nm and emits between 500 nm and 800 nm.

20. The kit of claim 1, wherein peak absorbance of the fluorescent quencher is at 531 nm, 534 nm, 578 nm, or 656 nm.

21. The kit of claim 1, wherein the contents of the kit are enclosed in one or more containers.

* * * * *

UNITED STATES PATENT AND TRADEMARK OFFICE
CERTIFICATE OF CORRECTION

PATENT NO. : 11,708,614 B2
APPLICATION NO. : 16/310074
DATED : July 25, 2023
INVENTOR(S) : Torres-Gonzalez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this
First Day of July, 2025

Coke Morgan Stewart
*Acting Director of the United States Patent and Trademark Office*